(12) United States Patent
Mitchell et al.

(10) Patent No.: US 12,275,732 B2
(45) Date of Patent: Apr. 15, 2025

(54) CYCLIC COMPOUNDS AS RECEPTOR MODULATING THERAPEUTICS AND METHODS AND USES THEREOF

(71) Applicant: Bionomics Limited, Eastwood (AU)

(72) Inventors: Lorna Mitchell, Thebarton (AU); Hamish Toop, Thebarton (AU); Belinda Huff, Thebarton (AU); Justin Ripper, Thebarton (AU); Rajinder Singh, Thebarton (AU); Christophe Morice, Widensolen (FR); Jean-Marie Contreras, Westhouse (FR); Patrick Bazzini, Strasbourg (FR); Laurent Schaeffer, Fortschwihr (FR); Mathieu Michaut, Illkirch (FR)

(73) Assignee: Bionomics Limited, Eastwood (AU)

( * ) Notice: Subject to any disclaimer, the term of this patent is extended or adjusted under 35 U.S.C. 154(b) by 788 days.

(21) Appl. No.: 17/285,064

(22) PCT Filed: Oct. 18, 2019

(86) PCT No.: PCT/AU2019/051137
§ 371 (c)(1),
(2) Date: Apr. 13, 2021

(87) PCT Pub. No.: WO2020/077414
PCT Pub. Date: Apr. 23, 2020

(65) Prior Publication Data
US 2021/0355124 A1 Nov. 18, 2021

(30) Foreign Application Priority Data
Oct. 18, 2018 (AU) ................. 2018903949

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ......... C07D 471/04; A61P 25/22; A61P 25/24
See application file for complete search history.

(56) References Cited

U.S. PATENT DOCUMENTS 10,954,231 B2 * 3/2021 Baell ................ A61K 31/519
2010/0105678 A1 * 4/2010 Baell ................ C07D 471/04
544/127

FOREIGN PATENT DOCUMENTS

| WO | WO-9429295 A1 * 12/1994 | ........... C07D 215/56 |
| WO | WO 2008046135 | 4/2008 |
| WO | WO 2018053240 | 3/2018 |
| WO | WO 2018102885 | 6/2018 |

OTHER PUBLICATIONS

Oxetanes in Drug Discovery: Structural and Synthetic Insights Wuitschik et al. J. Med. Chem. 2010, 53, 3227-3246 (Year: 2010).*
Hippocampal α7 nicotinic ACh receptors contribute to modulation of depression-like behaviour in C57BL/6J mice Mineur et al. British Journal of Pharmacology (2018) 175 1903-1914 (Year: 2018).*
The expanding role of prodrugs in contemporary drug design and development Rautio et al. Nat Rev Drug Discov 17, 559-587 (2018) (Year: 2018).*
International Preliminary Report on Patentability in International Appln. No. PCT/AU2019/051137, dated Apr. 29, 2021, 5 pages.
International Search Report and Written Opinion in International Appln. No. PCT/AU2019/051137, dated Nov. 15, 2019, 9 pages.

* cited by examiner

*Primary Examiner* — Jeffrey S Lundgren
*Assistant Examiner* — Eric Tran
(74) *Attorney, Agent, or Firm* — Fish & Richardson P.C.

(57) ABSTRACT

The present invention relates generally to chemical compounds of formula (I) and methods for their use and preparation. In particular, the invention relates to chemical compounds which are useful in relation to the treatment of diseases, disorders or conditions which would benefit from the modulation of the alpha 7 nicotinic acetylcholine receptor (α7 nAChR), such as anxiety, depression and stress related disorders.

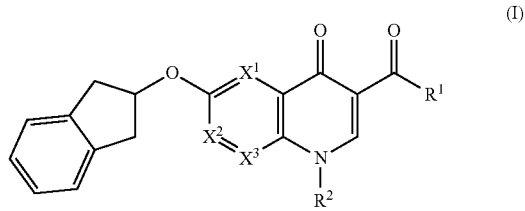

(I)

10 Claims, No Drawings

CYCLIC COMPOUNDS AS RECEPTOR MODULATING THERAPEUTICS AND METHODS AND USES THEREOF

FIELD

The present invention relates generally to chemical compounds and methods for their use and preparation. In particular, the invention relates to chemical compounds which are useful in relation to the treatment of diseases, disorders or conditions which would benefit from the modulation of the alpha 7 nicotinic acetylcholine receptor (α7 nAChR). The invention also relates to the use of these compounds in methods of therapy and the manufacture of medicaments as well as compositions containing these compounds.

BACKGROUND

The α7 nAChRs are rapidly desensitizing cation channels belonging to the cis-loop ligand-gated family. α7 nAChRs play an important role in the regulation of neuronal excitability in different brain regions either by presynaptically modulating neurotransmitter release or by their position on somato-dendritic sites of interneurons and pyramidal cells, where they directly regulate neuronal activity. They are abundantly expressed in the brain, modulate neurotransmitter release and are responsible for direct fast excitatory neurotransmission. At the cellular level, activation of α7 nAChRs can regulate interneuron excitability, modulate the release of excitatory and inhibitory neurotransmitters, and contribute to neuroprotective effects. Positive modulation of α7 nAChRs can enhance hippocampal LTP, and α7 nAChRs are associated with attentional processes and working memory. As a consequence, α7 nAChRs are postulated to be therapeutic targets for treating cognitive impairment, notably in Alzheimer's disease and schizophrenia.

However, here are several lines of evidence to suggest that excessive amounts of acetylcholine (ACh) in the brain contribute to anxious and depressed mood states. One of the most consistent findings in neuropsychiatry is that patients with depression have dysfunctional neuroendocrine systems possibly resulting from prolonged responses to stress and that ACh plays a significant role in mediating neuroendocrine, emotional, and physiological responses to stress. For example, central ACh turnover is increased following stress and ACh facilitates the release of several stress-sensitive neuro-hormones and peptides including corticosterone, adrenocorticotropic hormone (ACTH), and corticotropin releasing factor (CRF). A human imaging study has shown that ACh levels are elevated in patients who are depressed, and remain high in patients who have a history of depression. In addition, other clinical and preclinical studies have shown that blockers of cholinergic receptors can induce antidepressant-like responses. In these human studies, physostigmine, an inhibitor of acetylcholinesterase, increased depressive symptoms in individuals with or without a history of depression. These observations suggest that hyperactivity of brain cholinergic systems can contribute to the pathophysiology of depression.

Studies have shown that α7 nAChRs in both the hippocampus and the amygdala are implicated in the regulation of depression and anxiety. The role of cholinergic signaling in the hippocampus in anxiety- and mood-related behaviors has been investigated in rodents using pharmacological (physostigmine) and molecular genetic techniques (shRNAs targeting AChE) to alter AChE levels or activity in adulthood. In addition, direct infusion of physostigmine or shRNAs into the hippocampus decreased hippocampal AChE which correlated with increased anxiety and depression-like behaviors and decreased resilience to repeated stress in a social defeat paradigm. The behavioral changes due to shRNA-mediated knockdown of AChE were rescued by co-infusion of an shRNA-resistant AChE transgene into the hippocampus and reversed by systemic administration of fluoxetine. These data demonstrate that ACh signaling in the hippocampus promotes behaviors related to anxiety and depression and suggest that abnormalities in the cholinergic system may be critical for the etiology of mood disorders.

Similarly, cholinergic signaling in the basolateral amygdala has also been implicated in behaviors related to stress. The basolateral amygdala (BLA) receives dense cholinergic input from the basal forebrain, affecting both normal functions and dysfunctions of the amygdala. Neuronal excitability in the basolateral nucleus of the amygdala (BLA) is particularly relevant to anxiety. In the BLA, α7 nAChRs are present on somatodendritic regions of glutamatergic neurons, and on somatic and/or dendritic regions of GABAergic interneurons. Pre-clinical studies have implicated both β2 subunit-containing (β2*) and α7 nAChRs in the effects of nicotine in models of anxiety- and depression-like behaviors. Viral-mediated down-regulation of the β2 or α7 nAChR subunit in the amygdala induced robust anxiolytic- and antidepressant-like effects in several mouse behavioral models. α7 nAChR subunit knockdown was effective at decreasing anxiety-like behavior, and reversed the effect of increased ACh signaling in a mouse model of depression. These results suggested that stimulation of α7 nAChRs by acetylcholine may mediate the increased depression-like behaviors during the hyper-cholinergic state observed in depressed individuals and in those with anxiety.

In summary, there is considerable evidence in the literature to suggest that selective inhibition of α7 nAChRs has therapeutic potential for the treatment of anxiety, depression and stress-related disorders. Yet one of the major challenges facing the art is to find and develop therapeutics which are able to effectively penetrate the blood brain barrier. The present invention seeks to improve or enhance the art in this particular area.

SUMMARY OF THE INVENTION

According to an aspect, the present invention provides compounds of formula (I):

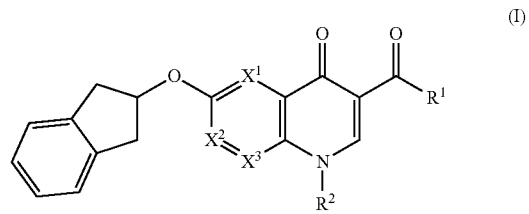

wherein:
R¹ is a (i) morpholinyl group independently substituted one to four times by $C_1$-$C_3$ alkyl or $C_1$-$C_3$ alkoxyl $C_1$-$C_3$ alkyl;
(ii) $C_1$-$C_3$ alkyl bridged morpholinyl group;
(iii) 8 membered N- and O-containing heterocyclyl group optionally $C_1$-$C_3$ alkyl bridged;
(iv) 4 to 6 membered N-containing heterocyclyl group spirofused with a 4 to 6 membered O-containing heterocycle; or (v) 1,4-oxazepane optionally substituted one or two times by $C_1$-$C_3$ alkyl;

$R^2$ is a $C_1$-$C_3$ alkyl; and $X^1$, $X^2$, $X^3$ are independently CH or N wherein at least one of $X^1$, $X^2$ or $X^3$ is N, or pharmaceutically acceptable salts, solvates, prodrugs, stereoisomers or tautomers thereof.

In another aspect the invention provides methods of medically treating a disease, disorder, or condition which would benefit from modulation of α7nAChR, said method including the step of administering an effective amount of a compound of formula (I) or a pharmaceutically acceptable salt, solvates, prodrugs, stereoisomers or tautomers thereof.

In another aspect the invention provides the use of compounds of formula (I) or pharmaceutically acceptable salts, solvates, prodrugs, stereoisomers or tautomers thereof, in the manufacture of a medicament for treating a disease, disorder or condition which would benefit from modulation of α7 nAChR.

In a further aspect the invention provides the use of compounds of formula (I) or pharmaceutical salts, solvates, prodrugs, stereoisomers or tautomers thereof, for treating a disease, disorder or condition which would benefit from modulation of α7 nAChR.

In relation to the aforementioned methods and uses in certain embodiments the disease, disorder or condition which would benefit from modulation of α7 nAChR is a disease, disorder or condition in which the benefit comes from the negative allosteric modulation of α7 nAChR.

In certain embodiments the disease, disorder or condition in which the benefit comes from the negative allosteric modulation of α7 nAChR is a disease, disorder or condition selected from anxiety, depression, or a stress-related disorder.

In certain embodiments, the invention provides compounds, methods and uses based on compounds of subformulae (I) below or pharmaceutically acceptable salts, solvates, prodrugs, stereoisomers or tautomers thereof:

(Ia)

(Ib)

(Ic)

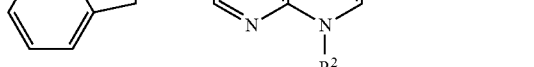
(Id)

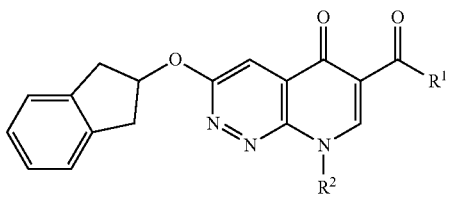

wherein $R_1$ and $R_2$ are as defined above.

DETAILED DESCRIPTION OF THE INVENTION

The present invention is primarily based on the discovery that the compounds of the general formula (I) and sub formula thereof or pharmaceutically acceptable salts, solvates, prodrugs, stereoisomers or tautomers thereof have useful properties as selective negative allosteric modulators of alpha 7 nicotinic acetylcholine receptors and display improved blood brain barrier permeability relative to compounds in similar class. Such compounds have significant potential for the treatment of mood disorders such as anxiety, depression and stress related disorders whether they occur alone or as comorbidities with other conditions.

"Alkyl" refers to monovalent alkyl groups which may be straight chained or branched and have from 1 to 3 carbon atoms or more preferably 1 or 2 carbon atoms. Examples of such alkyl groups include methyl, ethyl, n-propyl and iso-propyl.

"Alkoxy" refers to the group alkyl-O— where the alkyl group is as described above. Examples include methoxy, ethoxy, n-propoxy and iso-propoxy.

"Heterocyclyl" refers to a monovalent saturated group having a single ring, preferably from 1 to 4 carbon atoms and from 1 or 2 hetero atoms selected from nitrogen or oxygen within the ring.

In certain embodiments, the present invention may be used in the treatment of a variety of diseases, disorders or conditions which would benefit from the negative modulation of α7 nAChR, including the step of administering to a patient in need of an effective amount of said compound or a pharmaceutically acceptable salt, solvate, prodrug, stereoisomer or tautomer thereof.

Such diseases, disorders or conditions include:
1) anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder;
2) depressive or bipolar disorders, for example single-episode or recurrent major depressive disorder, dysthymic disorder, bipolar I and bipolar II manic disorders, and cyclothymic disorder;
3) anxiety and/or depression associated with psychotic disorders including schizophrenia;
4) anxiety and/or depression associated with neuroses;
5) anxiety and/or depression associated with convulsions;
6) anxiety and/or depression associated with migraine;
7) anxiety and/or depression associated with neurodegeneration arising from cerebral ischemia;
8) anxiety and/or depression associated with attention deficit hyperactivity disorder;

9) anxiety and/or depression associated with Tourette's syndrome;
10) anxiety and/or depression associated with speech disorders, including stuttering;
11) anxiety and/or depression associated with disorders of circadian rhythm, e.g. in subjects suffering from the effects of jet lag or shift work;
12) anxiety and/or depression associated with autism spectrum disorder (ASD); and
13) stress related disorders.

Further diseases, disorders or conditions for which compounds of the invention may be of benefit include:
1) anxiety and/or depression associated with pain and nociception;
2) anxiety and/or depression associated with emesis, including acute, delayed and anticipatory emesis, in particular emesis induced by chemotherapy or radiation, as well as motion sickness, and post-operative nausea and vomiting;
3) anxiety and/or depression associated with eating disorders including anorexia nervosa and bulimia nervosa;
4) anxiety and/or depression associated with premenstrual syndrome;
5) anxiety and/or depression associated with muscle spasm or spasticity, e.g. in paraplegic patients;
6) anxiety and/or depression associated with hearing disorders, including tinnitus and age-related hearing impairment;
7) anxiety and/or depression associated with urinary incontinence; and
8) anxiety and/or depression associated with the effects of substance abuse or dependency, including alcohol withdrawal.

Compounds of the present invention may be beneficial as pre-medication prior to anaesthesia or minor procedures such as endoscopy, including gastric endoscopy.

The compounds of the invention may be particularly useful in combination therapy, e.g., combining the treatment with other chemotherapeutic treatments (e.g., muscle relaxants, anticonvulants, hypnotics, anaesthetics, analgesics, antidepressants, antipsychotics, or other anxiolytics, etc.).

It will be understood that the compounds of the invention can be used in the treatment of any disease, disorder or condition which may be ameliorated by negative modulation of α7 nAChR.

With reference to formula (I) or sub formulae thereof, in certain embodiments, $R^2$ is ethyl.

With reference to formula (I) and sub-formulae (Ia), (Ib), (Ic) and (Id) in certain embodiments, $R_1$ is selected from one of the following:

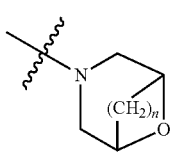

where n is 1, 2 or 3; or

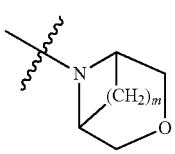

where m is 1, 2 or 3; or

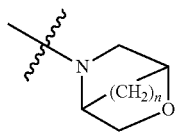

where n is 1, 2 or 3; or

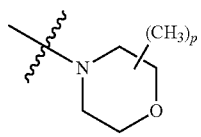

where p is 1 or 2; or

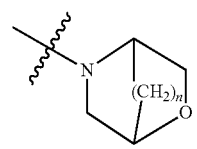

where n is 1, 2 or 3; or

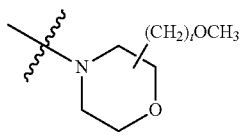

where t is 1 or 2; or

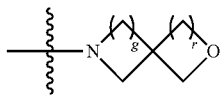

where g and r are independently 1, 2 or 3; or

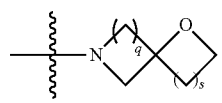

where q and s are independently 1, 2 or 3; or

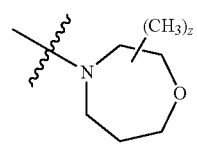

where z is 0, 1, 2 or 3; or

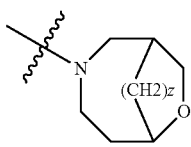
where z is 0, 1, or 2.
In other embodiments $R_1$ is selected from:
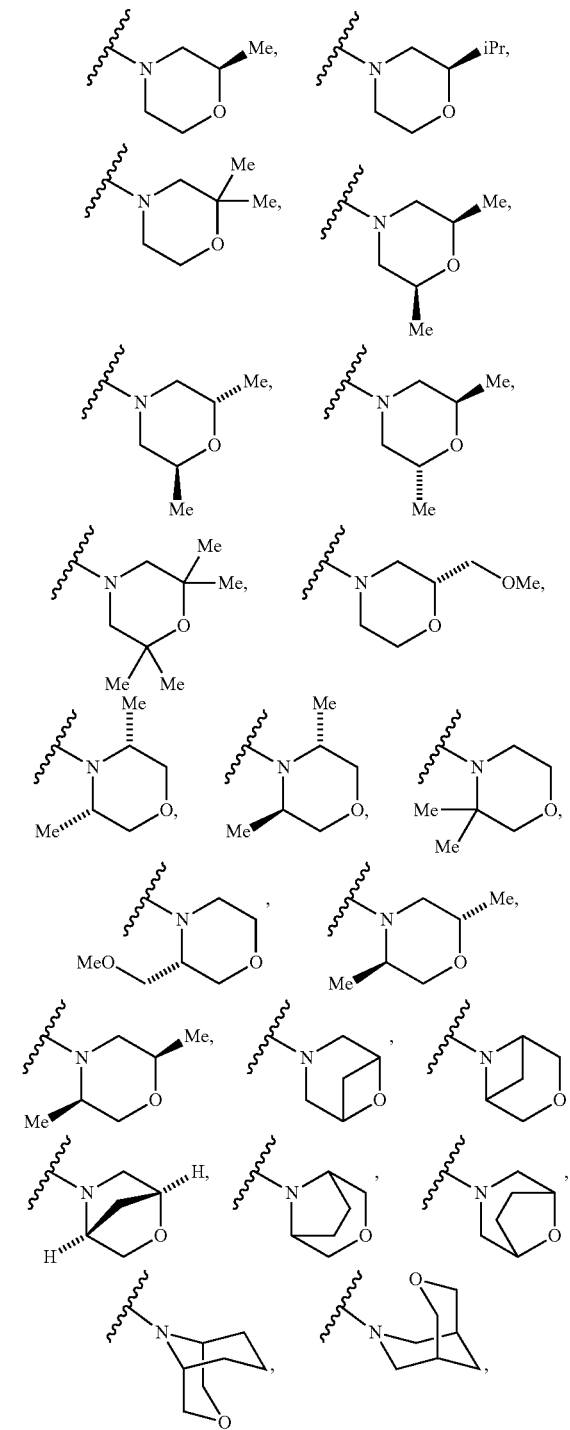
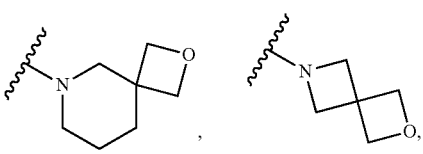
The skilled person would appreciate that:
Examples of:
(i) morpholinyl group independently substituted one to four times by $C_1$-$C_3$ alkyl or $C_1$-$C_3$ alkoxyl $C_1$-$C_3$ alkyl include:
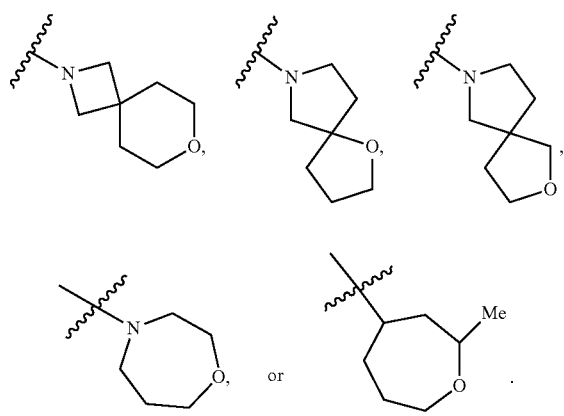
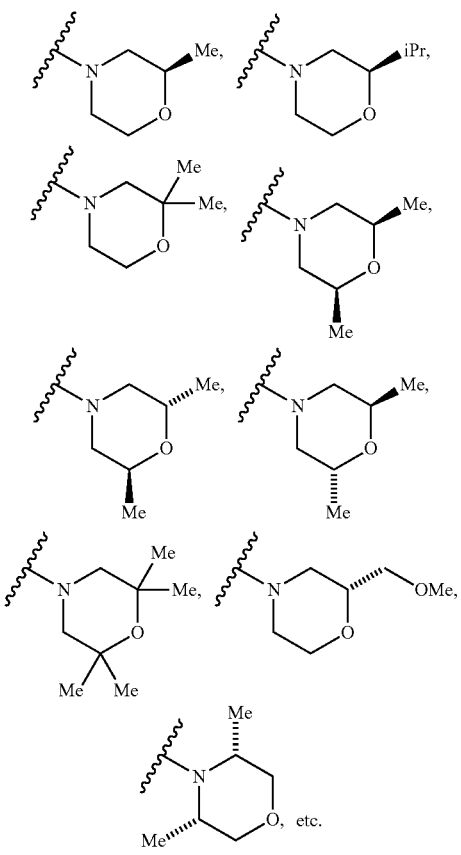

(ii) $C_1$-$C_3$ alkyl bridged morpholinyl group—include:

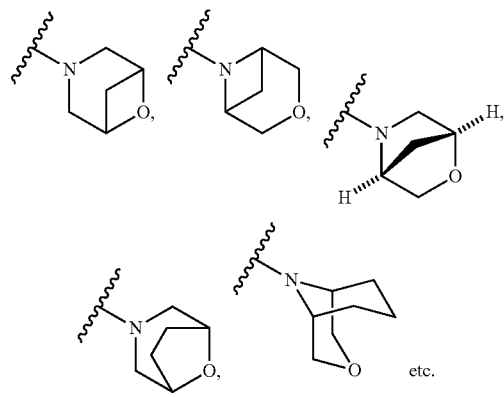

(iii) 8 membered N- and O-containing heterocyclyl group optionally $C_1$-$C_3$ alkyl bridged—include:

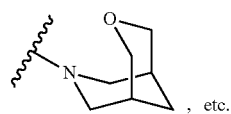 [SMILES: *N1CC2COCC(C2)C1], etc.

(iv) 4 to 6 membered N-containing heterocyclyl group spirofused with a 4 to 6 membered O-containing heterocycle—include:

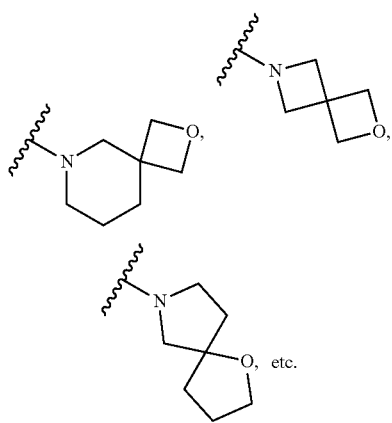, etc.

(v) 1,4-oxazepane optionally substituted one or two times by $C_1$-$C_3$ alkyl include:

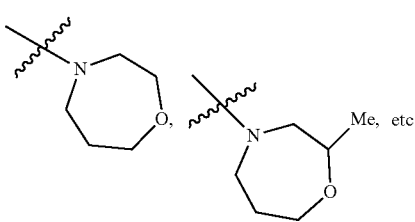 [SMILES: *N1CCCOCC1 ; *N1CCCOC(C)C1]

In an embodiment the compound of formula (I) is a compound of formula (Id) where $R^2$ is
$C_1$-$C_3$ alkyl; and
$R_1$ is selected from:
(i) morpholinyl group independently substituted one to four times by $C_1$-$C_3$ alkyl or $C_1$-$C_3$ alkoxyl $C_1$-$C_3$ alkyl;
(ii) $C_1$-$C_3$ alkyl bridged morpholinyl group;
(iii) 8 membered N- and O-containing heterocyclyl group optionally $C_1$-$C_3$ alkyl bridged;
(iv) 4 to 6 membered N-containing heterocyclyl group spirofused with a 4 to 6 membered O-containing heterocycle; or
(v) 1,4-oxazepane optionally substituted one or two times by $C_1$-$C_3$ alkyl.

In an embodiment the compound of formula (I) is a compound of formula (Id) where $R^2$ is $C_1$-$C_3$ alkyl; and
$R_1$ is an 8 membered N- and O-containing heterocyclyl group optionally $C_1$-$C_3$ alkyl bridged.

In an embodiment the compound of formula (I) is a compound of formula (Id) where $R^2$ is $C_1$-$C_3$ alkyl; and where z is 0, 1, or 2.
$R_1$ is

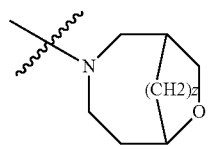

In an embodiment the compound of formula (I) is a compound of formula (Id) where $R^2$ is $C_1$-$C_3$ alkyl; and
$R_1$ is

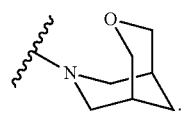.

In an embodiment the compound of formula (I) is a compound of formula (Ic) where $R^2$ is
$C_1$-$C_3$ alkyl; and
$R_1$ is selected from:
(i) morpholinyl group independently substituted one to four times by $C_1$-$C_3$ alkyl or $C_1$-$C_3$ alkoxyl $C_1$-$C_3$ alkyl;
(ii) $C_1$-$C_3$ alkyl bridged morpholinyl group;
(iii) 8 membered N- and O-containing heterocyclyl group optionally $C_1$-$C_3$ alkyl bridged;
(iv) 4 to 6 membered N-containing heterocyclyl group spirofused with a 4 to 6 membered O-containing heterocycle; or
(v) 1,4-oxazepane optionally substituted one or two times by $C_1$-$C_3$ alkyl.

In an embodiment the compound of formula (I) is a compound of formula (Ic) where $R^2$ is $C_1$-$C_3$ alkyl; and
$R_1$ is an 8 membered N- and O-containing heterocyclyl group optionally $C_1$-$C_3$ alkyl bridged.

In an embodiment the compound of formula (I) is a compound of formula (Ic) where $R^2$ is $C_1$-$C_3$ alkyl; and where z is 0, 1, or 2.

$R_1$ is

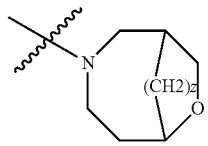

In an embodiment the compound of formula (I) is a compound of formula (Ic) where $R^2$ is $C_1$-$C_3$ alkyl; and
$R_1$ is

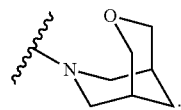 [SMILES: *N1CC2COCC(C2)C1]

In an embodiment the compound of formula (I) is a compound of formula (Ic) where $R^2$ is $C_1$-$C_3$ alkyl; and
$R_1$ is $C_1$-$C_3$ alkyl bridged morpholinyl group.

In an embodiment the compound of formula (I) is a compound of formula (Ic) where $R^2$ is $C_1$-$C_3$ alkyl; and
$R_1$ is

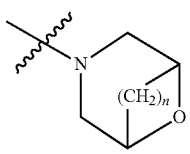

where n is 1, 2 or 3; or

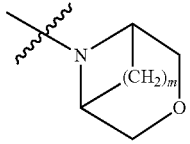

where m is 1, 2 or 3; or,

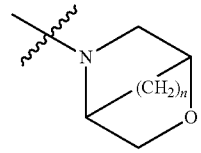

where n is 1, 2 or 3; or

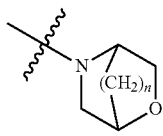

where n is 1, 2 or 3; or
In an embodiment the compound of formula (I) is a compound of formula (Ic) where $R^2$ is $C_1$-$C_3$ alkyl; and where n is 1, 2 or 3.
$R_1$ is

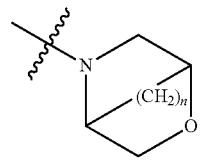

In an embodiment the compound of formula (I) is a compound of formula (Ic) where $R^2$ is $C_1$-$C_3$ alkyl; and
$R_1$ is

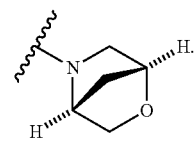

These above structures also include the respective salts, tautomers, opposite stereoisomers as well as mixtures of isomers in all ratios including racemates.

The compounds of the present invention may be prepared based on the following general schemes"

Scheme 1

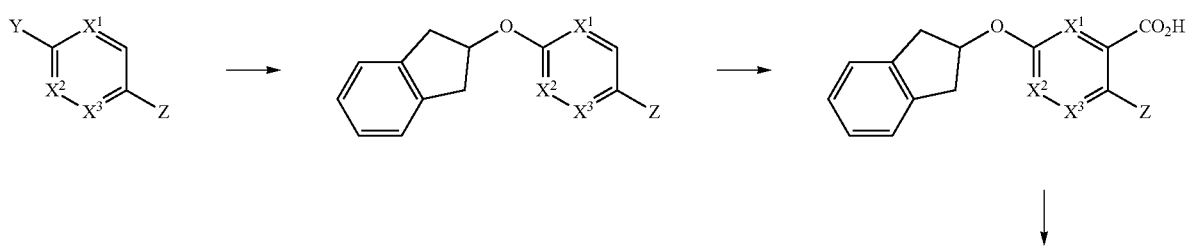

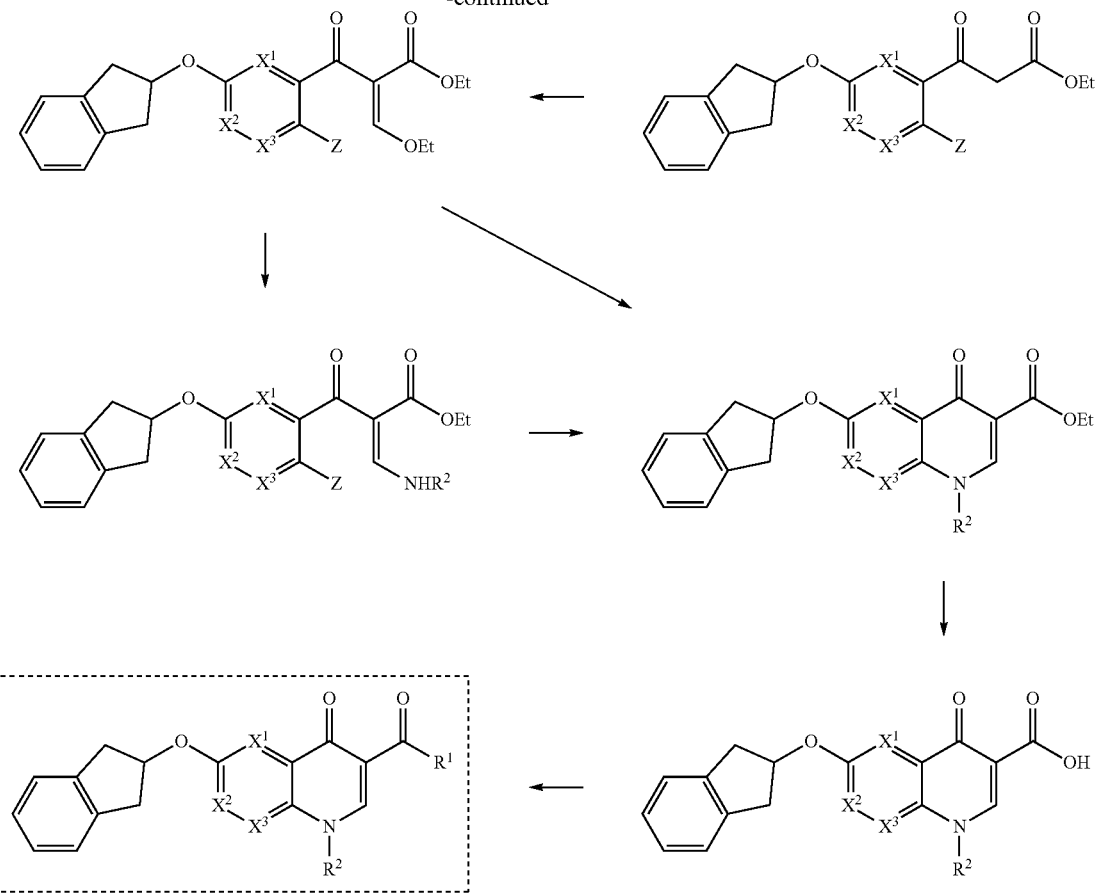
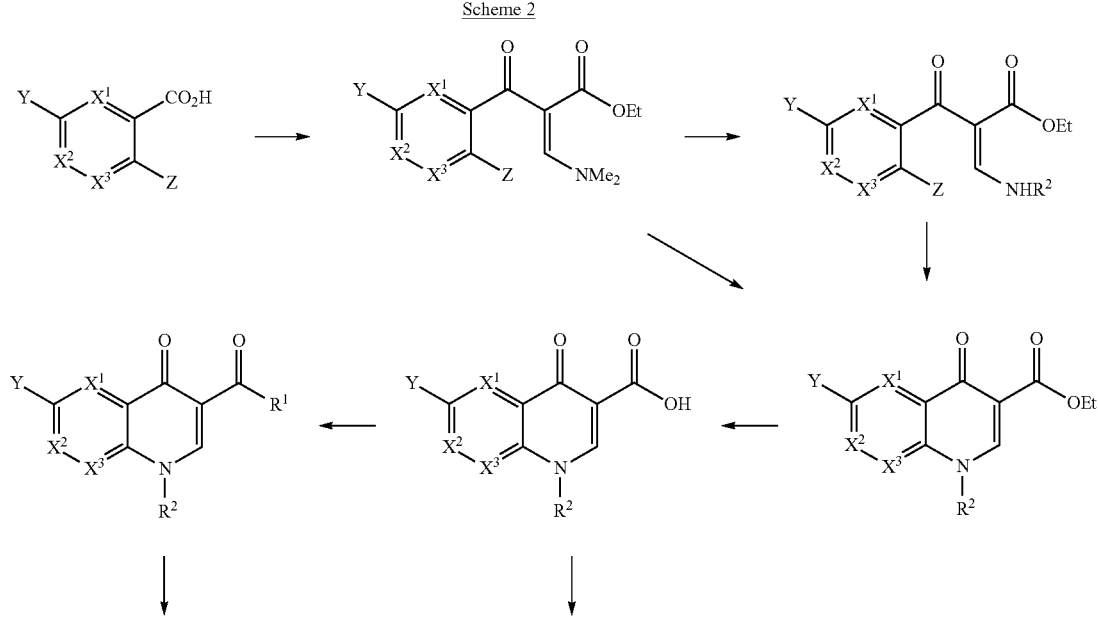
Y = a halogen (F, Cl, Br or I) or OH
Z = a halogen (F, Cl, Br or I)
Scheme 2

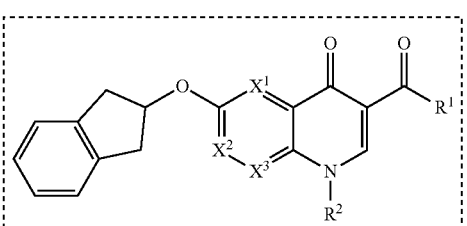

Y = a halogen (F, Cl, Br or I) or OH
Z = a halogen (F, Cl, Br or I)

-continued

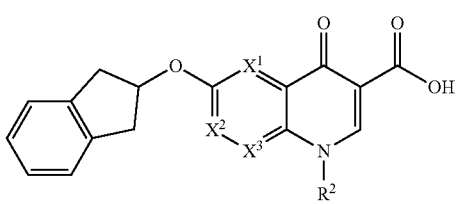

The preparation of the starting materials in the above synthetic procedures may be accomplished using conventional chemistry (see for instance, D. T. Davies, Aromatic Heterocyclic Chemistry, 1993, Oxford Press, New York). Many such starting compounds have also been reported in the literature or are available commercially.

Other compounds of formula (I) can be prepared by the addition, removal or modification of existing substituents. This could be achieved by using standard techniques for functional group inter-conversion that are well known in the industry, such as those described in "Comprehensive organic transformations: a guide to functional group preparations" by Larock R. C., New York, VCH Publishers, Inc. 1989.

During the reactions described above a number of the moieties may need to be protected. Suitable protecting groups are well known in industry and have been described in many references such as Protecting Groups in Organic Synthesis, Greene T W, Wiley-Interscience, New York, 1981.

The compounds of the invention may be particularly useful in combination therapy, e.g., combining the treatment with other chemotherapeutic treatments (e.g., muscle relaxants, anticonvulants, hypnotics, anaesthetics, analgesics or other anxiolytics, etc.).

It will be understood that the compounds of the invention can be used in the treatment of any disease state which may be ameliorated by negative modulation of the alpha 7 nicotinic receptor complex.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular disease of condition being treated.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage may be in the range of 1 mg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another preferred embodiment, the dosage may be in the range of 1 mg to 100 mg per kg of body weight per dosage, such as up to 50 mg per body weight per dosage.

Suitable dosage amounts and dosing regimens can be determined by the attending physician and may depend on the particular condition being treated, the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., inert diluent, preservative disintegrant (e.g., sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Preferably, the compounds of the present invention may be administered to a subject as a pharmaceutically acceptable salt. It will be appreciated however that non-pharmaceutically acceptable salts also fall within the scope of the present invention since these may be useful as intermediates in the preparation of pharmaceutically acceptable salts. Suitable pharmaceutically acceptable salts include, but are not limited to salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluensulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium. In particular, the present invention includes within its scope cationic salts e.g., sodium or potassium salts, or alkyl esters (e.g., methyl, ethyl) of the phosphate group.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

It will be appreciated that any compound that is a prodrug of a compound of formula (I) or sub-formulae thereof is also within the scope and spirit of the invention. The term "pro-drug" is used in its broadest sense and encompasses those derivatives that are converted in vivo to the compounds of the invention. Any compound that is a prodrug of a compound of the invention is within the scope and spirit of the invention.

The compounds of the invention may be in crystalline form either as the free compounds or as solvates (e.g., hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, e.g., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

EXAMPLES

Synthetic Procedure

Abbreviations

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), ether or diethyl ether ($Et_2O$), chloroform ($CHCl_3$), 1,2-dichloroethane (DCE), ethyl acetate (EtOAc, AcOEt), dichloromethane (methylene chloride, DCM), dimethylsulfoxide (DMSO), trifluoroacetic acid (TFA), trifluoroethanol (TFE), dimethylformamide (DMF), 1,2-dimethoxyethane (DME), tetrahydrofuran (THF), triethylamine (TEA, $Et_3N$), N,N-diisopropyl-N-ethylamine (DIEA), sodium sulphate ($Na_2SO_4$), lithium diisopropylamide (LDA), hexamethyldisilazane sodium salt (NaHMDS), trans-dichlorobis(triphenylphosphine)palladium(II) ($PdCl_2(PPh_3)_2$), tetrakis(triphenylphosphine)palladium(0) ($Pd(PPh_3)_4$) tris(dibenzylideneacetone)dipalladium(0) ($Pd_2(dba)_3$), Di-tert-butyl-(2',4',6'-triisopropyl-3-methoxy-6-methyl-[1,1'-biphenyl]-2-yl)phosphine (Rockphos), triphenylphosphine ($PPh_3$), diisopropyl azodicarboxylate (DIAD), carbonyl diimidazole (CDI), propylphosphonic anhydride (T3P), hydrochloric acid (HCl).

Synthetic Procedure

All anhydrous solvents were purchase from commercial sources and stored in Sure-Seal bottles under nitrogen. All other reagents and solvents were purchased as the highest grade available and used without further purification. Thin-layer chromatography (TLC) analysis of reaction mixtures was performed using Merck silica gel 60 F254 TLC plates and visualized using ultraviolet light. Silica gel 60 (40-63 μm, Merck) was used for flash chromatography. Melting points were measured using an Electrothermal 1002 apparatus and were uncorrected. $^1$H NMR (300 MHz) and $^{13}$C NMR (75 MHz) spectra were obtained on a Bruker Advance 300 NMR spectrometer using residual signal of deuterated NMR solvent as internal reference. Mass spectral data and purity of all compounds were acquired on a Thermo LC/MS-Ultimate 3000-Ion Trap HCT Brucker. Mass spectra were obtained on a Brucker Ion Trap applying electrospray ionization (ESI). Purity of all compounds was obtained using a Nucleodur 3 μm 4.6×100 mm reverse-phase column. The eluent was a linear gradient with a flow rate of 1.3 mL/min from 95% A and 5% B to 5% A and 95% B in 8.5 min (solvent A, $H_2O$ with 0.1% $HCO_2H$; solvent B, acetonitrile with 0.1% $HCO_2H$). The compounds were detected at their maximum of absorbance.

In the examples below, in case the structures contain one or more stereogenic centres, the respective structure is depicted in an arbitrary absolute configuration. These structures depict single enantiomers as well as mixtures of enantiomers in all ratios, and/or mixtures of diastereoisomers in all ratios.

General Procedures

General Procedure A: Peptide Coupling Reaction Using T3P

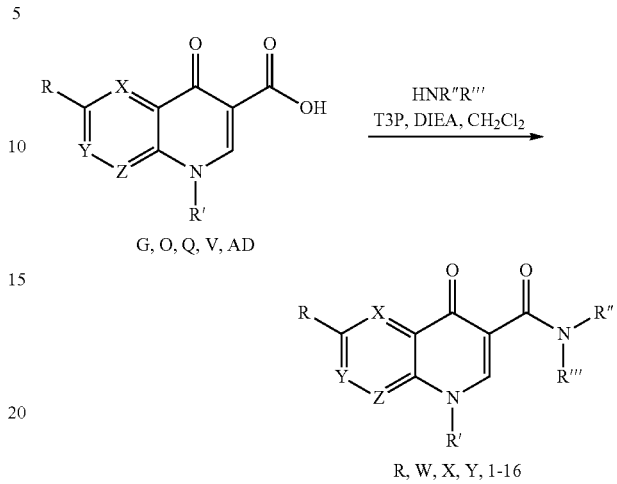

G, O, Q, V, AD

R, W, X, Y, 1-16

Carboxylic acid (1.0 equiv.) was dissolved in dichloromethane (0.1 M). Amine (1.3 equiv.), propylphosphonic anhydride solution 50 wt. % in ethyl acetate (2.8 equiv.) and diisopropyl-ethylamine (4.0 equiv.) were successively added at 0° C. or RT. The reaction mixture was stirred at RT for 18 h and poured into water. The aqueous layer was extracted with dichloromethane. The combined organic fractions were dried over $MgSO_4$, filtered off and concentrated under vacuum. The crude was purified by flash chromatography (elution: cyclohexane/AcOEt then AcOEt/$CH_3OH$) to furnish the pure coupling product.

General Procedure B: Buchwald Coupling Reaction

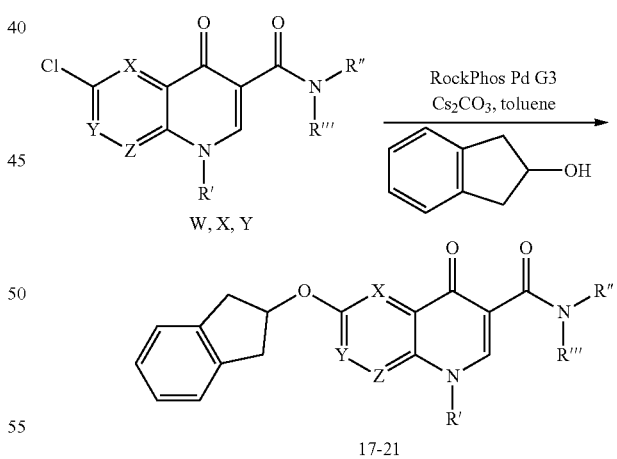

W, X, Y 17-21

A mixture of aryl chloride (1.0 equiv.), 2-indanol (3.0 equiv.), and cesium carbonate (2.0 equiv.) in anhydrous toluene (0.1 M) was degassed under argon for 15 mn at RT. Then RockPhos G3 palladacycle (0.06 equiv.) was added. The mixture was stirred and heated until completion. After cooling and concentration under vacuum, the crude obtained was purified by FC (cyclohexane/AcOEt or AcOEt/$CH_3OH$) and semi-preparative HPLC leading to the pure coupling product.

Intermediate B: 2-Fluoro-5-indan-2-yloxy-pyridine

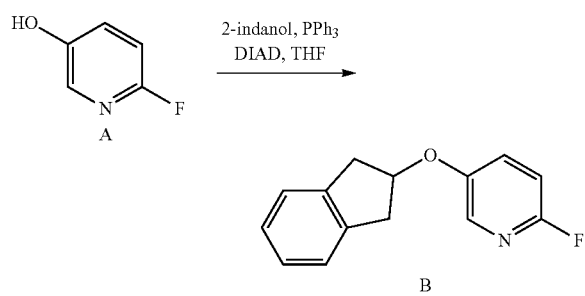

To a solution of 6-fluoropyridin-3-ol (15.0 g, 132.7 mmol) in dry THF (600 ml) at 0° C., were successively added 2-indanol (23.0 g, 171.6 mmol), triphenylphosphine (45.0 g, 172.6 mmol) and DIAD (34 ml, 171.6 mmol). The mixture was stirred 3 days at RT and 3 h at 60° C. After cooling and evaporation of the solvent, the crude was purified by FC (320 g, SiO$_2$, cyclohexane/AcOEt 100:0→70:30) leading to the expected product as a yellow powder (15.7 g, 52%). $^1$H NMR (300 MHz, DMSO-d$_6$) δ 7.88 (t, J=2.1 Hz, 1H), 7.63-7.57 (m, 1H), 7.26-7.23 (m, 2H), 7.17-7.08 (m, 3H), 5.29-5.24 (m, 1H), 3.35 (dd, J=17.1, 6.0 Hz, 2H), 3.00 (dd, J=17.1, 2.1 Hz, 2H). ESIMS m/z [M+H]$^+$ 230.2.

Intermediate C: 2-Fluoro-5-indane-2-yloxy-pyridine-3-carboxylic acid

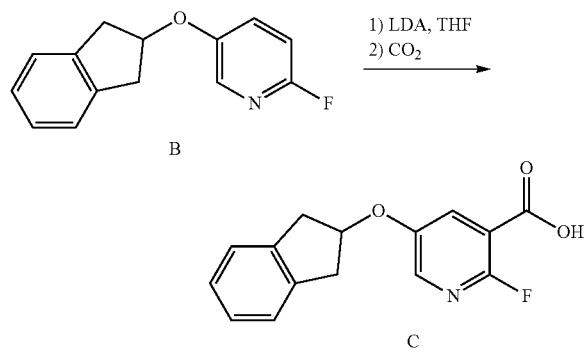

A 2.0M solution of lithium diisopropylamide (27.3 ml, 54.5 mmol) in THF was dropwise added at −78° C. to a solution of 2-fluoro-5-indan-2-yloxy-pyridine (5.0 g, 21.8 mmol) in anhydrous THF (100 ml). The reaction mixture was stirred at −78° C. for 15 mn, poured into a flask containing dry ice and temperature increased to 20° C. until end of gassing. Water was added (100 ml) and the organic solvents were evaporated under vacuum. 3N HCl (10 ml) was added to the residual mixture leading to a yellow precipitate. Acetone (100 ml) was added. The suspension was triturated, filtered off, washed with acetone and dried to obtain the expected product as a yellow solid (9.5 g, 53%). $^1$H NMR (300 MHz, DMSO-d$_6$) δ 13.67 (s, 1H), 8.09 (dd, J=3.1, 1.8 Hz, 1H), 7.87 (dd, J=7.7, 3.1 Hz, 1H), 7.26-7.23 (m, 2H), 7.17-7.14 (m, 2H), 5.35 (qt, J=3.7 Hz, 1H), 3.37 (dd, J=17.1, 5.9 Hz, 2H), 3.03 (dd, J=17.1, 2.0 Hz, 2H). ESIMS m/z [M+H]$^+$ 274.0.

Intermediate D: Ethyl 3-(2-fluoro-5-indan-2-yloxy-3-pyridyl)-3-oxo-propanoate

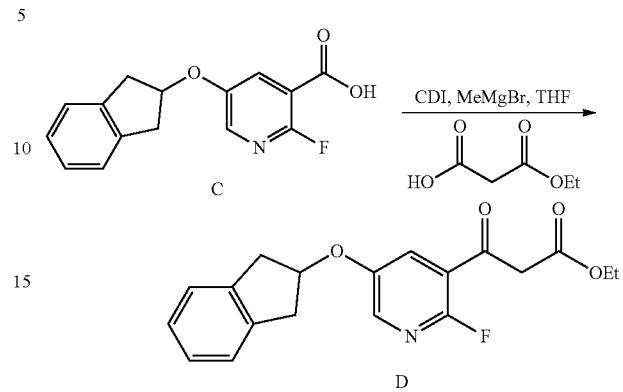

To a solution of 2-fluoro-5-indane-2-yloxy-pyridine-3-carboxylic acid (13.0 g, 47.6 mmol) in anhydrous THF (150 ml), was added 1,1-carbonyldiimidazole (9.3 g, 57.4 mmol). The mixture was stirred at 80° C. for 2 h (solution A). In parallel, ethyl hydrogen malonate (6.3 g, 47.7 mmol) was dissolved in anhydrous THF (150 ml) and methylmagnesium bromide (1.4 M, 54 ml, 75.6 mmol) was slowly added at 0° C. over 1 h. After 1 h at 0° C., solution A was added dropwise to the previous mixture (over 30 mn). The gummy suspension was then heated at 65° C. for 18 h. The hot mixture was poured slowly into water at 0° C. 6N HCl was added until pH=1. The aqueous layer was extracted with AcOEt (100 ml) and dichloromethane (2×100 ml). The combined organic layers were washed with brine (50 ml), dried over MgSO$_4$, filtered and concentrated. The crude obtained was purified by FC (340 g, SiO$_2$, cyclohexane/AcOEt 100:0→80:20) leading to the expected product (10.8 g, 66%) as a light brown oil. $^1$H NMR (300 MHz, DMSO-d$_6$) δ 8.17 (d, J=1.8 Hz, 1H), 7.95-7.91 (dd, J=7.8, 3.1 Hz, 1H), 7.29-7.26 (m, 2H), 7.20-7.16 (m, 2H), 5.40 (brs, 1H), 4.16-4.08 (m, 4H), 3.40 (dd, J=17.0, 5.9 Hz, 2H), 3.05 (d, J=17.0 Hz, 2H), 1.17 (t, J=7.1 Hz, 3H). ESIMS m/z [M+H]$^+$ 344.0.

Intermediate E: Ethyl 3-ethoxy-2-(2-fluoro-5-indan-2-yloxy-pyridine-3-carbonyl)prop-2-enoate

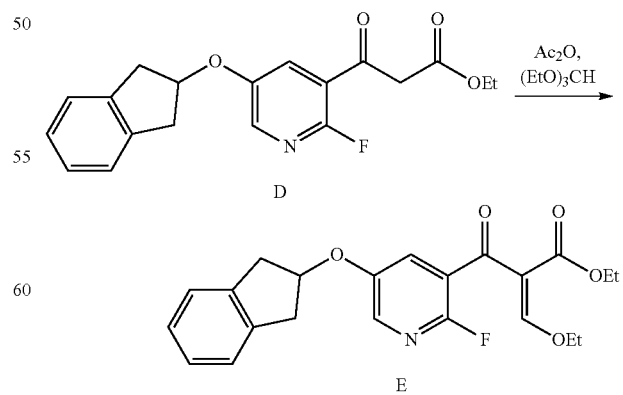

A mixture of ethyl 3-(2-fluoro-5-indan-2-yloxy-3-pyridyl)-3-oxo-propanoate (10.8 g, 31.4 mmol) acetic anhydride (7.4 ml, 78.3 mmol) and triethylorthoformate (7.8 ml, 46.9 mmol) was stirred under argon at 130° C. for 3 h. After cooling and evaporation of the solvents under vacuum, the crude was used without purification for the next step. ESIMS m/z [M+H]$^+$ 400.1.

Intermediate F: Ethyl 1-ethyl-6-indan-2-yloxy-4-oxo-1,8-naphthyridine-3-carboxylate

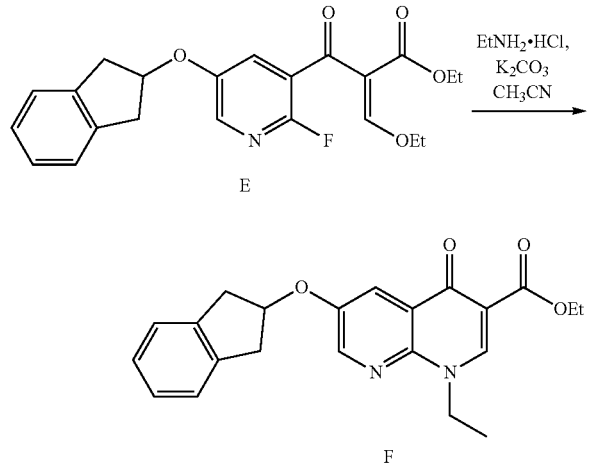

Crude ethyl 3-ethoxy-2-(2-fluoro-5-indan-2-yloxy-pyridine-3-carbonyl)prop-2-enoate (31.4 mmol) was suspended in acetonitrile (300 ml). Ethylamine hydrochloride (3.8 g, 46.6 mmol) and potassium carbonate (19.5 g, 141.1 mmol) were added at RT. The mixture obtained was stirred at 80° C. for 16 h. After cooling and filtration, the filtrate was evaporated to dryness. Water was added (100 ml) and the residual solid was triturated, filtered off, washed with water and dried under reduced pressure to obtain the expected product as a beige solid (11.0 g, 92%). $^1$H NMR (300 MHz, DMSO-d$_6$) δ 8.82 (s, 1H), 8.56 (d, J=2.2 Hz, 1H), 8.03 (d, J=3.1 Hz, 1H), 7.30-7.27 (m, 2H), 7.20-7.17 (m, 2H), 5.50-5.40 (m, 1H), 4.48 (qd, J=6.8 Hz, 2H), 4.24 (qd, J=7.0 Hz, 2H), 3.44 (dd, J=17.0, 5.8 Hz, 2H), 3.09 (d, J=17.0 Hz, 2H), 1.36 (t, J=7.0 Hz, 3H), 1.30 (t, J=7.1 Hz, 3H). ESIMS m/z [M+H]$^+$ 379.1.

Intermediate G: 1-Ethyl-6-indan-2-yloxy-4-oxo-1,8-naphthyridine-3-carboxylic acid

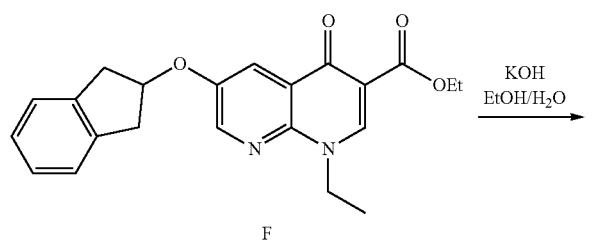

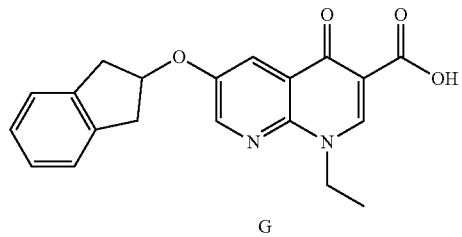

A solution of potassium hydroxide (2.7 g, 48.1 mmol) in water (20 ml) was added to a suspension of ethyl 1-ethyl-6-indan-2-yloxy-4-oxo-1,8-naphthyridine-3-carboxylate (9.0 g, 23.8 mmol) in ethanol (200 ml). The mixture was stirred at 80° C. for 2 h. After cooling and evaporation of the solvent, HCl 1N (200 ml) was added. The suspension obtained was filtered off, washed with water (50 ml), and dried under reduced pressure to obtain the expected product as a pink powder (7.5 g, 90%). $^1$H NMR (300 MHz, DMSO-d$_6$) δ 14.95 (s, 1H), 9.17 (s, 1H), 8.73 (d, J=3.1 Hz, 1H), 8.13 (d, J=3.1 Hz, 1H), 7.30-7.27 (m, 2H), 7.20-7.17 (m, 2H), 5.53 (brs, 1H), 4.65 (qd, J=6.8 Hz, 2H), 3.47 (dd, J=17.2, 5.8 Hz, 2H), 3.12 (d, J=17.2 Hz, 2H), 1.41 (t, J=7.1 Hz, 3H). ESIMS m/z [M+H]$^+$ 351.1.

Intermediate I: 5-Chloro-2-indan-2-yloxy-pyridine

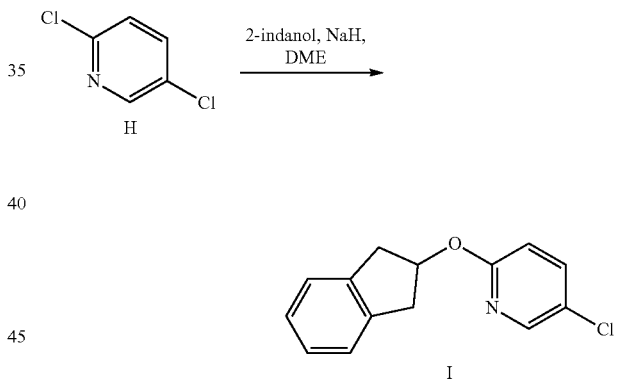

To a suspension of sodium hydride (60% dispersion in mineral oil, 4.50 g, 111 mmol) in DME (400 ml) was added 2-indanol (14.9 g, 111 mmol) at 0° C. The solution was stirred at 0° C. for 30 mn before addition of 2,5-dichloropyridine (15.0 g, 101 mmol). The reaction mixture was heated at 80° C. for 18 h. After cooling, water (100 ml) was added. The organic solvent was removed by evaporation under reduced pressure. The remaining aqueous layer was extracted with dichloromethane (2×100 ml). The combined organic fractions were dried over MgSO$_4$, filtered off and concentrated under vacuum. The crude was purified by FC (340 g, SiO$_2$, cyclohexane/CH$_2$Cl$_2$ 100:0→20:80) leading to the expected product as a beige solid (17.7 g, 71%). $^1$H NMR (300 MHz, DMSO-d$_6$) δ 8.24 (d, J=2.6 Hz, 1H), 7.78 (dd, J=8.9, 2.8 Hz, 1H), 7.27-7.23 (m, 2H), 7.19-7.15 (m, 2H), 7.80 (d, J=8.9 Hz, 1H), 5.72-5.66 (m, 1H), 3.37 (dd, J=17.1, 6.0 Hz, 2H), 3.01 (dd, J=17.1, 2.5 Hz, 2H). ESIMS m/z [M+H]$^+$ 245.9.

Intermediate J: 5-Chloro-2-indane-2-yloxy-pyridine-4-carboxylic acid

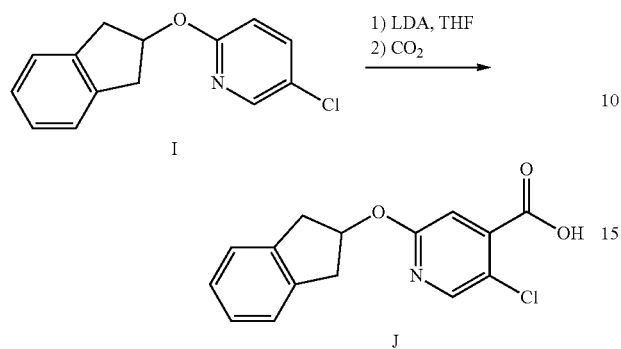

A 2.0M solution of lithium diisopropylamide (45 ml, 90 mmol) in THF was dropwise added at −78° C. to a solution of 5-chloro-2-indan-2-yloxy-pyridine (10.1 g, 41.1 mmol) in anhydrous THF (200 ml). The reaction mixture was stirred at −78° C. for 2 h, then pieces of dry-ice were added and the stirring was maintained until the end of the gassing. The mixture was poured into water (100 ml). The organic solvents were evaporated under vacuum and 3N HCl (30 ml) was added. The suspension formed was filtered off, washed with water and triturated in methanol. After a new filtration and drying, the expected product was isolated as a white powder (6.0 g, 50%). $^1$H NMR (300 MHz, DMSO-$d_6$) δ 14.04 (s, 1H), 8.36 (s, 1H), 7.27-7.25 (m, 2H), 7.18-7.15 (m, 2H), 7.04 (s, 1H), 5.71 (brs, 1H), 3.38 (dd, J=17.0, 6.0 Hz, 2H), 3.02 (d, J=17.0 Hz, 2H). ESIMS m/z [M+H]$^+$ 290.0.

Intermediate K: Ethyl 3-(5-chloro-2-indan-2-yloxy-4-pyridyl)-3-hydroxy-prop-2-enoate

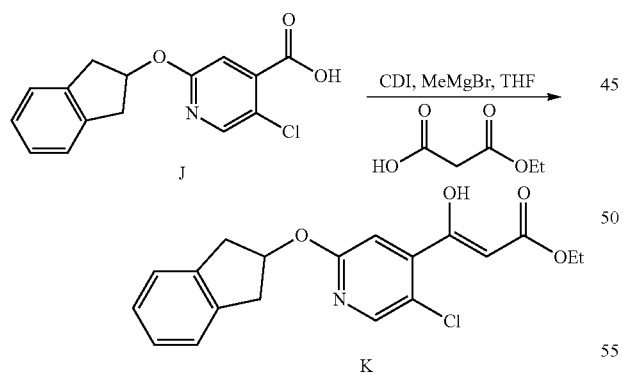

To a solution of 5-chloro-2-indane-2-yloxy-pyridine-4-carboxylic acid (6.8 g, 23.5 mmol) in anhydrous THF (100 ml), was added 1,1-carbonyldiimidazole (4.6 g, 28.4 mmol). The mixture was stirred at 80° C. for 2 h (solution A). In parallel, ethyl hydrogen malonate (3.1 g, 23.5 mmol) was dissolved in anhydrous THF (50 ml) and methylmagnesium bromide (1.4 M, 27 ml, 37.8 mmol) was slowly added at 0° C. over 45 mn. After 2 h at 0° C., solution A was added dropwise to the previous mixture (over 30 mn). The gummy suspension was then heated at 70° C. for 18 h. The hot mixture was poured slowly into water at 0° C. 6N HCl was added until pH=1. The aqueous layer was extracted with AcOEt (100 ml) and dichloromethane (2×100 ml). The combined organic layers were washed with brine (50 ml), dried over MgSO$_4$, filtered and concentrated. The crude obtained was purified by FC (120 g, SiO$_2$, cyclohexane/AcOEt 100:0→80:20) leading to the expected product (3.7 g, 43%) as an orange powder. $^1$H NMR (300 MHz, CHCl$_3$-d) δ 12.38 (s, 1H), 8.21 (s, 1H), 7.27-7.17 (m, 4H), 6.92 (s, 1H), 5.80-5.70 (m, 1H), 5.63 (s, 1H), 4.29 (qd, J=7.1 Hz, 2H), 3.41 (dd, J=16.9, 6.3 Hz, 2H), 3.12 (dd, J=16.9, 3.1 Hz, 2H), 1.33 (t, J=7.1 Hz, 3H). ESIMS m/z [M+H]$^+$ 360.0.

Intermediate L: Ethyl 2-(5-chloro-2-indan-2-yloxy-pyridine-4-carbonyl)-3-ethoxy-prop-2-enoate

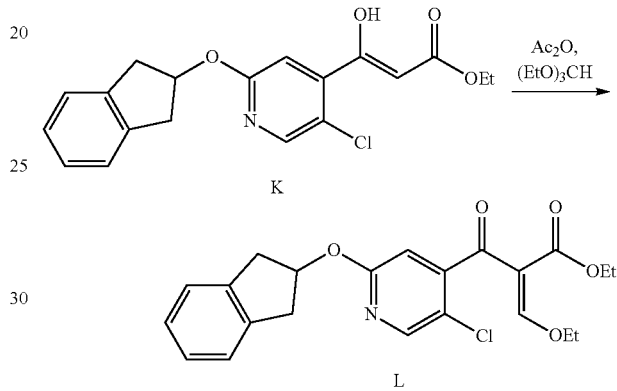

A mixture of ethyl 3-(5-chloro-2-indan-2-yloxy-4-pyridyl)-3-hydroxy-prop-2-enoate (3.7 g, 10.2 mmol), acetic anhydride (2.4 ml, 25.5 mmol) and triethylorthoformate (2.5 ml, 15.3 mmol) was stirred under argon at 130° C. for 3 h. After cooling and evaporation of the solvents under vacuum, the crude was used without purification for the next step.

Intermediate M: Ethyl 2-(5-chloro-2-indan-2-yloxy-pyridine-4-carbonyl)-3-(ethylamino) prop-2-enoate

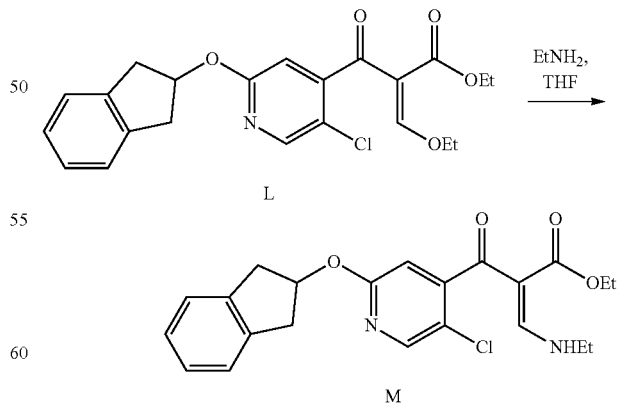

To crude ethyl 2-(5-chloro-2-indan-2-yloxy-pyridine-4-carbonyl)-3-ethoxy-prop-2-enoate (10.2 mmol) in THF (80 ml) was added dropwise 2M ethylamine in THF (10.1 ml, 20.4 mmol). The reaction mixture was stirred at RT for 2 h and evaporated to dryness. Dichloromethane (50 ml) and water (20 ml) were added. The organic layer was washed with brine (20 ml), dried over MgSO₄, filtered and concentrated. The brown oil recovered was corresponding to the expected product (4.6 g). ¹H NMR (300 MHz, DMSO-d₆) δ 10.92-10.80 (m, 1H), 8.21-8.16 (m, 2H), 7.27-7.24 (m, 2H), 7.18-7.15 (m, 2H), 6.57 (s, 1H), 5.72-5.69 (m, 1H), 3.87 (qd, J=7.1 Hz, 2H), 3.50 (qt, J=6.8 Hz, 2H), 3.37 (dd, J=17.1, 6.1 Hz, 2H), 3.01 (dd, J=17.0, 2.4 Hz, 2H), 1.20 (t, J=7.1 Hz, 3H), 0.92 (t, J=7.1 Hz, 3H). ESIMS m/z [M+H]⁺ 415.0.

Intermediate N: Ethyl 1-ethyl-6-indan-2-yloxy-4-oxo-1,7-naphthyridine-3-carboxylate

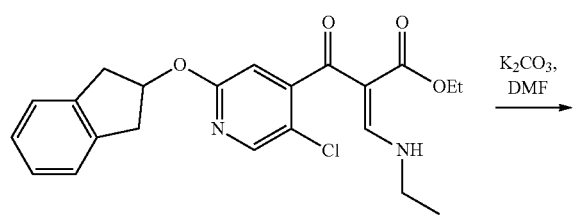

Crude ethyl 2-(5-chloro-2-indan-2-yloxy-pyridine-4-carbonyl)-3-ethoxy-prop-2-enoate (10.2 mmol) and potassium carbonate (4.25 g, 30.7 mmol) were suspended in DMF (30 ml) and heated under microwave at 160° C. for 2 h. After cooling and evaporation of the solvent, water (100 ml) and ethyl acetate (100 ml) were added to the residue. The aqueous layer was extracted with AcOEt (2×50 ml). The combined organic layers were washed with brine (50 ml), dried over MgSO₄, filtered and concentrated. The crude obtained was purified by FC (120 g, SiO₂, cyclohexane/AcOEt 100:0→0:100) leading to the expected product (475 mg, 23%) as a brown powder. ¹H NMR (300 MHz, DMSO-d₆) δ 8.98 (s, 1H), 8.67 (s, 1H), 7.30 (s, 1H), 7.27-7.24 (m, 2H), 7.17-7.15 (m, 2H), 5.78-5.71 (m, 1H), 4.47 (qd, J=7.1 Hz, 2H), 4.20 (qd, J=7.1 Hz, 2H), 3.41 (dd, J=17.0, 6.1 Hz, 2H), 3.05 (dd, J=17.0, 2.3 Hz, 2H), 1.39 (t, J=7.0 Hz, 3H), 1.26 (t, J=7.1 Hz, 3H). ESIMS m/z [M+H]⁺ 379.1.

Intermediate O: 1-Ethyl-6-indan-2-yloxy-4-oxo-1,7-naphthyridine-3-carboxylic acid

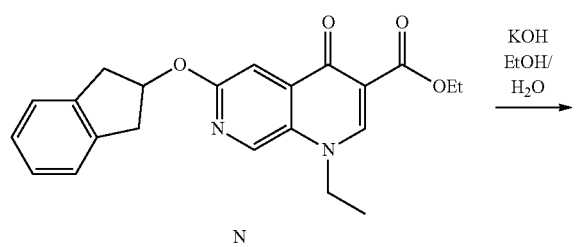

A solution of potassium hydroxide (165 mg, 2.93 mmol) in water (1.1 ml) was added to a suspension of ethyl 1-ethyl-6-indan-2-yloxy-4-oxo-1,7-naphthyridine-3-carboxylate (555 mg, 1.47 mmol) in ethanol (11 ml). The mixture was stirred at RT for 18 h. After evaporation of the solvent, HCl 1N (20 ml) was added. The suspension obtained was filtered off, washed with ethanol and Et₂O, and dried under reduced pressure to recover the expected product as a beige powder (500 mg, 97%). ESIMS m/z [M+H]⁺ 351.0.

Intermediate Q: 6-Chloro-1-ethyl-4-oxo-1,7-naphthyridine-3-carboxylic acid

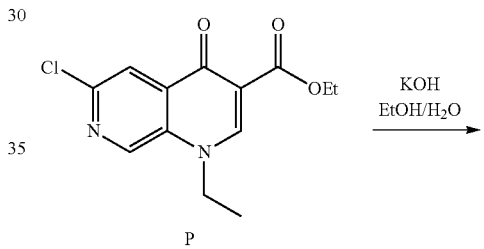

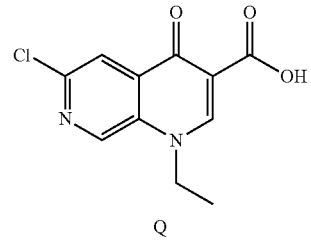

A solution of potassium hydroxide (200 mg, 3.56 mmol) in water (7 ml) was added to a suspension of ethyl 6-chloro-1-ethyl-4-oxo-1,7-naphthyridine-3-carboxylate (500 mg, 1.78 mmol) in ethanol (15 ml). The mixture was stirred at RT for 18 h. After evaporation of the solvent, HCl 1N (20 ml) was added. The suspension obtained was filtered off, washed with ethanol and Et₂O, and dried under reduced pressure to recover the expected product as a pink powder (417 mg, 93%). ¹H NMR (300 MHz, DMSO-d₆) δ 14.27 (s, 1H), 9.37 (s, 1H), 9.12 (s, 1H), 8.18 (d, J=0.5 Hz, 1H), 4.68 (qd, J=7.1 Hz, 2H), 1.43 (t, J=7.1 Hz, 3H).

Intermediate R: 6-Chloro-1-ethyl-3-(morpholine-4-carbonyl)-1,7-naphthyridin-4-one

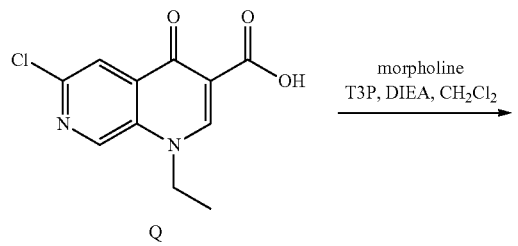

6-Chloro-1-ethyl-4-oxo-1,7-naphthyridine-3-carboxylic acid (415 mg, 1.60 mmol), morpholine (0.20 ml, 2.20 mmol), propylphosphonic anhydride solution 50 wt. % in ethyl acetate (1.50 ml, 2.40 mmol) and diisopropylethylamine (0.87 ml, 5.10 mmol) were reacted as described under General Procedure A (18 h at RT) to furnish the title compound (325 mg, 65%) as a yellow solid. $^1$H NMR (300 MHz, CHCl$_3$-d) δ 8.81 (s, 1H), 8.27 (s, 1H), 8.08 (s, 1H), 4.32 (qd, J=7.3 Hz, 2H), 3.78 (brs, 6H), 3.39 (brs, 2H), 1.61 (t, J=7.3 Hz, 3H). ESIMS m/z [M+H]$^+$ 321.1.

Intermediate S: 6-Chloro-1-ethyl-3-(3-oxa-8-azabicyclo[3.2.1]octane-8-carbonyl)-1,7-naphthyridin-4-one

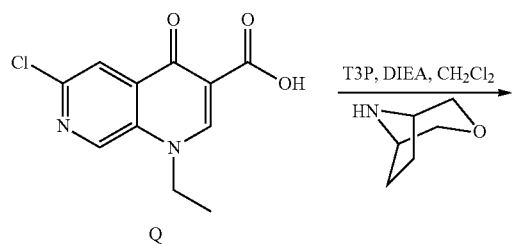

6-Chloro-1-ethyl-4-oxo-1,7-naphthyridine-3-carboxylic acid (100 mg, 0.40 mmol), 3-oxa-8-azabicyclo[3.2.1]octane hydrochloride (77 mg, 0.52 mmol), propylphosphonic anhydride solution 50 wt. % in ethyl acetate (0.35 ml, 0.59 mmol) and diisopropylethylamine (0.21 ml, 1.19 mmol) were reacted as described under General Procedure A (18 h at RT) to furnish the title compound (132 mg, 96%) as a white solid. $^1$H NMR (300 MHz, DMSO-d$_6$) δ 9.18 (s, 1H), 8.49 (s, 1H), 8.05 (s, 1H), 4.51 (brs, 1H), 4.49 (qd, J=7.0 Hz, 2H), 3.80 (brs, 1H), 3.63 (d, J=10.5 Hz, 1H), 3.62 (s, 2H), 3.47 (d, J=10.5 Hz, 1H), 1.95-1.80 (m, 4H), 1.40 (t, J=7.1 Hz, 3H).

Intermediate T: 6-Chloro-1-ethyl-3-(8-oxa-3-azabicyclo[3.2.1]octane-3-carbonyl)-1,7-naphthyridin-4-one

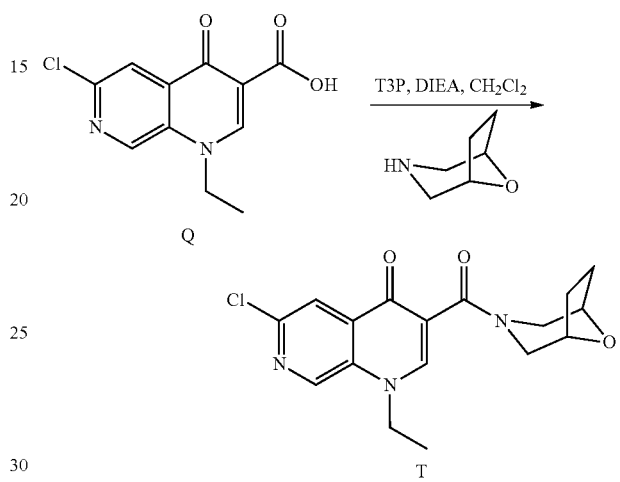

6-Chloro-1-ethyl-4-oxo-1,7-naphthyridine-3-carboxylic acid (400 mg, 1.58 mmol), 8-oxa-3-azabicyclo[3.2.1]octane hydrochloride (308 mg, 2.05 mmol), propylphosphonic anhydride solution 50 wt. % in ethyl acetate (1.40 ml, 2.37 mmol) and diisopropylethylamine (1.10 ml, 6.30 mmol) were reacted as described under General Procedure A (20 h at RT) to furnish the title compound (410 mg, 75%) as a yellow-brown foam. $^1$H NMR (300 MHz, DMSO-d$_6$) δ 9.16 (s, 1H), 8.40 (s, 1H), 8.01 (s, 1H), 4.45 (qd, J=7.1 Hz, 2H), 4.35 (d, J=5.9 Hz, 1H), 4.16 (d, J=5.7 Hz, 1H), 4.10 (d, J=13.3 Hz, 1H), 3.30-3.12 (m, 2H), 2.91 (d, J=11.7 Hz, 1H), 1.97-1.65 (m, 4H), 1.37 (t, J=7.0 Hz, 3H).

Intermediate V: Ethyl 2-(3,6-dichloropyridazine-2-carbonyl)-3-(dimethylamino)prop-2-enoate

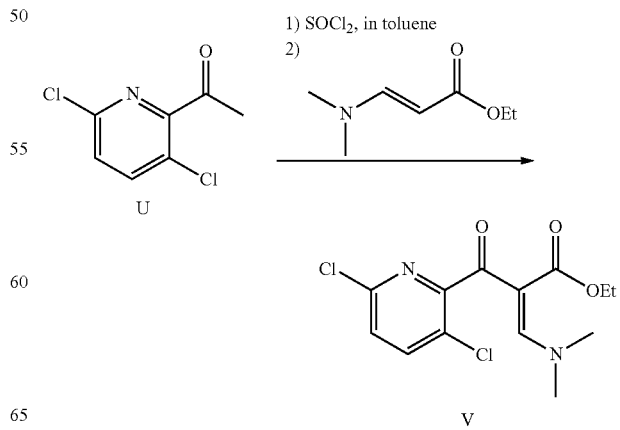

A mixture of 3,6-dichloropyridine-2-carboxylic acid (4.0 g, 20.8 mmol), thionyl chloride (10 ml, 137 mmol), DMF (0.5 ml, 6.5 mmol) and toluene (50 ml) was stirred in a sealed tube at 80° C. for 3 h. After cooling and evaporation of the solvents, the residue was dissolved in dry THF (20 ml) and added to a mixture of ethyl-3-dimethylaminoacrylate (3.3 g, 23.0 mmol) and triethylamine (4.0 ml, 28.7 mmol) in dry THF (20 ml). The mixture formed was stirred in a sealed tube at 70° C. for 18 h. After evaporation of the solvents, the crude obtained was used directly for next step (8.9 g) as a brown oil. ESIMS m/z [M+H]$^+$ 317.0.

Intermediate W: Ethyl 2-(3,6-dichloropyridine-2-carbonyl)-3-(ethylamino)prop-2-enoate

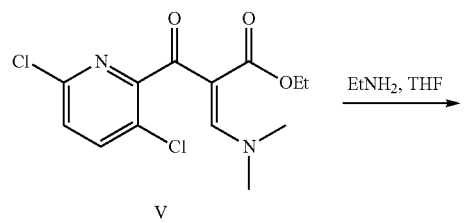

V

EtNH$_2$, THF

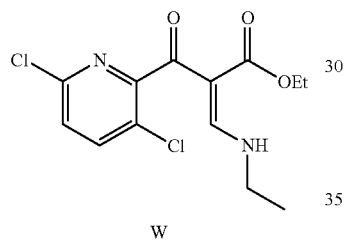

W

Crude ethyl 2-(3,6-dichloropyridazine-2-carbonyl)-3-(dimethylamino)prop-2-enoate (20.8 mmol) in a solution of 2M ethylamine in methanol (30.0 ml, 60.0 mmol) was stirred at RT for 1 h. The precipitate formed was filtered off, washed with methanol and Et$_2$O, and dried under reduced pressure to obtain the expected product as a white powder (4.7 g, 72% over 2 steps). $^1$H NMR (300 MHz, DMSO-d$_6$) δ 11.05 (brs, 1H), 8.18 (d, J=14.2 Hz, 1H), 8.18 (d, J=8.4 Hz, 1H), 7.24 (d, J=8.6 Hz, 1H), 3.97 (qd, J=7.1 Hz, 2H), 3.52 (qt, J=7.2 Hz, 2H), 1.36 (t, J=7.3 Hz, 3H), 0.97 (t, J=7.1 Hz, 3H). ESIMS m/z [M+H]$^+$ 317.0.

Intermediate X: Ethyl 6-chloro-1-ethyl-4-oxo-1,5-naphthyridine-3-carboxylate

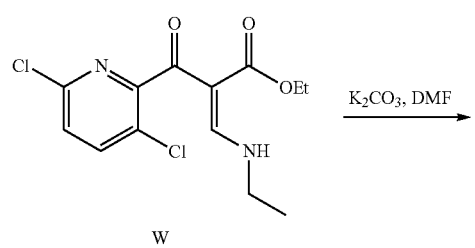

W

K$_2$CO$_3$, DMF

-continued

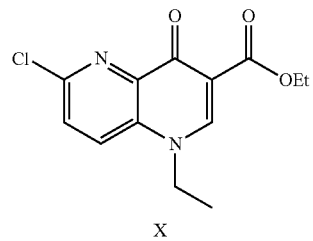

X

Ethyl 2-(3,6-dichloropyridine-2-carbonyl)-3-(ethylamino)prop-2-enoate (4.7 g, 14.8 mmol) and potassium carbonate (6.0 g, 43.4 mmol) were suspended in DMF (50 ml) and heated at 130° C. for 18 h. After cooling and evaporation of the solvent, the residue was triturated in dichloromethane (100 ml) and filtered off. The filtrate was concentrated in vacuo and triturated in methanol. The solid recovered after filtration was dried, leading to the expected product (2.17 g, 55%) as a white solid. $^1$H NMR (300 MHz, DMSO-d$_6$) δ 8.71 (s, 1H), 8.41 (d, J=9.0 Hz, 1H), 7.87 (d, J=9.0 Hz, 1H), 4.41 (qd, J=7.0 Hz, 2H), 4.24 (qd, J=7.1 Hz, 2H), 1.34 (t, J=7.1 Hz, 3H), 1.29 (t, J=7.1 Hz, 3H). ESIMS m/z [M+H]$^+$ 280.9.

Intermediate Y: 6-Chloro-1-ethyl-4-oxo-1,5-naphthyridine-3-carboxylic acid

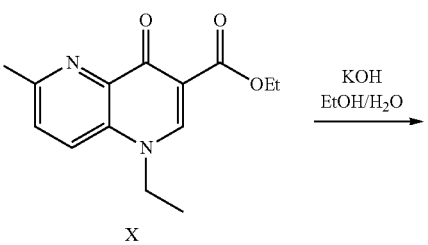

X

KOH
EtOH/H$_2$O

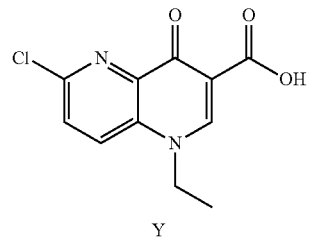

Y

A solution of potassium hydroxide (530 mg, 9.4 mmol) in water (20 ml) was added to a suspension of ethyl 6-chloro-1-ethyl-4-oxo-1,5-naphthyridine-3-carboxylate (1.78 g, 6.3 mmol) in ethanol (60 ml). The mixture was stirred at RT for 3 h. After evaporation of the solvent, HCl 1N (20 ml) was added. The suspension obtained was filtered off, washed with ethanol and Et$_2$O, and dried under reduced pressure to recover the expected product as a pale yellow powder (1.20 g, 75%). $^1$H NMR (300 MHz, DMSO-d$_6$) δ 15.02 (s, 1H), 9.12 (s, 1H), 8.62 (d, J=9.1 Hz, 1H), 8.04 (d, J=9.1 Hz, 1H), 4.61 (qd, J=7.1 Hz, 2H), 1.39 (t, J=7.1 Hz, 3H). ESIMS m/z [M+H]$^+$ 252.9.

Intermediate Z: 6-Chloro-1-ethyl-3-(morpholine-4-carbonyl)-1,5-naphthyridin-5-one

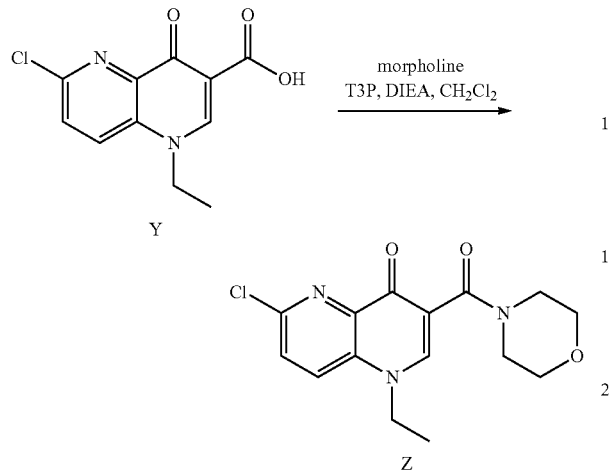

6-Chloro-1-ethyl-4-oxo-1,5-naphthyridine-3-carboxylic acid (380 mg, 1.50 mmol), morpholine (0.39 ml, 4.50 mmol), propylphosphonic anhydride solution 50 wt. % in ethyl acetate (1.78 ml, 3.00 mmol) and diisopropylethylamine (1.31 ml, 7.50 mmol) were reacted as described under General Procedure A (18 h at RT) to furnish the title compound (640 mg, 91%) as a brown foam. $^1$H NMR (300 MHz, DMSO-$d_6$) δ 8.39 (d, J=9.0 Hz, 1H), 8.33 (s, 1H), 7.84 (d, J=9.0 Hz, 1H), 4.34 (qd, J=7.0 Hz, 2H), 3.60-3.54 (m, 6H), 3.24 (brs, 2H), 1.31 (t, J=7.0 Hz, 3H). ESIMS m/z [M+H]$^+$ 322.0.

Intermediate AA: 6-Chloro-1-ethyl-3-[(1R,4R)-2-oxa-5-azabicyclo[2.2.1]heptane-5-carbonyl]-1,5-naphthyridin-4-one

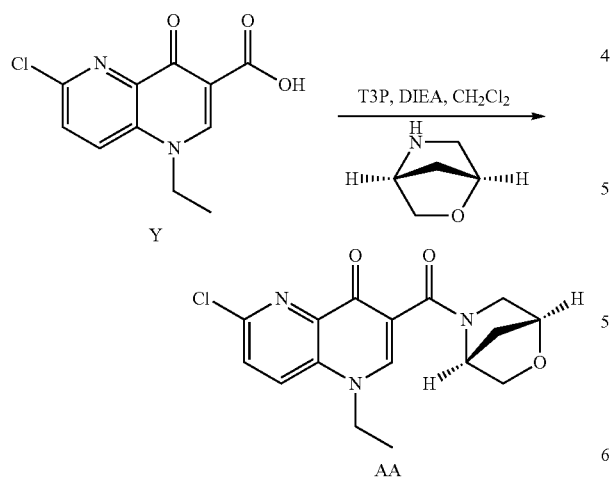

6-Chloro-1-ethyl-4-oxo-1,5-naphthyridine-3-carboxylic acid (450 mg, 1.78 mmol), (1R,4R)-2-oxa-5-azabicyclo[2.2.1]heptane hydrochloride (240 mg, 1.77 mmol), propylphosphonic anhydride solution 50 wt. % in ethyl acetate (1.60 ml, 2.69 mmol) and diisopropylethylamine (1.30 ml, 7.46 mmol) were reacted as described under General Procedure A (18 h at RT) to furnish the title compound (189 mg, 32%) as a yellow solid. ESIMS m/z [M+H]$^+$ 334.0.

Intermediate AB: 6-Chloro-1-ethyl-3-(8-oxa-3-azabicyclo[3.2.1]octane-3-carbonyl)-1,5-naphthyridin-4-one

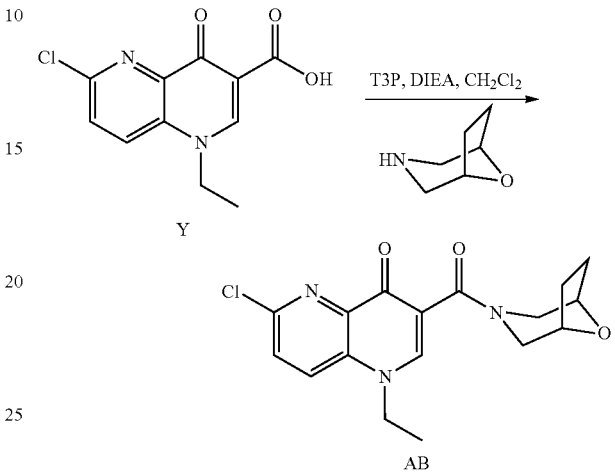

6-Chloro-1-ethyl-4-oxo-1,5-naphthyridine-3-carboxylic acid (450 mg, 1.78 mmol), 8-oxa-3-azabicyclo[3.2.1]octane hydrochloride (260 mg, 1.74 mmol), propylphosphonic anhydride solution 50 wt. % in ethyl acetate (1.60 ml, 2.69 mmol) and diisopropylethylamine (1.30 ml, 7.46 mmol) were reacted as described under General Procedure A (18 h at RT) to furnish the title compound (400 mg, 65%) as a yellow foam. $^1$H NMR (300 MHz, CHCl$_3$-d) δ 8.03 (s, 1H), 7.84 (d, J=9.0 Hz, 1H), 7.61 (d, J=9.0 Hz, 1H), 4.44 (brs, 1H), 4.34-4.19 (m, 4H), 3.49 (d, J=12.7 Hz, 1H), 3.34 (d, J=12.7 Hz, 1H), 3.16 (d, J=13.2 Hz, 1H), 3.36-3.25 (m, 1H), 2.00-1.79 (m, 3H), 1.53 (t, J=7.3 Hz, 3H). ESIMS m/z [M+H]$^+$ 348.0.

Intermediate AC: 6-Chloro-1-ethyl-3-(3-oxa-7-azabicyclo[3.3.1]nonane-7-carbonyl)-1,5-naphthyridin-4-one

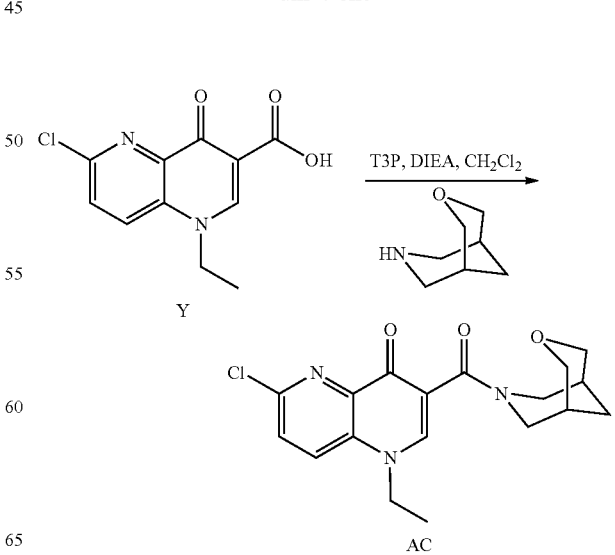

6-Chloro-1-ethyl-4-oxo-1,5-naphthyridine-3-carboxylic acid (500 mg, 1.98 mmol), 3-oxa-7-azabicyclo[3.3.1]nonane (250 mg, 1.97 mmol), propylphosphonic anhydride solution 50 wt. % in ethyl acetate (1.80 ml, 3.02 mmol) and diisopropylethylamine (1.40 ml, 8.04 mmol) were reacted as described under General Procedure A (18 h at RT) to furnish the title compound (650 mg, 91%) as a yellow oil. ESIMS m/z [M+H]+ 362.0.

Intermediate AE: Ethyl 2-(3,6-dichloropyridazine-4-carbonyl)-3-(dimethylamino)prop-2-enoate

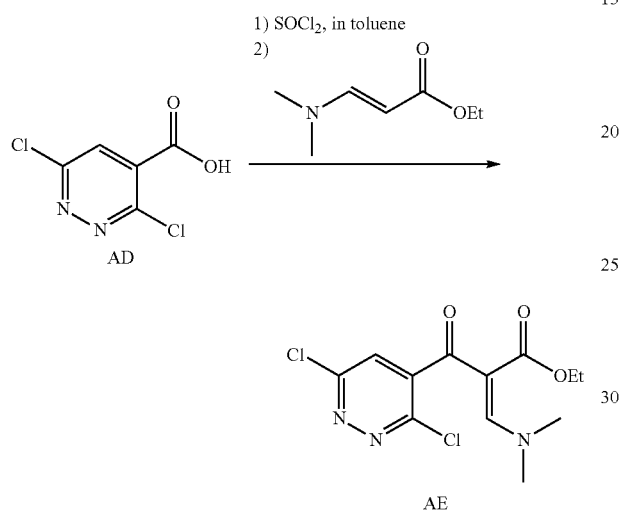

AD

AE

A mixture of 3,6-dichloropyridazine-4-carboxylic acid (5.3 g, 27.5 mmol), thionyl chloride (10 ml, 137 mmol), DMF (0.5 ml, 6.5 mmol) and toluene (50 ml) was stirred in a sealed tube at 110° C. for 3 h. After cooling and evaporation of the solvents, the residue was dissolved in dry THF (20 ml) and added to a mixture of ethyl-3-dimethylamino-acrylate (4.3 g, 30.0 mmol) and triethylamine (4.6 ml, 33.0 mmol) in dry THF (20 ml). The mixture formed was stirred in a sealed tube at 75° C. for 8 h. After evaporation of the solvents, the crude obtained was purified by FC (120 g, SiO$_2$, CH$_2$Cl$_2$/AcOEt 100:0→70:30) leading to the expected product (5.8 g, 66%) as a brown oil. $^1$H NMR (300 MHz, DMSO-d$_6$) δ 8.11 (s, 1H), 8.00 (s, 1H), 3.90 (qd, J=7.1 Hz, 2H), 3.46 (s, 3H), 3.01 (s, 3H), 0.93 (t, J=7.1 Hz, 3H). ESIMS m/z [M+H]+ 318.0.

Intermediate AF: Ethyl 3-chloro-8-ethyl-5-oxo-pyrido[2,3-c]pyridazine-6-carboxylate

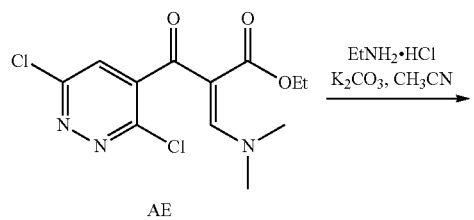

AE

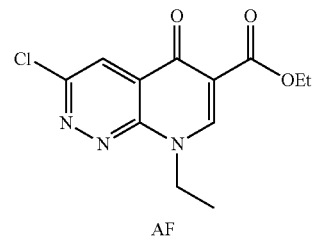

AF

Crude ethyl 2-(3,6-dichloropyridazine-4-carbonyl)-3-(dimethylamino)prop-2-enoate (5.2 g, 16.4 mmol) was suspended in acetonitrile (130 ml). Ethylamine hydrochloride (2.0 g, 24.7 mmol) and potassium carbonate (6.8 g, 49.4 mmol) were added at RT. The mixture obtained was stirred at RT for 1 h and at 80° C. for 18 h. After cooling and filtration (washing with dichloromethane), the filtrate was evaporated to dryness. The residue obtained was triturated in AcOEt and filtered off, leading after drying to the expected product as a yellow powder (3.3 g, 71%). $^1$H NMR (300 MHz, DMSO-d$_6$) δ 8.99 (s, 1H), 8.34 (s, 1H), 4.62 (qd, J=7.1 Hz, 2H), 4.23 (qd, J=7.0 Hz, 2H), 1.41 (t, J=7.0 Hz, 3H), 1.26 (t, J=7.1 Hz, 3H). ESIMS m/z [M+H]+ 282.0.

Intermediate AG: 3-Chloro-8-ethyl-5-oxo-pyrido[2,3-c]pyridazine-6-carboxylic acid

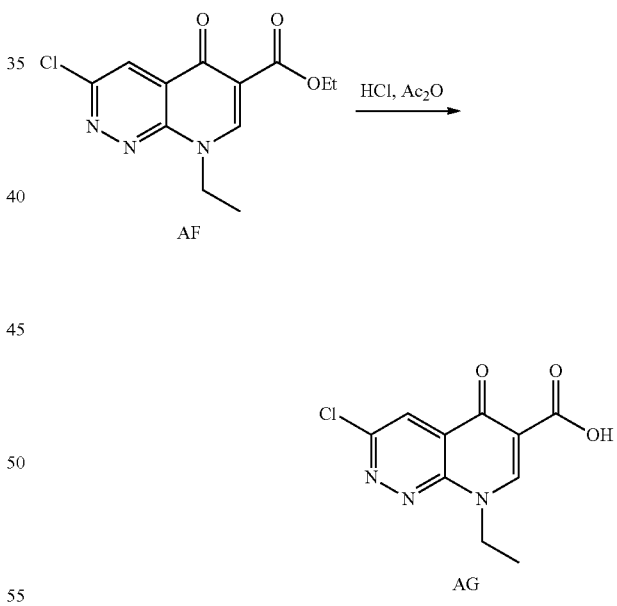

A concentrated solution of hydrogen chloride (37% in water, 1.5 ml) was added dropwise to acetic anhydride (5.0 ml) at 0° C. This solution was then poured onto ethyl 3-chloro-8-ethyl-5-oxo-pyrido[2,3-c]pyridazine-6-carboxylate (395 mg, 1.40 mmol). The mixture was stirred at 90° C. for 4 h. After cooling, the solvent was removed in vacuo leading to the expected product as a dark green solid (360 mg, quantitative). $^1$H NMR (300 MHz, DMSO-d$_6$) δ 13.52 (s, 1H), 9.29 (s, 1H), 8.59 (s, 1H), 4.75 (qd, J=6.8 Hz, 2H), 1.45 (t, J=6.9 Hz, 3H). ESIMS m/z [M+H]+ 253.9.

Intermediate AH: 3-Chloro-8-ethyl-6-(morpholine-4-carbonyl)pyrido[2,3-c]pyridazin-5-one

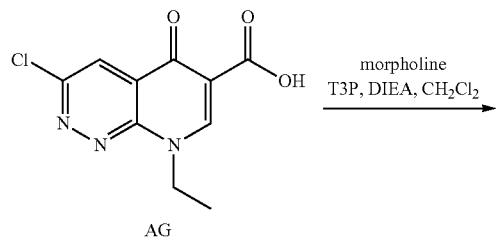

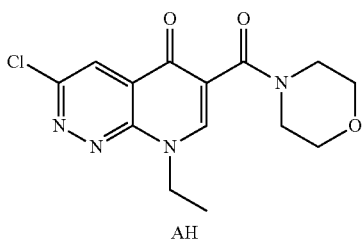

3-Chloro-8-ethyl-5-oxo-pyrido[2,3-c]pyridazine-6-carboxylic acid (1.0 g, 3.94 mmol), morpholine (0.70 ml, 7.88 mmol), propylphosphonic anhydride solution 50 wt. % in ethyl acetate (7.0 ml, 11.8 mmol) and diisopropylethylamine (2.75 ml, 15.6 mmol) were reacted as described under General Procedure A (18 h at RT) to furnish the title compound (1.17 g, 92%) as a yellow powder. $^1$H NMR (300 MHz, DMSO-$d_6$) δ 8.62 (s, 1H), 8.37 (s, 1H), 8.08 (s, 1H), 4.58 (qd, J=7.1 Hz, 2H), 3.61-3.50 (m, 6H), 3.27 (brs, 2H), 1.41 (t, J=7.0 Hz, 3H). ESIMS m/z [M+H]$^+$ 323.0.

Intermediate AI: 3-Chloro-8-ethyl-6-[(2R)-2-methylmorpholine-4-carbonyl]pyrido[2,3-c]pyridazin-5-one

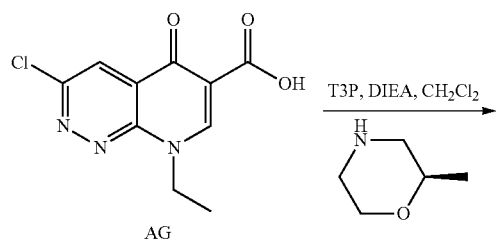

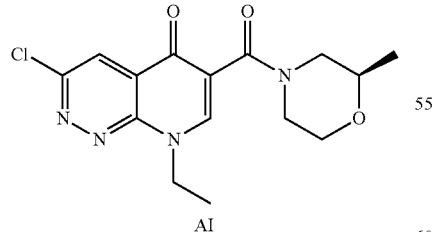

3-Chloro-8-ethyl-5-oxo-pyrido[2,3-c]pyridazine-6-carboxylic acid (350 mg, 1.38 mmol), (2R)-2-methylmorpholine hydrochloride (208 mg, 1.52 mmol), propylphosphonic anhydride solution 50 wt. % in ethyl acetate (1.60 ml, 2.76 mmol) and diisopropylethylamine (1.20 ml, 6.90 mmol) were reacted as described under General Procedure A (18 h at RT) to furnish the title compound (400 mg, 86%) as a yellow powder. $^1$H NMR (300 MHz, DMSO-$d_6$) δ 8.61 (s, 1H), 8.38 (s, 1H), 4.58 (qd, J=7.1 Hz, 2H), 4.29 (t, J=9.0 Hz, 1H), 3.90-3.40 (m, 4H), 3.14-2.72 (m, 2H), 1.41 (t, J=7.1 Hz, 3H), 1.12 and 0.95 (2d, J=6.2 Hz, 3H). ESIMS m/z [M+H]$^+$ 337.0.

Intermediate AJ: 3-Chloro-8-ethyl-6-[(2R)-2-isopropylmorpholine-4-carbonyl]pyrido[2,3-c]pyridazin-5-one

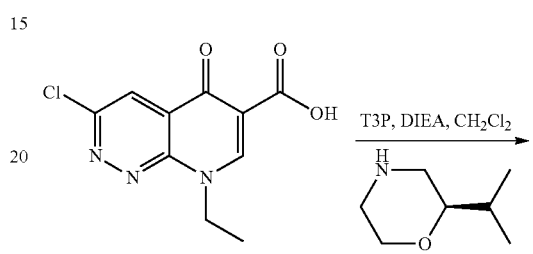

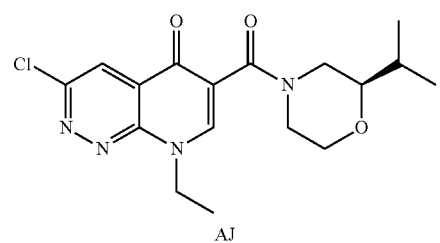

3-Chloro-8-ethyl-5-oxo-pyrido[2,3-c]pyridazine-6-carboxylic acid (470 mg, 1.86 mmol), (2R)-2-isopropylmorpholine (200 mg, 1.55 mmol), propylphosphonic anhydride solution 50 wt. % in ethyl acetate (1.30 ml, 3.87 mmol) and diisopropylethylamine (1.00 ml, 5.42 mmol) were reacted as described under General Procedure A (18 h at RT) to furnish the title compound (457 mg, 81%) as a yellow powder. $^1$H NMR (300 MHz, DMSO-$d_6$) δ 8.62 (s, 1H), 8.37 (s, 1H), 4.58 (qd, J=6.9 Hz, 2H), 4.36 and 4.26 (2d, J=13.2 Hz, 1H), 3.92 and 3.75 (2d, J=10.9 Hz, 1H), 3.44-3.31 (m, 2H), 3.22-2.58 (m, 3H), 1.77-1.50 (m, 1H), 1.41 (t, J=7.1 Hz, 3H), 0.93-0.72 (m, 6H). ESIMS m/z [M+H]$^+$ 365.1.

Intermediate AK: 3-Chloro-6-(2,2-dimethylmorpholine-4-carbonyl)-8-ethyl-pyrido[2,3-c]pyridazin-5-one

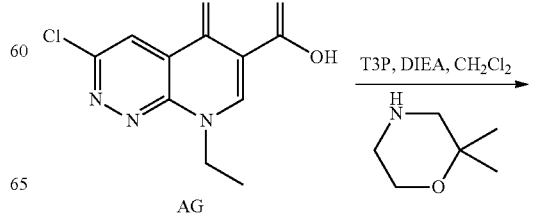

-continued

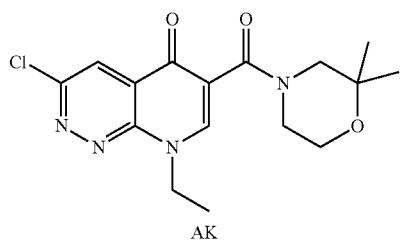

AK

3-Chloro-8-ethyl-5-oxo-pyrido[2,3-c]pyridazine-6-carboxylic acid (185 mg, 0.73 mmol), 2,2-dimethylmorpholine (193 mg, 1.68 mmol), propylphosphonic anhydride solution 50 wt. % in ethyl acetate (0.87 ml, 1.46 mmol) and diisopropylethylamine (0.50 ml, 2.92 mmol) were reacted as described under General Procedure A (18 h at RT) to furnish the title compound (206 mg, 80%) as a yellow powder. $^1$H NMR (300 MHz, DMSO-d$_6$) δ 8.62 (s, 1H), 8.39 and 8.36 (2s, 1H), 4.58 (qd, J=7.1 Hz, 2H), 3.61-3.41 (m, 4H), 3.23-3.12 (m, 2H), 1.41 (t, J=6.9 Hz, 3H), 1.20 and 1.01 (2s, 6H). ESIMS m/z [M+H]$^+$ 351.0.

Intermediate AL: 3-Chloro-6-(2,2,6,6-tetramethyl-morpholine-4-carbonyl)-8-ethyl-pyrido[2,3-c]pyridazin-5-one

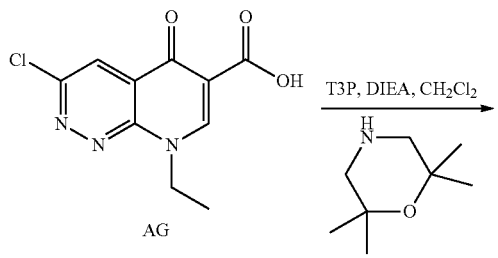

3-Chloro-8-ethyl-5-oxo-pyrido[2,3-c]pyridazine-6-carboxylic acid (185 mg, 0.73 mmol), 2,2,6,6-tetramethylmorpholine (245 mg, 1.68 mmol), propylphosphonic anhydride solution 50 wt. % in ethyl acetate (0.87 ml, 1.46 mmol) and diisopropylethylamine (0.50 ml, 2.92 mmol) were reacted as described under General Procedure A (24 h at RT) to furnish the title compound (200 mg, 72%) as a yellow powder. $^1$H NMR (300 MHz, DMSO-d$_6$) δ 8.71 (s, 1H), 8.37 (s, 1H), 4.59 (qd, J=7.1 Hz, 2H), 3.42 (s, 2H), 3.14 (s, 2H), 1.39 (t, J=7.0 Hz, 3H), 1.18 (s, 6H), 1.01 (s, 6H). ESIMS m/z [M+H]$^+$ 379.1.

Intermediate AM: 3-Chloro-8-ethyl-6-[(2R)-2-(methoxymethyl)morpholine-4-carbonyl]pyrido[2,3-c]pyridazin-5-one

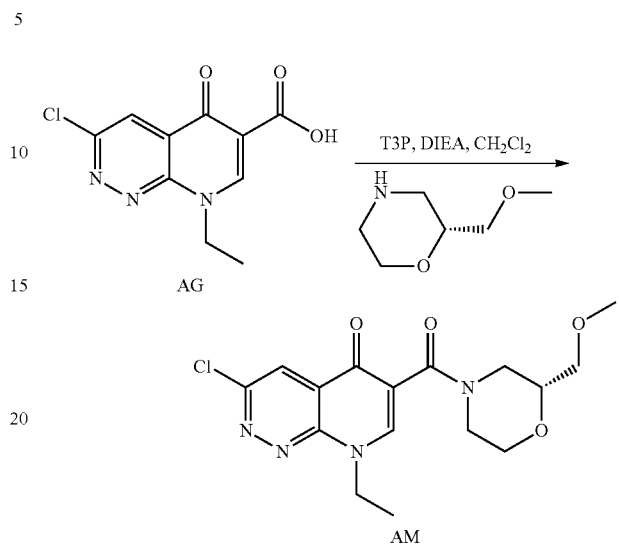

3-Chloro-8-ethyl-5-oxo-pyrido[2,3-c]pyridazine-6-carboxylic acid (450 mg, 1.78 mmol), (2R)-2-methoxymethyl-morpholine (250 mg, 1.45 mmol), propylphosphonic anhydride solution 50 wt. % in ethyl acetate (2.65 ml, 4.47 mmol) and diisopropylethylamine (1.30 ml, 7.45 mmol) were reacted as described under General Procedure A (18 h at RT) to furnish the title compound (458 mg, 84%) as a yellow foam. $^1$H NMR (300 MHz, DMSO-d$_6$) δ 8.62 (s, 1H), 8.39 (s, 1H), 4.58 (qd, J=7.1 Hz, 2H), 4.36-4.25 (m, 1H), 3.81 (dd, J=47.7, 10.0 Hz, 1H), 3.60-3.33 (m, 4H), 3.27 (s, 3H), 3.15 (s, 2H), 2.97-2.80 (m, 1H), 1.41 (t, J=7.0 Hz, 3H). ESIMS m/z [M+H]$^+$ 367.1.

Intermediate AN: 3-Chloro-8-ethyl-6-[(3S)-3-(methoxymethyl)morpholine-4-carbonyl]pyrido[2,3-c]pyridazin-5-one

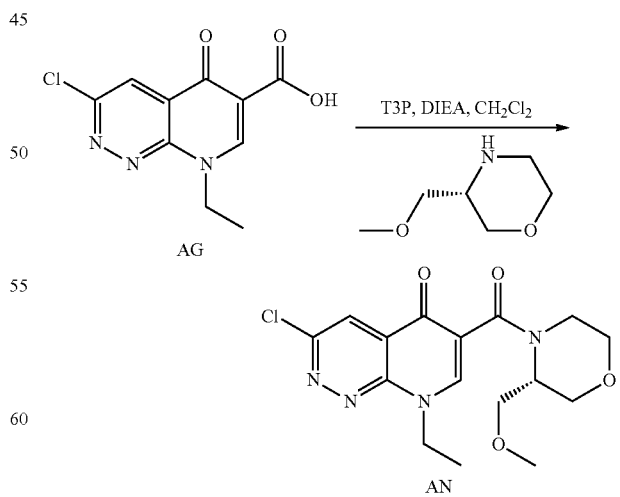

3-Chloro-8-ethyl-5-oxo-pyrido[2,3-c]pyridazine-6-carboxylic acid (363 mg, 1.43 mmol), (3S)-3-methoxymethyl-morpholine (200 mg, 1.19 mmol), propylphosphonic anhydride solution 50 wt. % in ethyl acetate (1.42 ml, 2.38 mmol) and diisopropylethylamine (1.04 ml, 5.95 mmol) were reacted as described under General Procedure A (18 h at RT) to furnish the title compound (350 mg, 80%) as a yellow powder. $^1$H NMR (300 MHz, DMSO-$d_6$) δ 8.58 (d, J=12.6 Hz, 1H), 8.37 (s, 1H), 4.71-4.50 (m, 2H), 4.50-4.08 (m, 1H), 3.95-3.83 (m, 1H), 3.72-3.33 (m, 5H), 3.26-2.98 (m, 2H), 3.14 (s, 3H), 1.40 (t, J=6.1 Hz, 3H). ESIMS m/z [M+H]$^+$ 367.0.

Intermediate AO: 3-Chloro-6-[(2R,5R)-2,5-dimethylmorpholine-4-carbonyl]-8-ethyl-pyrido[2,3-c]pyridazin-5-one

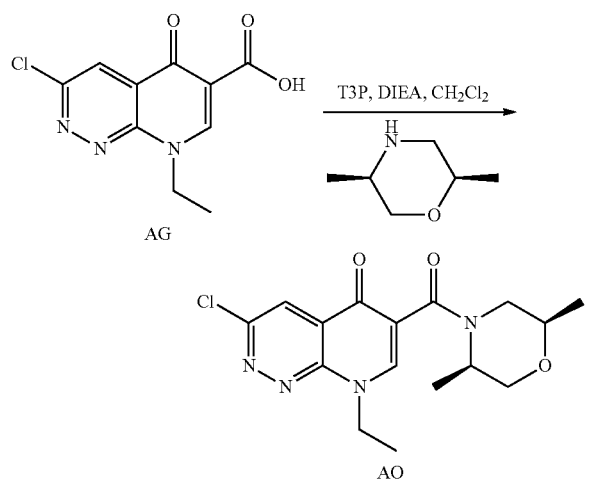

3-Chloro-8-ethyl-5-oxo-pyrido[2,3-c]pyridazine-6-carboxylic acid (558 mg, 2.20 mmol), (2R,5R)-2,5-dimethylmorpholine hydrochloride (278 mg, 1.83 mmol), propylphosphonic anhydride solution 50 wt. % in ethyl acetate (3.07 ml, 5.50 mmol) and diisopropylethylamine (1.60 ml, 9.15 mmol) were reacted as described under General Procedure A (18 h at RT) to furnish the title compound (588 mg, 76%) as a yellow powder. $^1$H NMR (300 MHz, DMSO-$d_6$) δ 8.60 (d, J=7.2 Hz, 1H), 8.37 (d, J=4.0 Hz, 1H), 4.64-4.51 (m, 2H), 4.48-4.15 (m, 1H), 3.69-3.25 (m, 4H), 2.97-2.64 (m, 1H), 1.41 (t, J=6.9 Hz, 3H), 1.22-0.96 (m, 6H). ESIMS m/z [M+H]$^+$ 351.0.

Intermediate AP: 3-Chloro-8-ethyl-6-(6-oxa-3-azabicyclo[3.1.1]heptane-3-carbonyl)pyrido[2,3-c]pyridazin-5-one

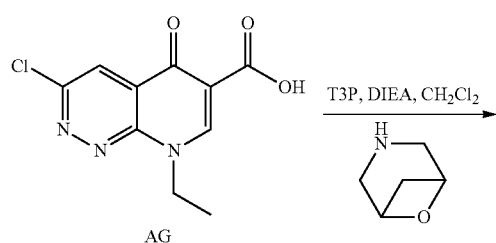

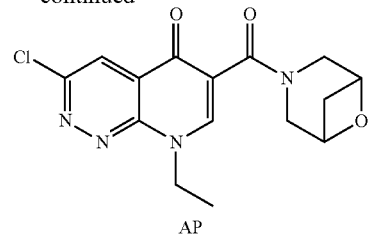

3-Chloro-8-ethyl-5-oxo-pyrido[2,3-c]pyridazine-6-carboxylic acid (160 mg, 0.62 mmol), 6-oxa-3-azabicyclo[3.1.1]heptane tosylate (170 mg, 0.62 mmol), propylphosphonic anhydride solution 50 wt. % in ethyl acetate (0.80 ml, 1.24 mmol) and diisopropylethylamine (0.40 ml, 3.10 mmol) were reacted as described under General Procedure A (18 h at RT) to furnish the title compound (210 mg, 99%) as a yellow powder. $^1$H NMR (300 MHz, DMSO-$d_6$) δ 8.66 (s, 1H), 8.39 (s, 1H), 4.63-4.55 (m, 3H), 4.46 (brs, 1H), 3.87 (d, J=12.7 Hz, 1H), 3.71 (d, J=12.3 Hz, 1H), 3.53 (d, J=12.5 Hz, 2H), 3.09-3.03 (m, 1H), 1.80 (d, J=8.8 Hz, 1H), 1.42 (t, J=7.1 Hz, 3H). ESIMS m/z [M+H]$^+$ 335.0.

Intermediate AQ: 3-Chloro-8-ethyl-6-{(1R,4R)-2-oxa-5-azabicyclo[2.2.1]heptane-5-carbonyl}pyrido[2,3-c]pyridazin-5-one

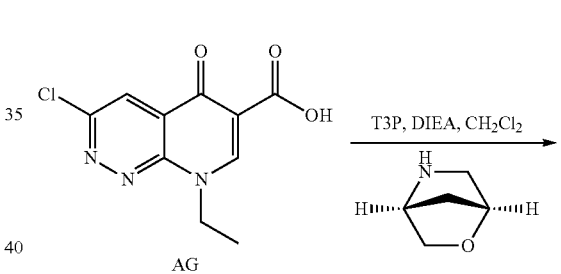

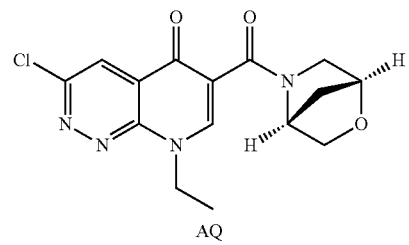

3-Chloro-8-ethyl-5-oxo-pyrido[2,3-c]pyridazine-6-carboxylic acid (630 mg, 2.48 mmol), (1R,4R)-2-oxa-5-azabicyclo[2.2.1]heptane hydrochloride (438 mg, 3.20 mmol), propylphosphonic anhydride solution 50 wt. % in ethyl acetate (2.20 ml, 2.20 mmol) and diisopropylethylamine (1.30 ml, 7.40 mmol) were reacted as described under General Procedure A (18 h at RT) to furnish the title compound (169 mg, 20%) as an orange powder. $^1$H NMR (300 MHz, DMSO-$d_6$) δ 8.67 (s, 1H), 8.43 and 8.38 (2s, 1H), 4.83 and 4.31 (2s, 1H), 4.65-4.55 (m, 3H), 3.94-3.43 (m, 2H), 3.27-3.12 (m, 1H), 1.85-1.73 (m, 3H), 1.44 (t, J=6.9 Hz, 3H). ESIMS m/z [M+H]$^+$ 335.0.

Intermediate AR: 3-Chloro-8-ethyl-6-(3-oxa-8-azabicyclo[3.2.1]octane-8-carbonyl)pyrido[2,3-c]pyridazin-5-one

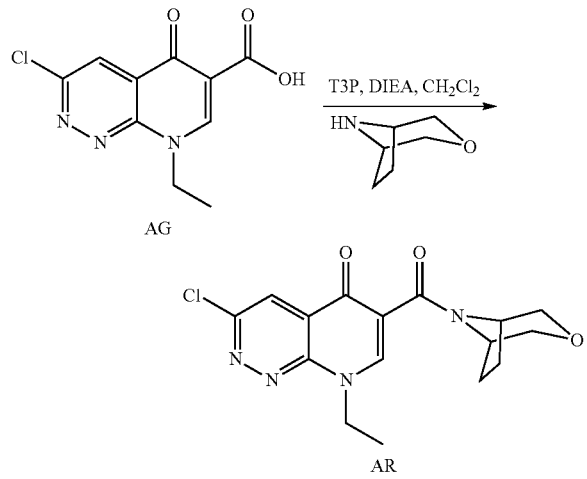

3-Chloro-8-ethyl-5-oxo-pyrido[2,3-c]pyridazine-6-carboxylic acid (170 mg, 0.69 mmol), 3-oxa-8-azabicyclo[3.2.1]octane (235 mg, 1.59 mmol), propylphosphonic anhydride solution 50 wt. % in ethyl acetate (0.80 ml, 1.38 mmol) and diisopropylethylamine (0.59 ml, 3.45 mmol) were reacted as described under General Procedure A (18 h at RT) to furnish the title compound (176 mg, 75%) as a yellow powder. ESIMS m/z [M+H]$^+$ 349.0.

Intermediate AS: 3-Chloro-8-ethyl-6-(8-oxa-3-azabicyclo[3.2.1]octane-3-carbonyl)pyrido[2,3-c]pyridazin-5-one

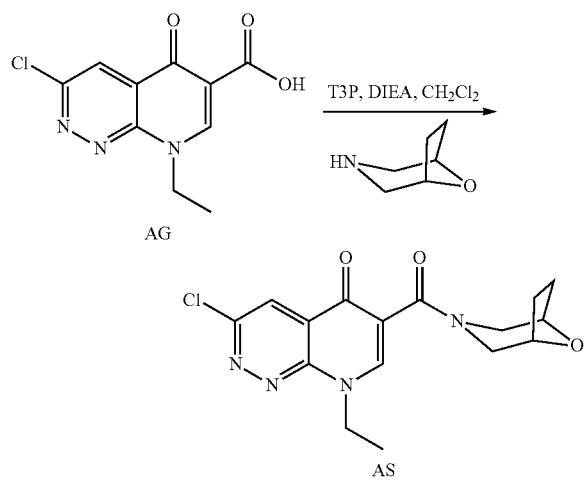

3-Chloro-8-ethyl-5-oxo-pyrido[2,3-c]pyridazine-6-carboxylic acid (900 mg, 3.55 mmol), 8-oxa-3-azabicyclo[3.2.1]octane hydrochloride (797 mg, 5.32 mmol), propylphosphonic anhydride solution 50 wt. % in ethyl acetate (4.23 ml, 7.10 mmol) and diisopropylethylamine (3.09 ml, 17.75 mmol) were reacted as described under General Procedure A (18 h at RT) to furnish the title compound (180 mg, 14%) as a yellow powder. $^1$H NMR (300 MHz, DMSO-d$_6$) δ 8.63 (s, 1H), 8.37 (s, 1H), 4.58 (qd, J=7.0 Hz, 2H), 4.35 (d, J=6.0 Hz, 1H), 4.18-4.13 (m, 2H), 3.23 (s, 2H), 2.92 (d, J=11.8 Hz, 1H), 1.97-1.68 (m, 5H), 1.40 (t, J=7.0 Hz, 3H). ESIMS m/z [M+H]$^+$ 349.0.

Intermediate AT: 3-Chloro-8-ethyl-6-(3-oxa-9-azabicyclo[3.3.1]nonane-9-carbonyl)pyrido[2,3-c]pyridazin-5-one

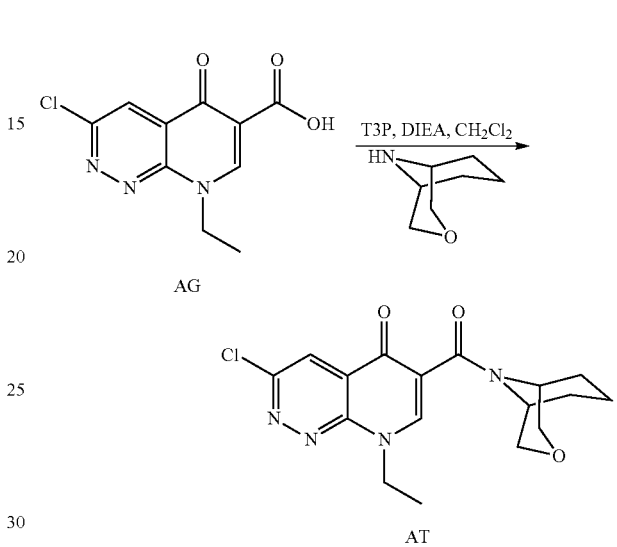

3-Chloro-8-ethyl-5-oxo-pyrido[2,3-c]pyridazine-6-carboxylic acid (254 mg, 1.00 mmol), 3-oxa-9-azabicyclo[3.3.1]nonane hydrochloride (164 mg, 1.00 mmol), propylphosphonic anhydride solution 50 wt. % in ethyl acetate (1.20 ml, 2.00 mmol) and diisopropylethylamine (0.70 ml, 4.00 mmol) were reacted as described under General Procedure A (18 h at RT) to furnish the title compound (259 mg, 71%) as a yellow powder. ESIMS m/z [M+H]$^+$ 363.1.

Intermediate AU: 3-Chloro-8-ethyl-6-(3-oxa-7-azabicyclo[3.3.1]nonane-7-carbonyl)pyrido[2,3-c]pyridazin-5-one

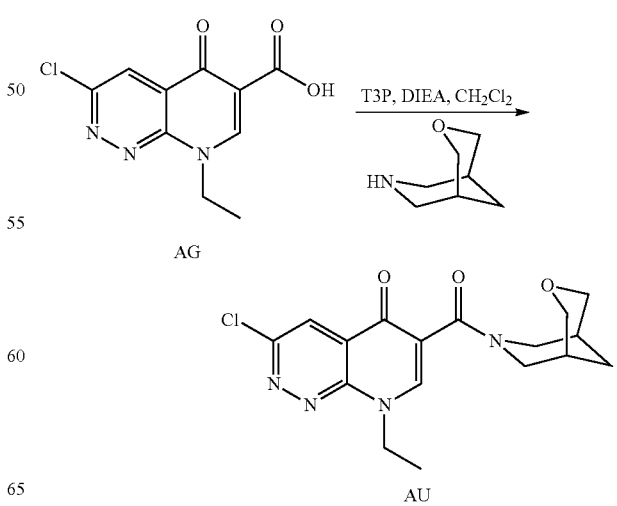

3-Chloro-8-ethyl-5-oxo-pyrido[2,3-c]pyridazine-6-carboxylic acid (550 mg, 2.17 mmol), 3-oxa-7-azabicyclo[3.3.1]nonane (230 mg, 1.81 mmol), propylphosphonic anhydride solution 50 wt. % in ethyl acetate (1.60 ml, 2.69 mmol) and diisopropylethylamine (1.00 ml, 5.74 mmol) were reacted as described under General Procedure A (18 h at RT) to furnish the title compound (630 mg, 96%) as a yellow powder. $^1$H NMR (300 MHz, CHCl$_3$-d) δ 8.37 (s, 1H), 8.23 (s, 1H), 4.96 (d, J=13.4 Hz, 1H), 4.63 (qd, J=7.1 Hz, 2H), 4.12 (d, J=11.0 Hz, 1H), 3.78-3.71 (m, 3H), 3.67 (brs, 2H), 3.15 (d, J=13.4 Hz, 1H), 1.97 (d, J=2.8 Hz, 2H), 1.82 (brs, 1H), 1.64 (brs, 1H), 1.56 (t, J=7.1 Hz, 3H). ESIMS m/z [M+H]$^+$ 363.1.

Intermediate AV: 3-Chloro-8-ethyl-6-(2-oxa-6-azabicyclo[3.3]heptane-6-carbonyl)pyrido[2,3-c]pyridazin-5-one

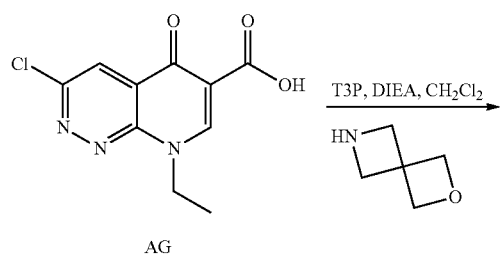

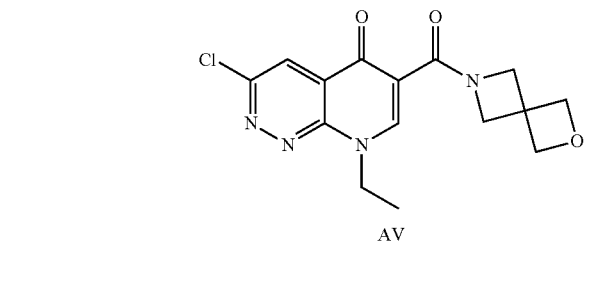

3-Chloro-8-ethyl-5-oxo-pyrido[2,3-c]pyridazine-6-carboxylic acid (490 mg, 1.93 mmol), 2-oxa-6-azaspiro[3.3]heptane (230 mg, 2.32 mmol), propylphosphonic anhydride solution 50 wt. % in ethyl acetate (2.50 ml, 3.86 mmol) and diisopropylethylamine (1.70 ml, 9.65 mmol) were reacted as described under General Procedure A (18 h at RT) to furnish the title compound (490 mg, 76%) as a yellow powder. $^1$H NMR (300 MHz, DMSO-d$_6$) δ 8.69 (s, 1H), 8.39 (s, 1H), 4.70-4.55 (m, 6H), 4.22 (s, 2H), 4.16 (s, 2H), 1.40 (t, J=7.0 Hz, 3H). ESIMS m/z [M+H]$^+$ 335.0.

Intermediate AW: 3-Chloro-8-ethyl-6-(7-oxa-6-azabicyclo[3.5]nonane-2-carbonyl)pyrido[2,3-c]pyridazin-5-one

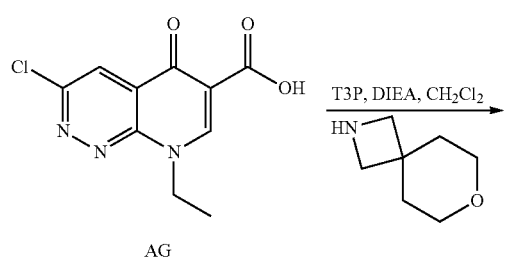

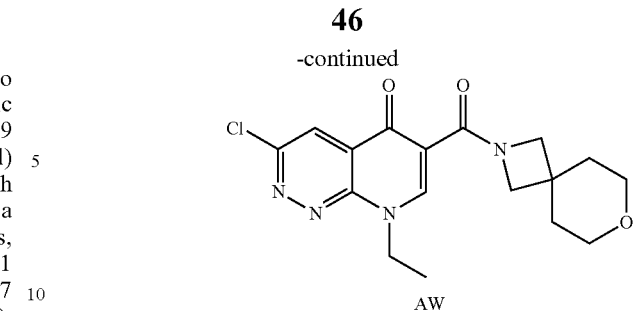

3-Chloro-8-ethyl-5-oxo-pyrido[2,3-c]pyridazine-6-carboxylic acid (469 mg, 1.84 mmol), oxa-2-azaspiro[3.5]nonane hydrochloride (252 mg, 1.54 mmol), propylphosphonic anhydride solution 50 wt. % in ethyl acetate (2.70 ml, 4.62 mmol) and diisopropylethylamine (1.30 ml, 7.70 mmol) were reacted as described under General Procedure A (18 h at RT) to furnish the title compound (310 mg, 55%) as a beige powder. $^1$H NMR (300 MHz, DMSO-d$_6$) δ 8.71 (s, 1H), 8.39 (s, 1H), 4.60 (qd, J=6.7 Hz, 2H), 3.80 (s, 2H), 3.72 (s, 2H), 3.56-3.32 (m, 4H), 1.64 (brs, 4H), 1.41 (t, J=6.1 Hz, 3H). ESIMS m/z [M+H]$^+$ 363.0.

Intermediate AX: 3-Chloro-8-ethyl-6-(7-oxa-6-azabicyclo[3.5]nonane-2-carbonyl)pyrido[2,3-c]pyridazin-5-one

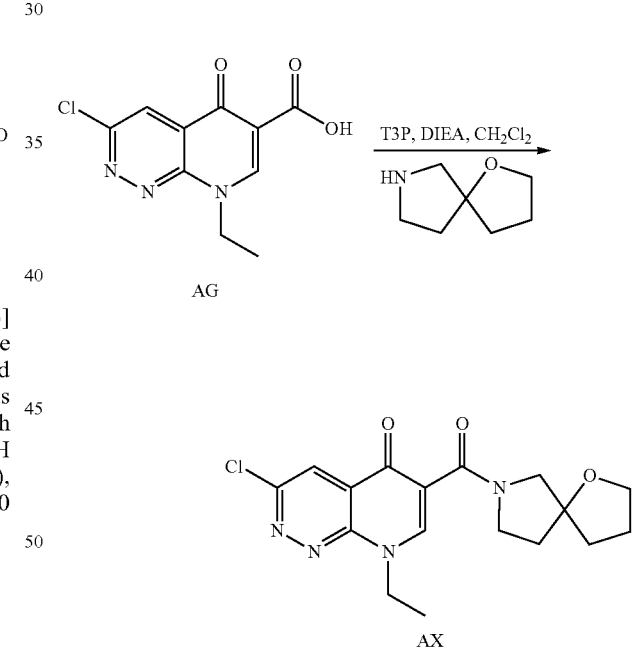

3-Chloro-8-ethyl-5-oxo-pyrido[2,3-c]pyridazine-6-carboxylic acid (479 mg, 1.88 mmol), 1-oxa-7-azaspiro[4.4]nonane (200 mg, 1.57 mmol), propylphosphonic anhydride solution 50 wt. % in ethyl acetate (2.00 ml, 3.14 mmol) and diisopropylethylamine (1.10 ml, 6.28 mmol) were reacted as described under General Procedure A (18 h at RT) to furnish the title compound (476 mg, 82%) as a yellow powder. $^1$H NMR (300 MHz, DMSO-d$_6$) δ 8.65 and 8.63 (2s, 1H), 8.38 and 8.37 (2s, 1H), 4.59 (qd, J=7.2 Hz, 2H), 3.77-3.35 (m, 5H), 3.25 (d, J=11.3 Hz, 1H), 1.93-1.71 (m, 6H), 1.41 (t, J=6.9 Hz, 3H). ESIMS m/z [M+H]$^+$ 363.1.

Intermediate AY: 3-Chloro-8-ethyl-6-(2-oxa-7-azaspiro[4.4]nonane-7-carbonyl)pyrido[2,3-c]pyridazin-5-one

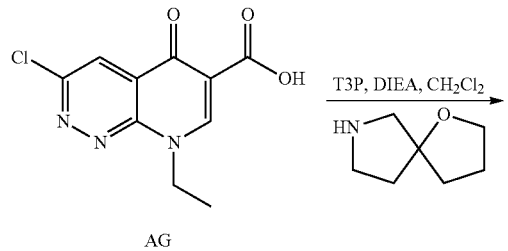

3-Chloro-8-ethyl-5-oxo-pyrido[2,3-c]pyridazine-6-carboxylic acid (550 mg, 2.17 mmol), 2-oxa-7-azaspiro[4.4]nonane hydrochloride (295 mg, 1.80 mmol), propylphosphonic anhydride solution 50 wt. % in ethyl acetate (1.60 ml, 2.69 mmol) and diisopropylethylamine (1.50 ml, 8.61 mmol) were reacted as described under General Procedure A (18 h at RT) to furnish the title compound (440 mg, 67%) as a yellow powder. $^1$H NMR (300 MHz, CHCl$_3$-d) δ 8.38 and 8.37 (2s, 1H), 8.33 and 8.30 (2s, 1H), 4.65 (qd, J=7.1 Hz, 2H), 3.96-3.38 (m, 8H), 2.09-1.87 (m, 4H), 1.59 (t, J=7.1 Hz, 3H). ESIMS m/z [M+H]$^+$ 363.0.

Example 1: 1-Ethyl-6-indan-2-yloxy-3-(morpholine-4-carbonyl)-1,8-naphthyridin-4-one

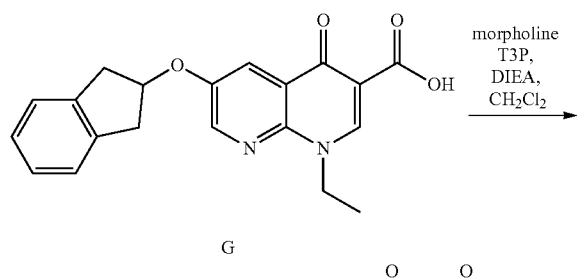

1-Ethyl-6-indan-2-yloxy-4-oxo-1,8-naphthyridine-3-carboxylic acid (300 mg, 0.85 mmol), morpholine (0.10 ml, 1.11 mmol), propylphosphonic anhydride solution 50 wt. % in ethyl acetate (0.70 ml, 1.20 mmol) and diisopropylethylamine (0.40 ml, 2.56 mmol) were reacted as described under General Procedure A (18 h at RT) to furnish the title compound (210 mg, 59%) as a white powder. $^1$H NMR (300 MHz, DMSO-d$_6$) δ 8.55 (d, J=3.1 Hz, 1H), 8.41 (s, 1H), 8.01 (d, J=3.1 Hz, 1H), 7.28-7.25 (m, 2H), 7.18-7.15 (m, 2H), 5.46-5.42 (m, 1H), 4.43 (qd, J=6.8 Hz, 2H), 3.60 (brs, 6H), 3.42 (dd, J=17.2, 5.9 Hz, 2H), 3.28 (brs, 2H), 3.07 (d, J=17.2 Hz, 2H), 1.33 (t, J=7.0 Hz, 3H). ESIMS m/z [M+H]$^+$ 420.1.

Example 2: 1-Ethyl-6-indan-2-yloxy-3-[(2R)-2-methylmorpholine-4-carbonyl]-1,8-naphthyridin-4-one

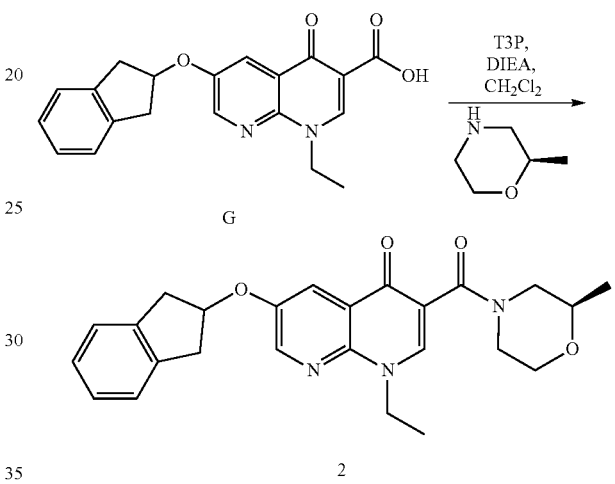

1-Ethyl-6-indan-2-yloxy-4-oxo-1,8-naphthyridine-3-carboxylic acid (200 mg, 0.57 mmol), (2R)-2-methylmorpholine (102 mg, 0.74 mmol), propylphosphonic anhydride solution 50 wt. % in ethyl acetate (0.50 ml, 0.86 mmol) and diisopropylethylamine (0.30 ml, 1.71 mmol) were reacted as described under General Procedure A (18 h at RT) to furnish the title compound (160 mg, 65%) as a white powder. $^1$H NMR (300 MHz, DMSO-d$_6$) δ 8.57 (d, J=3.1 Hz, 1H), 8.42 (s, 1H), 8.03 (d, J=3.1 Hz, 1H), 7.30-7.27 (m, 2H), 7.20-7.17 (m, 2H), 5.48-5.44 (m, 1H), 4.50-4.30 (m, 3H), 3.82 (dd, J=42.0, 10.1 Hz, 1H), 3.55-3.32 (m, 6H), 3.09 (d, J=17.2 Hz, 2H), 2.84 (t, J=11.4 Hz, 1H), 1.35 (t, J=7.0 Hz, 3H), 1.15 and 0.99 (2d, J=5.8 Hz, 3H). ESIMS m/z [M+H]$^+$ 434.1.

Example 3: 1-Ethyl-6-indan-2-yloxy-3-[(2R)-2-isopropylmorpholine-4-carbonyl]-1,8-naphthyridin-4-one

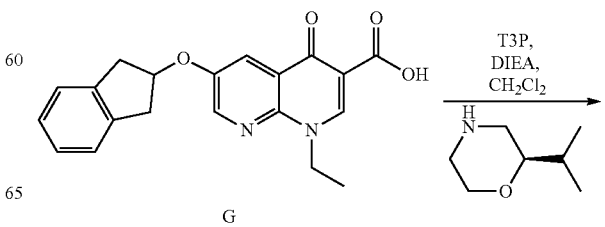

-continued

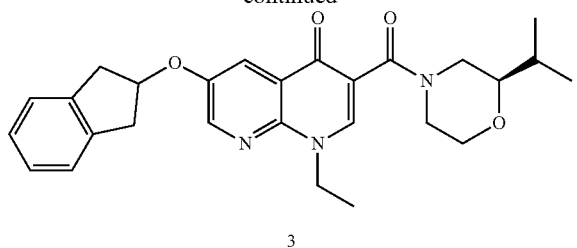

1-Ethyl-6-indan-2-yloxy-4-oxo-1,8-naphthyridine-3-carboxylic acid (300 mg, 0.86 mmol), (2R)-2-isopropylmorpholine (144 mg, 1.11 mmol), propylphosphonic anhydride solution 50 wt. % in ethyl acetate (1.28 ml, 0.76 mmol) and diisopropylethylamine (0.44 ml, 2.57 mmol) were reacted as described under General Procedure A (18 h at RT) to furnish the title compound (150 mg, 38%) as a white foam. $^1$H NMR (300 MHz, DMSO-$d_6$) δ 8.56 (s, 1H), 8.40 (s, 1H), 8.01 (d, J=3.1 Hz, 1H), 7.28-7.25 (m, 2H), 7.19-7.15 (m, 2H), 5.46-5.42 (m, 1H), 4.44-4.27 (m, 3H), 3.85 (dd, J=42.5, 9.4 Hz, 1H), 3.42 (dd, J=16.8, 5.6 Hz, 4H), 3.28-2.50 (m, 5H), 1.76-1.50 (m, 1H), 1.33 (t, J=6.9 Hz, 3H), 0.94-0.82 (m, 6H). ESIMS m/z [M+H]$^+$ 462.1.

Example 4: 3-(2,2-dimethylmorpholine-4-carbonyl)-1-ethyl-6-indan-2-yloxy-1,8-naphthyridin-4-one

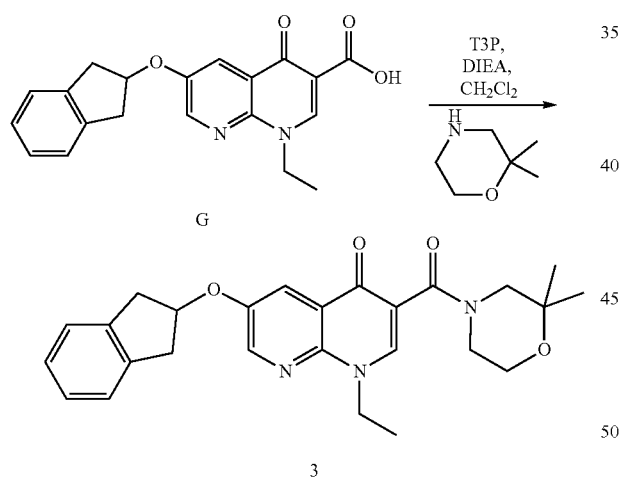

1-Ethyl-6-indan-2-yloxy-4-oxo-1,8-naphthyridine-3-carboxylic acid (300 mg, 0.86 mmol), 2,2-dimethylmorpholine (128 mg, 1.30 mmol), propylphosphonic anhydride solution 50 wt. % in ethyl acetate (0.76 ml, 1.28 mmol) and diisopropylethylamine (0.44 ml, 2.57 mmol) were reacted as described under General Procedure A (18 h at RT) to furnish the title compound (268 mg, 70%) as a white powder. $^1$H NMR (300 MHz, DMSO-$d_6$) δ 8.55 (d, J=3.0 Hz, 1H), 8.41 (s, 1H), 8.03 (d, J=3.0 Hz, 1H), 7.28-7.25 (m, 2H), 7.18-7.15 (m, 2H), 5.46-5.42 (m, 1H), 4.43 (qd, J=6.8 Hz, 2H), 3.70-3.38 (m, 6H), 3.21-3.05 (m, 2H), 3.09 (d, J=17.2 Hz, 2H), 1.33 (t, J=6.6 Hz, 3H), 1.21 and 1.03 (2s, 6H). ESIMS m/z [M+H]$^+$ 448.1.

Example 5: 3-[(2R,6S)-2,6-dimethylmorpholine-4-carbonyl]-1-ethyl-6-indan-2-yloxy-1,8-naphthyridin-4-one

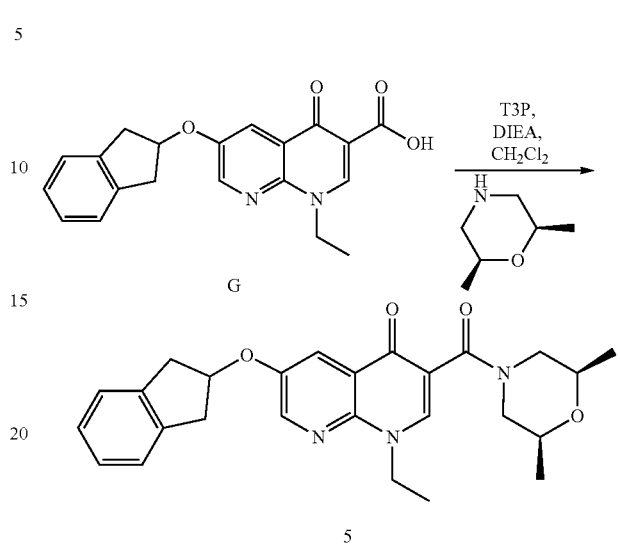

1-Ethyl-6-indan-2-yloxy-4-oxo-1,8-naphthyridine-3-carboxylic acid (300 mg, 0.86 mmol), cis-2,6-dimethylmorpholine (0.14 ml, 1.11 mmol), propylphosphonic anhydride solution 50 wt. % in ethyl acetate (0.70 ml, 1.20 mmol) and diisopropylethylamine (0.44 ml, 2.56 mmol) were reacted as described under General Procedure A (18 h at RT) to furnish the title compound (245 mg, 64%) as a white powder. $^1$H NMR (300 MHz, DMSO-$d_6$) δ 8.55 (d, J=3.1 Hz, 1H), 8.40 (s, 1H), 8.01 (d, J=3.1 Hz, 1H), 7.28-7.25 (m, 2H), 7.18-7.15 (m, 2H), 5.46-5.42 (m, 1H), 4.45-4.35 (m, 3H), 3.60-3.46 (m, 3H), 3.42 (dd, J=17.0, 5.8 Hz, 2H), 3.07 (d, J=16.8 Hz, 2H), 2.71 (d, J=10.9 Hz, 1H), 2.39 (d, J=10.9 Hz, 1H), 1.33 (t, J=7.0 Hz, 3H), 1.13 (d, J=5.9 Hz, 3H), 0.97 (d, J=6.0 Hz, 3H). ESIMS m/z [M+H]$^+$ 448.1.

Example 6: 3-[(2S,6S)-2,6-dimethylmorpholine-4-carbonyl]-1-ethyl-6-indan-2-yloxy-1,8-naphthyridin-4-one

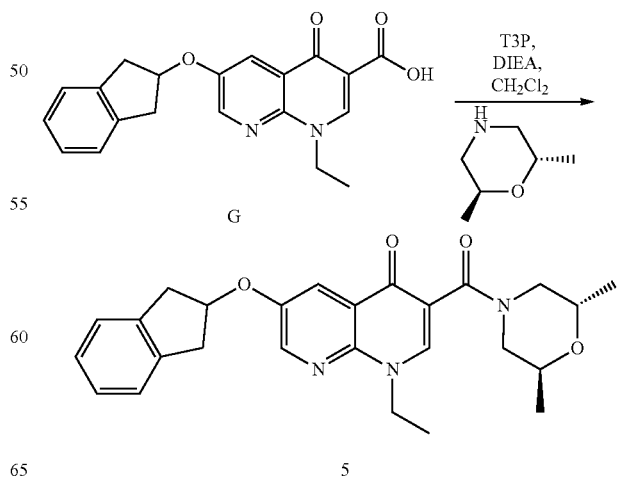

1-Ethyl-6-indan-2-yloxy-4-oxo-1,8-naphthyridine-3-carboxylic acid (230 mg, 0.67 mmol), (2S,6S)-2,6-dimethylmorpholine (100 mg, 0.87 mmol), propylphosphonic anhydride solution 50 wt. % in ethyl acetate (0.60 ml, 1.00 mmol) and diisopropylethylamine (0.34 ml, 2.00 mmol) were reacted as described under General Procedure A (72 h at RT) to furnish the title compound (179 mg, 60%) as a white powder. $^1$H NMR (300 MHz, DMSO-$d_6$) δ 8.55 (d, J=3.1 Hz, 1H), 8.40 (s, 1H), 8.02 (d, J=3.1 Hz, 1H), 7.28-7.25 (m, 2H), 7.19-7.15 (m, 2H), 5.46-5.42 (m, 1H), 4.50-4.36 (m, 2H), 3.97 (brs, 2H), 3.61-3.35 (2m, 3H), 3.43 (dd, J=17.0, 5.6 Hz, 2H), 3.07 (d, J=17.0 Hz, 2H), 2.94-2.87 (m, 1H), 1.33 (t, J=7.0 Hz, 3H), 1.19 (d, J=6.3 Hz, 3H), 0.97 (d, J=6.1 Hz, 3H). ESIMS m/z [M+H]$^+$ 448.1.

Example 7: 3-[(2R,6R)-2,6-dimethylmorpholine-4-carbonyl]-1-ethyl-6-indan-2-yloxy-1,8-naphthyridin-4-one

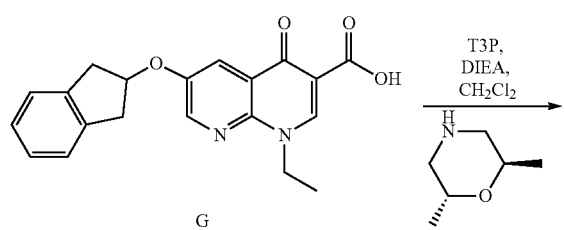

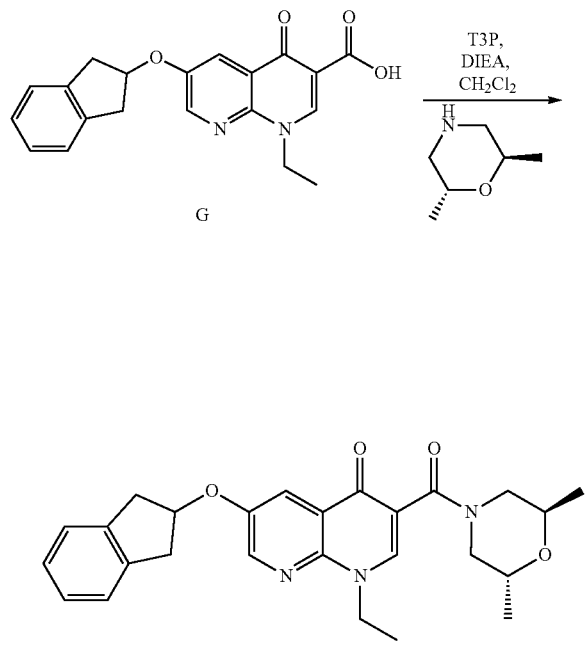

1-Ethyl-6-indan-2-yloxy-4-oxo-1,8-naphthyridine-3-carboxylic acid (250 mg, 0.73 mmol), (2R,6R)-2,6-dimethylmorpholine (107 mg, 0.92 mmol), propylphosphonic anhydride solution 50 wt. % in ethyl acetate (0.64 ml, 1.07 mmol) and diisopropylethylamine (0.34 ml, 2.14 mmol) were reacted as described under General Procedure A (18 h at RT) to furnish the title compound (238 mg, 75%) as a white powder. $^1$H NMR (300 MHz, DMSO-$d_6$) δ 8.57 (d, J=3.1 Hz, 1H), 8.42 (s, 1H), 8.04 (d, J=3.1 Hz, 1H), 7.30-7.27 (m, 2H), 7.19-7.17 (m, 2H), 5.48-5.44 (m, 1H), 4.50-4.36 (m, 2H), 3.97 (brs, 2H), 3.60 and 3.33 (2m, 3H), 3.44 (dd, J=16.8, 5.4 Hz, 2H), 3.10 (d, J=16.8 Hz, 2H), 2.96-2.87 (m, 1H), 1.34 (t, J=7.0 Hz, 3H), 1.21 (d, J=6.1 Hz, 3H), 0.98 (d, J=6.1 Hz, 3H). ESIMS m/z [M+H]$^+$ 448.2.

Example 8: 1-Ethyl-6-indan-2-yloxy-3-(2,2,6,6-tetramethylmorpholine-4-carbonyl)-1,8-naphthyridin-4-one

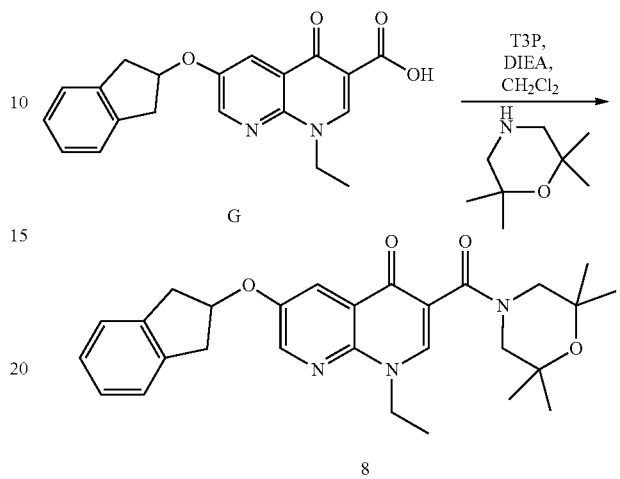

1-Ethyl-6-indan-2-yloxy-4-oxo-1,8-naphthyridine-3-carboxylic acid (245 mg, 0.70 mmol), 2,2,6,6-tetramethylmorpholine (100 mg, 0.70 mmol), propylphosphonic anhydride solution 50 wt. % in ethyl acetate (0.60 ml, 1.04 mmol) and diisopropylethylamine (0.40 ml, 2.05 mmol) were reacted as described under General Procedure A (18 h at RT) to furnish the title compound (270 mg, 81%) as a white powder. $^1$H NMR (300 MHz, DMSO-$d_6$) δ 8.55 (d, J=3.1 Hz, 1H), 8.49 (s, 1H), 8.01 (d, J=3.1 Hz, 1H), 7.28-7.25 (m, 2H), 7.18-7.15 (m, 2H), 5.46-5.42 (m, 1H), 4.44 (qd, J=7.1 Hz, 2H), 3.45 (brs, 2H), 3.42 (dd, J=16.9, 6.8 Hz, 2H), 3.15 (brs, 2H), 3.08 (d, J=17.2 Hz, 2H), 1.31 (t, J=6.8 Hz, 3H), 1.19 (s, 6H), 1.03 (s, 6H). ESIMS m/z [M+H]$^+$ 476.2.

Example 9: 1-Ethyl-6-indan-2-yloxy-3-[(2R)-2-(methoxymethyl)morpholine-4-carbonyl]-1,8-naphthyridin-4-one

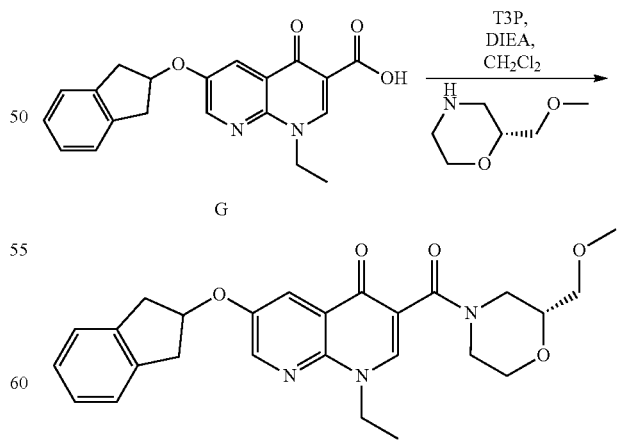

1-Ethyl-6-indan-2-yloxy-4-oxo-1,8-naphthyridine-3-carboxylic acid (300 mg, 0.86 mmol), (2R)-2-methoxymethylmorpholine hydrochloride (186 mg, 1.11 mmol), propylphosphonic anhydride solution 50 wt. % in ethyl acetate (0.76 ml, 1.28 mmol) and diisopropylethylamine (0.58 ml, 3.42 mmol) were reacted as described under General Procedure A (18 h at RT) to furnish the title compound (160 mg, 40%) as a white foam. $^1$H NMR (300 MHz, CH$_3$OH-d$_4$) δ 8.55 (d, J=3.1 Hz, 1H), 8.39 (s, 1H), 8.15 (d, J=3.0 Hz, 1H), 7.27-7.24 (m, 2H), 7.19-7.15 (m, 2H), 5.41-5.37 (m, 1H), 4.60-4.44 (m, 3H), 3.93 (dd, J=43.1, 9.0 Hz, 1H), 3.76-3.57 (m, 2H), 3.49 (dd, J=16.8, 5.8 Hz, 4H), 3.40 (s, 3H), 3.39-3.35 (m, 1H), 3.18 (d, J=17.0 Hz, 2H), 3.10-2.83 (m, 2H), 1.47 (t, J=7.1 Hz, 3H). ESIMS m/z [M+H]$^+$ 464.1.

Example 10: 3-[(3R,5S)-3,5-dimethylmorpholine-4-carbonyl]-1-ethyl-6-indan-2-yloxy-1,8-naphthyridin-4-one

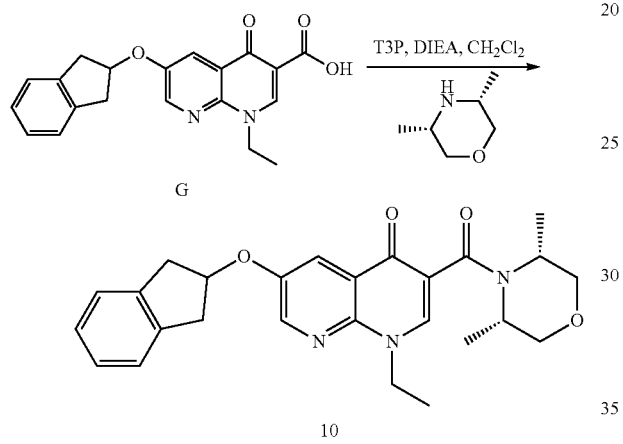

10

1-Ethyl-6-indan-2-yloxy-4-oxo-1,8-naphthyridine-3-carboxylic acid (300 mg, 0.86 mmol), cis-3,5-dimethylmorpholine (0.06 ml, 0.45 mmol), propylphosphonic anhydride solution 50 wt. % in ethyl acetate (0.76 ml, 1.28 mmol) and diisopropylethylamine (0.44 ml, 2.57 mmol) were reacted as described under General Procedure A (18 h at RT) to furnish the title compound (144 mg, 72%) as a white powder. $^1$H NMR (300 MHz, DMSO-d$_6$) δ 8.55 (d, J=3.1 Hz, 1H), 8.42 (s, 1H), 8.01 (d, J=3.1 Hz, 1H), 7.28-7.25 (m, 2H), 7.18-7.15 (m, 2H), 5.45-5.41 (m, 1H), 4.44 (qd, J=7.0 Hz, 2H), 4.00 (brs, 2H), 3.66 (d, J=11.3 Hz, 2H), 3.51 (dd, J=11.3, 3.3 Hz, 2H), 3.42 (dd, J=17.1, 5.9 Hz, 2H), 3.08 (d, J=16.9 Hz, 2H), 1.32 (t, J=6.9 Hz, 3H), 1.25 (d, J=6.1 Hz, 6H). ESIMS m/z [M+H]$^+$ 448.2.

Example 11: 3-[(3R,5R)-3,5-dimethylmorpholine-4-carbonyl]-1-ethyl-6-indan-2-yloxy-1,8-naphthyridin-4-one

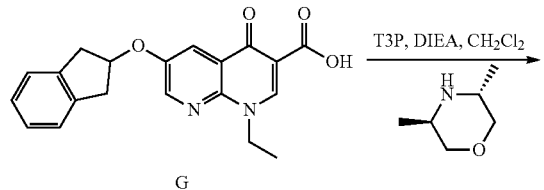

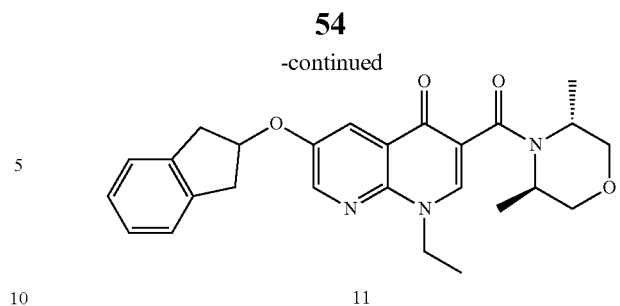

11

1-Ethyl-6-indan-2-yloxy-4-oxo-1,8-naphthyridine-3-carboxylic acid (300 mg, 0.86 mmol), (3R,5R)-3,5-dimethylmorpholine (0.15 ml, 1.11 mmol), propylphosphonic anhydride solution 50 wt. % in ethyl acetate (0.76 ml, 1.28 mmol) and diisopropylethylamine (0.44 ml, 2.57 mmol) were reacted as described under General Procedure A (18 h at RT) to furnish the title compound (304 mg, 79%) as a white powder. $^1$H NMR (300 MHz, DMSO-d$_6$) δ 8.55 (d, J=3.1 Hz, 1H), 8.43 (s, 1H), 8.02 (d, J=3.1 Hz, 1H), 7.28-7.25 (m, 2H), 7.18-7.15 (m, 2H), 5.44-5.40 (m, 1H), 4.49-4.40 (m, 2H), 3.86-3.80 (m, 4H), 3.46-3.39 (m, 4H), 3.08 (d, J=17.0 Hz, 2H), 1.33 (t, J=7.0 Hz, 3H), 1.21 (d, J=6.2 Hz, 6H). ESIMS m/z [M+H]$^+$ 448.2.

Example 12: 3-(3,3-dimethylmorpholine-4-carbonyl)-1-ethyl-6-indan-2-yloxy-1,8-naphthyridin-4-one

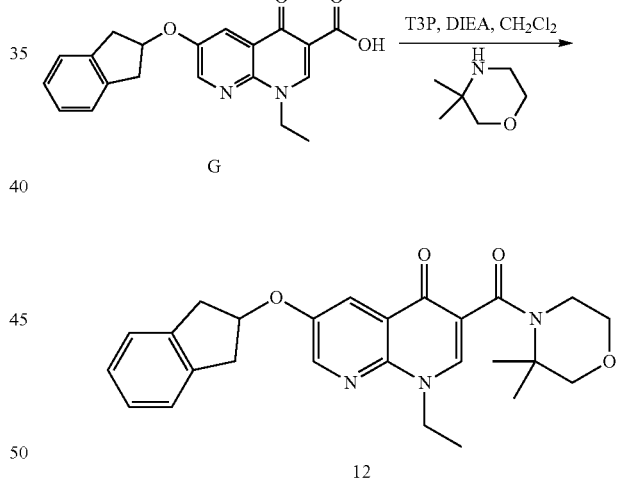

12

1-Ethyl-6-indan-2-yloxy-4-oxo-1,8-naphthyridine-3-carboxylic acid (300 mg, 0.85 mmol), 3,3-dimethylmorpholine (128 mg, 1.11 mmol), propylphosphonic anhydride solution 50 wt. % in ethyl acetate (0.72 ml, 1.19 mmol) and diisopropylethylamine (0.43 ml, 2.55 mmol) were reacted as described under General Procedure A (18 h at RT, 18 h at 50° C., 18 h at 100° C.) to furnish the title compound (33 mg, 8%) as a white foam. $^1$H NMR (300 MHz, DMSO-d$_6$) δ 8.54 (d, J=3.0 Hz, 1H), 8.37 (s, 1H), 8.01 (d, J=3.1 Hz, 1H), 7.28-7.25 (m, 2H), 7.18-7.15 (m, 2H), 5.44-5.40 (m, 1H), 4.43 (qd, J=7.0 Hz, 2H), 3.67 (t, J=4.6 Hz, 2H), 3.42 (dd, J=17.2, 6.0 Hz, 4H), 3.37 (s, 2H), 3.07 (d, J=16.1 Hz, 2H), 1.40 (s, 6H), 1.32 (t, J=6.9 Hz, 3H). ESIMS m/z [M+H]$^+$ 448.1.

Example 13: 1-ethyl-6-indan-2-yloxy-3-[(3S)-3-(methoxymethyl)morpholine-4-carbonyl]-1,8-naphthyridin-4-one

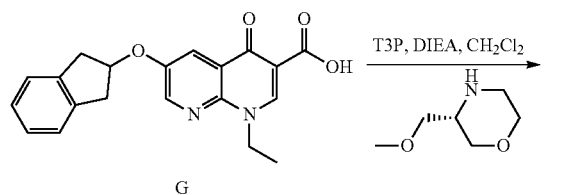

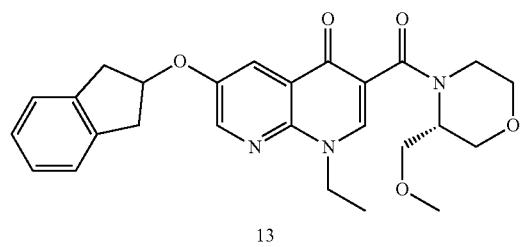

13

1-Ethyl-6-indan-2-yloxy-4-oxo-1,8-naphthyridine-3-carboxylic acid (300 mg, 0.85 mmol), (S)-3-methoxymethylmorpholine hydrochloride (186 mg, 1.11 mmol), propylphosphonic anhydride solution 50 wt. % in ethyl acetate (0.72 ml, 1.19 mmol) and diisopropylethylamine (0.58 ml, 3.40 mmol) were reacted as described under General Procedure A (18 h at RT) to furnish the title compound (260 mg, 66%) as a white solid. ¹H NMR (300 MHz, DMSO-d₆) δ 8.55 (d, J=3.1 Hz, 1H), 8.37 (d, J=12.1 Hz, 1H), 8.01 (d, J=2.8 Hz, 1H), 7.28-7.25 (m, 2H), 7.19-7.15 (m, 2H), 5.45-5.40 (m, 1H), 4.58-4.10 (m, 3H), 3.92-3.84 (m, 1H), 3.75-3.55 (m, 3H), 3.42 (dd, J=17.1, 5.8 Hz, 4H), 3.32 (s, 3H), 3.11 (s, 2H), 3.08 (d, J=16.1 Hz, 2H), 1.32 (t, J=6.7 Hz, 3H). ESIMS m/z [M+H]⁺ 464.2.

Example 14: 3-[(2R,5R)-2,5-dimethylmorpholine-4-carbonyl]-1-ethyl-6-indan-2-yloxy-1,8-naphthyridin-4-one

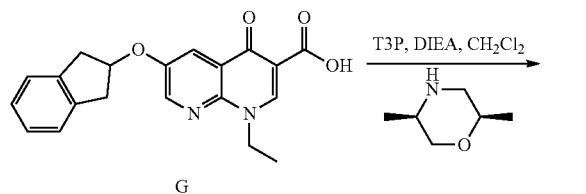

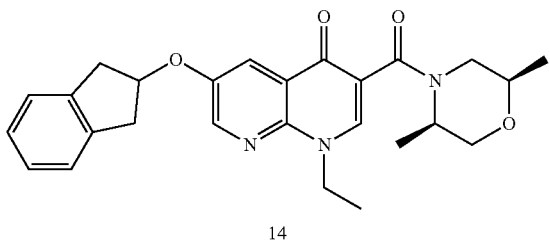

14

1-Ethyl-6-indan-2-yloxy-4-oxo-1,8-naphthyridine-3-carboxylic acid (300 mg, 0.86 mmol), (2R,5R)-2,5-dimethylmorpholine hydrochloride (169 mg, 1.11 mmol), propylphosphonic anhydride solution 50 wt. % in ethyl acetate (0.76 ml, 1.28 mmol) and diisopropylethylamine (0.58 ml, 3.42 mmol) were reacted as described under General Procedure A (18 h at RT) to furnish the title compound (260 mg, 68%) as a white solid. ¹H NMR (300 MHz, DMSO-d₆) δ 8.55 (d, J=3.1 Hz, 1H), 8.37 (d, J=5.4 Hz, 1H), 8.01 (d, J=2.9 Hz, 1H), 7.28-7.25 (m, 2H), 7.18-7.15 (m, 2H), 5.45-5.41 (m, 1H), 4.52-4.17 (m, 3H), 3.70-3.51 (m, 1H), 3.42 (dd, J=17.1, 5.8 Hz, 4H), 3.27-2.63 (m, 4H), 1.33 (t, J=6.7 Hz, 3H), 1.23-0.99 (m, 6H). ESIMS m/z [M+H]⁺ 448.2.

Example 15: 1-Ethyl-6-indan-2-yloxy-3-(6-oxa-3-azabicyclo[3.1.1]heptane-3-carbonyl)-1,8-naphthyridin-4-one

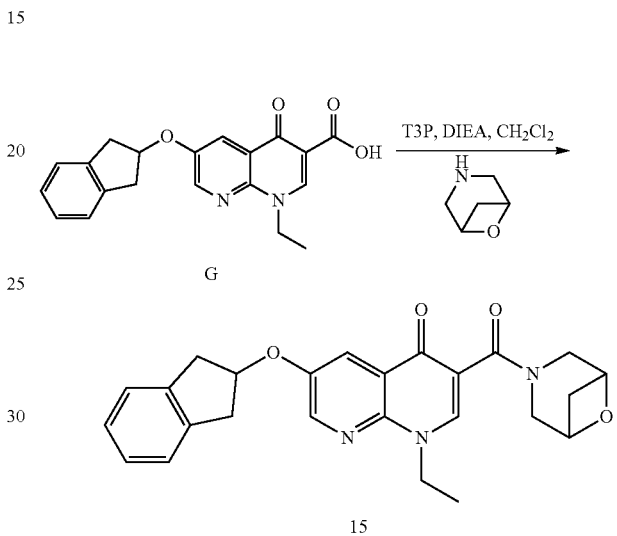

15

1-Ethyl-6-indan-2-yloxy-4-oxo-1,8-naphthyridine-3-carboxylic acid (300 mg, 0.85 mmol), 6-oxa-3-azabicyclo[3.1.1]heptane tosylate (250 mg, 0.92 mmol), propylphosphonic anhydride solution 50 wt. % in ethyl acetate (0.76 ml, 1.28 mmol) and diisopropylethylamine (0.60 ml, 3.46 mmol) were reacted as described under General Procedure A (18 h at RT) to furnish the title compound (200 mg, 54%) as a white foam. ¹H NMR (300 MHz, DMSO-d₆) δ 8.56 (d, J=3.1 Hz, 1H), 8.43 (s, 1H), 8.02 (d, J=3.1 Hz, 1H), 7.26-7.24 (m, 2H), 7.18-7.15 (m, 2H), 5.45-5.41 (m, 1H), 4.64-4.60 (m, 1H), 4.50-4.40 (m, 3H), 3.87 (d, J=13.4 Hz, 1H), 3.73 (d, J=10.8 Hz, 1H), 3.62-3.52 (m, 2H), 3.42 (dd, J=17.2, 6.0 Hz, 2H), 3.11-3.05 (m, 3H), 1.84 (d, J=8.8 Hz, 1H), 1.34 (t, J=7.0 Hz, 3H). ESIMS m/z [M+H]⁺ 432.1.

Example 16: 1-Ethyl-6-indan-2-yloxy-3-(3-oxa-6-azabicyclo[3.1.1]heptane-6-carbonyl)-1,8-naphthyridin-4-one

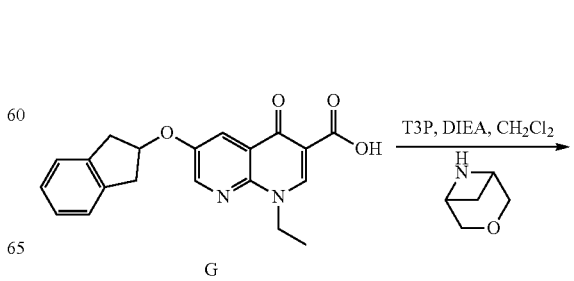

-continued

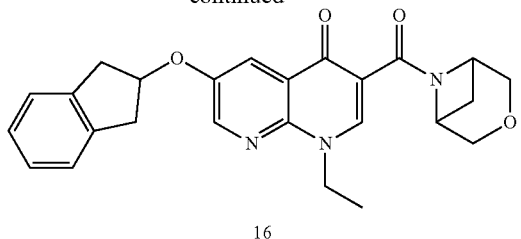

16

1-Ethyl-6-indan-2-yloxy-4-oxo-1,8-naphthyridine-3-carboxylic acid (200 mg, 0.57 mmol), 3-oxa-6-azabicyclo[3.1.1]heptane hydrochloride (100 mg, 0.79 mmol), propylphosphonic anhydride solution 50 wt. % in ethyl acetate (0.51 ml, 0.85 mmol) and diisopropylethylamine (0.39 ml, 2.27 mmol) were reacted as described under General Procedure A (18 h at RT) to furnish the title compound (78 mg, 32%) as a white powder. $^1$H NMR (300 MHz, DMSO-$d_6$) δ 8.61 (s, 1H), 8.54 (d, J=3.0 Hz, 1H), 8.03 (d, J=3.1 Hz, 1H), 7.28-7.25 (m, 2H), 7.17-7.15 (m, 2H), 5.45-5.41 (m, 1H), 4.51-4.37 (m, 4H), 4.20 (d, J=10.1 Hz, 1H), 3.87-3.69 (m, 3H), 3.42 (dd, J=17.1, 5.8 Hz, 2H), 3.07 (d, J=16.9 Hz, 2H), 2.62-2.46 (m, 1H), 1.79 (d, J=8.0 Hz, 1H), 1.33 (t, J=7.0 Hz, 3H). ESIMS m/z [M+H]$^+$ 432.1.

Example 17: 1-Ethyl-6-indan-2-yloxy-3-[(1R,4R)-2-oxa-5-azabicyclo[2.2.1]heptane-5-carbonyl]-1,8-naphthyridin-4-one

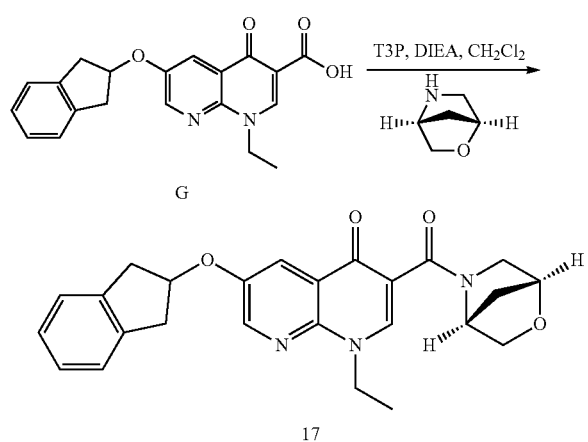

17

1-Ethyl-6-indan-2-yloxy-4-oxo-1,8-naphthyridine-3-carboxylic acid (300 mg, 0.85 mmol), (1R,4R)-2-oxa-5-azabicyclo[2.2.1]heptane hydrochloride (151 mg, 1.11 mmol), propylphosphonic anhydride solution 50 wt. % in ethyl acetate (0.76 ml, 1.28 mmol) and diisopropylethylamine (0.60 ml, 4.60 mmol) were reacted as described under General Procedure A (20 h at RT) to furnish the title compound (125 mg, 34%) as a white powder. $^1$H NMR (300 MHz, DMSO-$d_6$) δ 8.61 (s, 1H), 8.55 (d, J=3.0 Hz, 1H), 8.44 (d, J=5.2 Hz, 1H), 8.03 (dd, J=11.2, 3.0 Hz, 1H), 7.26-7.25 (m, 2H), 7.18-7.15 (m, 2H), 5.47-5.41 (m, 1H), 4.82 and 4.62 (2s, 1H), 4.56 and 4.28 (2s, 1H), 4.44 (qd, J=6.9 Hz, 2H), 3.95-3.39 (m, 5H), 3.26-3.17 (m, 1H), 3.07 (d, J=17.2 Hz, 2H), 1.81 and 1.76 (2s, 1H), 1.34 (t, J=6.9 Hz, 3H). ESIMS m/z [M+H]$^+$ 432.1.

Example 18: 1-Ethyl-6-indan-2-yloxy-3-(3-oxa-8-azabicyclo[3.2.1]octane-8-carbonyl)-1,8-naphthyridin-4-one

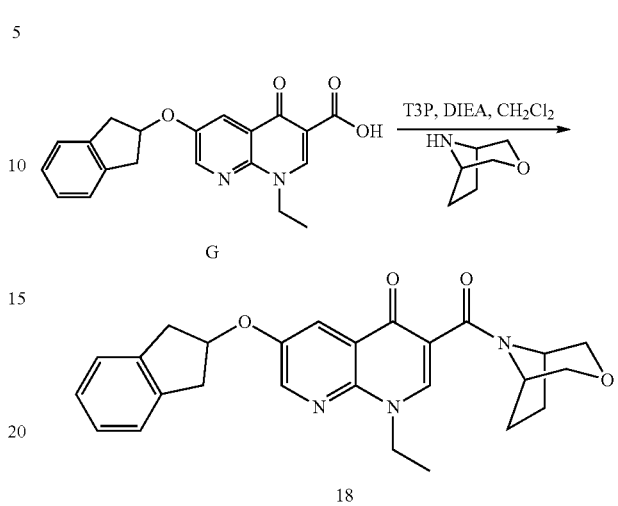

18

1-Ethyl-6-indan-2-yloxy-4-oxo-1,8-naphthyridine-3-carboxylic acid (300 mg, 0.85 mmol), 3-oxa-8-azabicyclo[3.2.1]octane (167 mg, 1.11 mmol), propylphosphonic anhydride solution 50 wt. % in ethyl acetate (0.72 ml, 1.19 mmol) and diisopropylethylamine (0.58 ml, 3.40 mmol) were reacted as described under General Procedure A (18 h at RT) to furnish the title compound (310 mg, 82%) as a white powder. $^1$H NMR (300 MHz, DMSO-$d_6$) δ 8.54 (d, J=3.1 Hz, 1H), 8.49 (s, 1H), 8.03 (d, J=3.1 Hz, 1H), 7.28-7.25 (m, 2H), 7.17-7.15 (m, 2H), 5.46-5.42 (m, 1H), 4.53-4.43 (m, 3H), 3.82 (d, J=5.2 Hz, 1H), 3.66-3.49 (m, 4H), 3.42 (dd, J=16.9, 5.6 Hz, 2H), 3.07 (d, J=16.9 Hz, 2H), 1.93-1.81 (m, 4H), 1.33 (t, J=7.0 Hz, 3H). ESIMS m/z [M+H]$^+$ 446.1.

Example 19: 1-Ethyl-6-indan-2-yloxy-3-(8-oxa-3-azabicyclo[3.2.1]octane-3-carbonyl)-1,8-naphthyridin-4-one

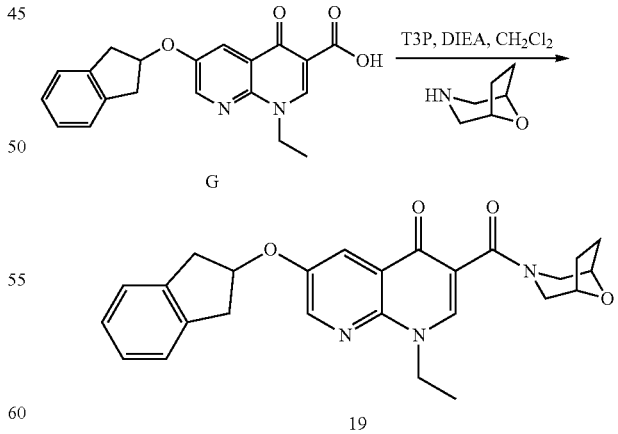

19

1-Ethyl-6-indan-2-yloxy-4-oxo-1,8-naphthyridine-3-carboxylic acid (300 mg, 0.85 mmol), 8-oxa-3-azabicyclo[3.2.1]octane hydrochloride (170 mg, 1.10 mmol), propylphosphonic anhydride solution 50 wt. % in ethyl acetate (0.76 ml, 1.28 mmol) and diisopropylethylamine (0.45 ml, 2.56 mmol) were reacted as described under General Procedure A (18 h at RT) to furnish the title compound (281 mg, 74%) as a white powder. $^1$H NMR (300 MHz, DMSO-$d_6$) δ 8.55 (d, J=3.1 Hz, 1H), 8.41 (s, 1H), 8.01 (d, J=3.1 Hz, 1H), 7.28-7.25 (m, 2H), 7.17-7.15 (m, 2H), 5.43 (t, J=5.8 Hz, 1H), 4.43 (qd, J=6.9 Hz, 2H), 4.35 (d, J=6.0 Hz, 1H), 4.19-4.09 (m, 2H), 3.39 (dd, J=17.1, 5.9 Hz, 2H), 3.26-3.17 (m, 2H), 3.07 (d, J=17.1 Hz, 2H), 2.91 (d, J=12.1 Hz, 2H), 2.03-1.91 (m, 1H), 1.84-1.68 (m, 2H), 1.32 (t, J=7.0 Hz, 3H). ESIMS m/z [M+H]$^+$ 446.1.

Example 20: 1-Ethyl-6-indan-2-yloxy-3-(3-oxa-9-azabicyclo[3.3.1]nonane-9-carbonyl)-1,8-naphthyridin-4-one

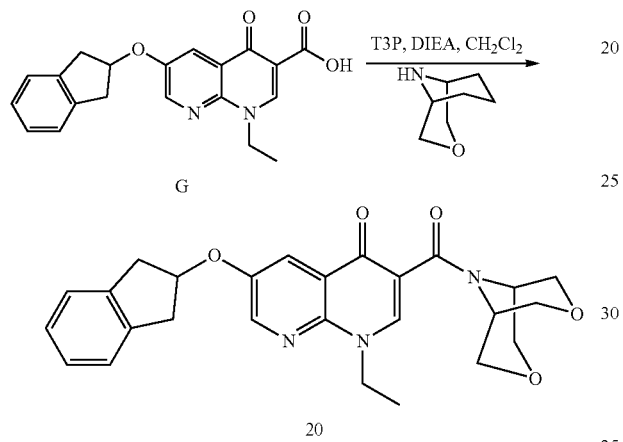

1-Ethyl-6-indan-2-yloxy-4-oxo-1,8-naphthyridine-3-carboxylic acid (300 mg, 0.85 mmol), 3-oxa-9-azabicyclo[3.3.1]nonane hydrochloride (182 mg, 1.11 mmol), propylphosphonic anhydride solution 50 wt. % in ethyl acetate (0.72 ml, 1.19 mmol) and diisopropylethylamine (0.58 ml, 3.40 mmol) were reacted as described under General Procedure A (18 h at RT) to furnish the title compound (235 mg, 76%) as a white powder. $^1$H NMR (300 MHz, CH$_3$OH-$d_4$) δ 8.54 (d, J=3.1 Hz, 1H), 8.41 (s, 1H), 8.14 (d, J=3.1 Hz, 1H), 7.26-7.23 (m, 2H), 7.19-7.15 (m, 2H), 5.42-5.36 (m, 1H), 4.61-4.53 (m, 3H), 4.01 (d, J=11.3 Hz, 2H), 3.89 (t, J=12.0 Hz, 1H), 3.66 (brs, 1H), 3.49 (dd, J=17.0, 6.0 Hz, 2H), 3.17 (d, J=16.9 Hz, 2H), 2.65-2.48 (m, 1H), 2.10-1.91 (m, 3H), 1.90-1.80 (m, 1H), 1.70-1.60 (m, 1H), 1.47 (t, J=7.1 Hz, 3H). ESIMS m/z [M+H]$^+$ 460.1.

Example 21: 1-Ethyl-6-indan-2-yloxy-3-(3-oxa-7-azabicyclo[3.3.1]nonane-7-carbonyl)-1,8-naphthyridin-4-one

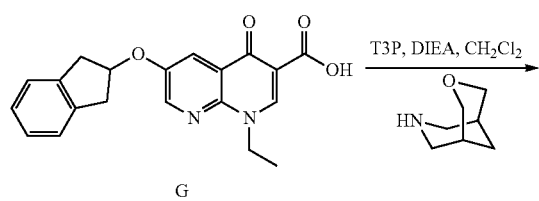

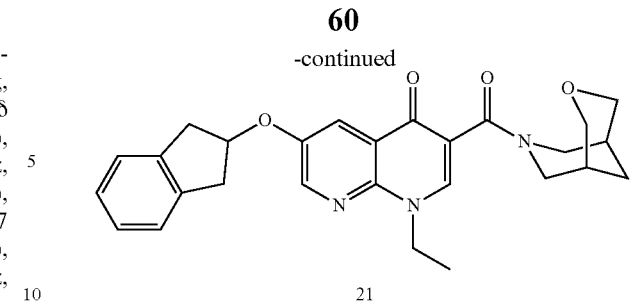

1-Ethyl-6-indan-2-yloxy-4-oxo-1,8-naphthyridine-3-carboxylic acid (300 mg, 0.85 mmol), 3-oxa-7-azabicyclo[3.3.1]nonane (141 mg, 1.11 mmol), propylphosphonic anhydride solution 50 wt. % in ethyl acetate (0.72 ml, 1.19 mmol) and diisopropylethylamine (0.50 ml, 2.55 mmol) were reacted as described under General Procedure A (18 h at RT) to furnish the title compound (217 mg, 56%) as a white foam. $^1$H NMR (300 MHz, DMSO-$d_6$) δ 8.55 (d, J=3.2 Hz, 1H), 8.13 (s, 1H), 8.00 (d, J=3.1 Hz, 1H), 7.27-7.25 (m, 2H), 7.18-7.15 (m, 2H), 5.46-5.41 (m, 1H), 4.69 (d, J=12.4 Hz, 2H), 4.45 (qd, J=7.0 Hz, 2H), 3.86 (d, J=11.2 Hz, 2H), 3.70-3.52 (m, 4H), 3.42 (dd, J=17.0, 6.0 Hz, 2H), 3.40-3.37 (m, 1H), 3.14-2.98 (m, 3H), 1.86 (br s, 2H), 1.75 (br s, 1H), 1.56 (br s, 1H), 1.30 (t, J=7.0 Hz, 3H). ESIMS m/z [M+H]$^+$ 460.2.

Example 22: 1-Ethyl-6-indan-2-yloxy-3-(2-oxa-6-azaspiro[3.3]heptane-6-carbonyl)-1,8-naphthyridin-4-one

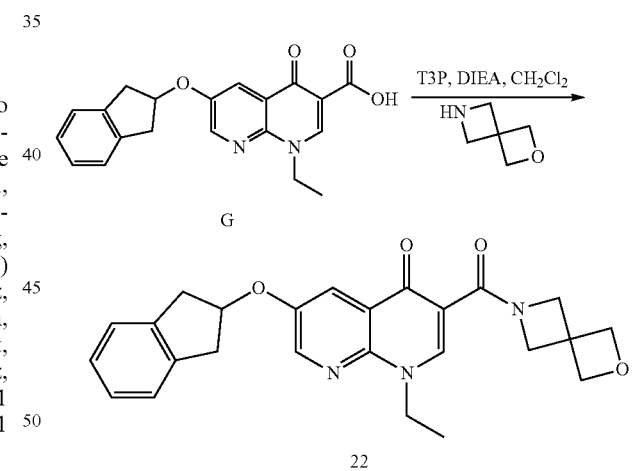

1-Ethyl-6-indan-2-yloxy-4-oxo-1,8-naphthyridine-3-carboxylic acid (300 mg, 0.85 mmol), 2-oxa-6-azaspiro[3.3]heptane (110 mg, 1.11 mmol), propylphosphonic anhydride solution 50 wt. % in ethyl acetate (0.76 ml, 1.28 mmol) and diisopropylethylamine (0.40 ml, 2.55 mmol) were reacted as described under General Procedure A (18 h at RT) to furnish the title compound (60 mg, 16%) as a white foam. $^1$H NMR (300 MHz, DMSO-$d_6$) δ 8.55 (d, J=3.1 Hz, 1H), 8.49 (s, 1H), 8.03 (d, J=3.1 Hz, 1H), 7.28-7.25 (m, 2H), 7.18-7.15 (m, 2H), 5.47-5.41 (m, 1H), 4.69-4.63 (m, 4H), 4.45 (qd, J=6.8 Hz, 2H), 4.27 (s, 2H), 4.15 (s, 2H), 3.43 (dd, J=17.1, 5.9 Hz, 2H), 3.07 (d, J=17.1 Hz, 2H), 1.32 (t, J=7.0 Hz, 3H). ESIMS m/z [M+H]$^+$ 432.2.

Example 23: 1-Ethyl-6-indan-2-yloxy-3-(7-oxa-2-azaspiro[3.5]nonane-2-carbonyl)-1,8-naphthyridin-4-one

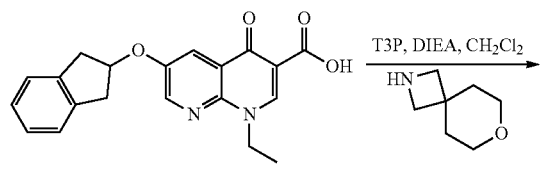

G

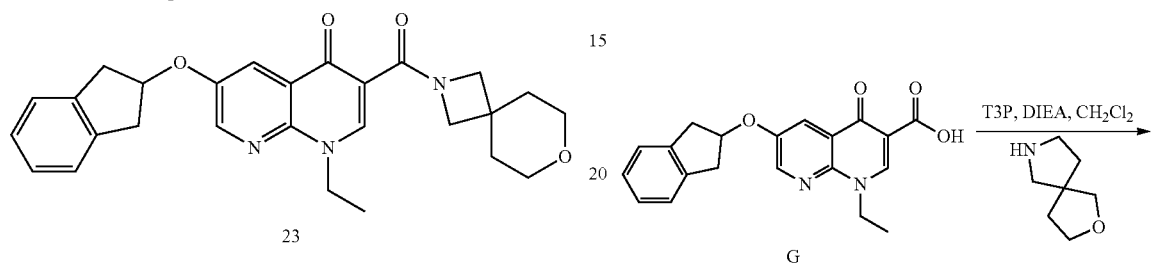

23

1-Ethyl-6-indan-2-yloxy-4-oxo-1,8-naphthyridine-3-carboxylic acid (300 mg, 0.85 mmol), 7-oxa-2-azaspiro[3.5]nonane hydrochloride (182 mg, 1.10 mmol), propylphosphonic anhydride solution 50 wt. % in ethyl acetate (0.76 ml, 1.28 mmol) and diisopropylethylamine (0.60 ml, 3.46 mmol) were reacted as described under General Procedure A (18 h at RT) to furnish the title compound (70 mg, 18%) as a white powder. $^1$H NMR (300 MHz, DMSO-$d_6$) δ 8.55 (d, J=3.1 Hz, 1H), 8.50 (s, 1H), 8.03 (d, J=3.1 Hz, 1H), 7.28-7.25 (m, 2H), 7.18-7.15 (m, 2H), 5.44 (t, J=5.8 Hz, 1H), 4.45 (qd, J=7.0 Hz, 2H), 3.85 (s, 2H), 3.72 (s, 2H), 3.53-3.38 (m, 6H), 3.07 (d, J=16.8 Hz, 2H), 1.65 (t, J=4.9 Hz, 4H), 1.33 (t, J=7.0 Hz, 3H). ESIMS m/z [M+H]$^+$ 460.1.

Example 24: 1-Ethyl-6-indan-2-yloxy-3-(1-oxa-7-azaspiro[4.4]nonane-7-carbonyl)-1,8-naphthyridin-4-one

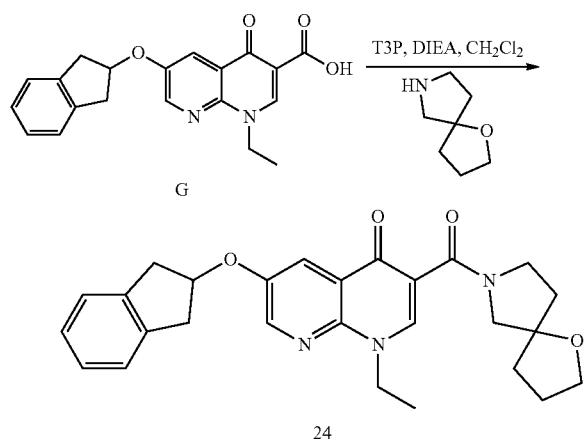

24

1-Ethyl-6-indan-2-yloxy-4-oxo-1,8-naphthyridine-3-carboxylic acid (300 mg, 0.85 mmol), 1-oxa-7-azaspiro[4.4]nonane (141 mg, 1.11 mmol), propylphosphonic anhydride solution 50 wt. % in ethyl acetate (0.76 ml, 1.28 mmol) and diisopropylethylamine (0.44 ml, 2.57 mmol) were reacted as described under General Procedure A (18 h at RT) to furnish the title compound (238 mg, 61%) as a white foam. $^1$H NMR (300 MHz, DMSO-$d_6$) δ 8.55 (d, J=3.1 Hz, 1H), 8.41 (d, J=7.2 Hz, 1H), 8.02 (d, J=3.1 Hz, 1H), 7.28-7.25 (m, 2H), 7.18-7.15 (m, 2H), 5.47-5.41 (m, 1H), 4.43 (qd, J=6.8 Hz, 2H), 3.77-3.36 (m, 7H), 3.26 (d, J=11.6 Hz, 1H), 3.08 (d, J=16.0 Hz, 2H), 1.92-1.80 (m, 6H), 1.33 (t, J=6.9 Hz, 3H). ESIMS m/z [M+H]$^+$ 460.1.

Example 25: 1-Ethyl-6-indan-2-yloxy-3-(2-oxa-7-azaspiro[4.4]nonane-7-carbonyl)-1,8-naphthyridin-4-one

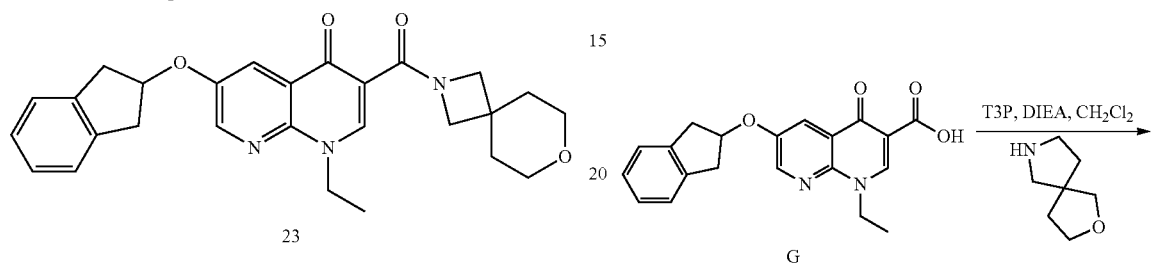

G

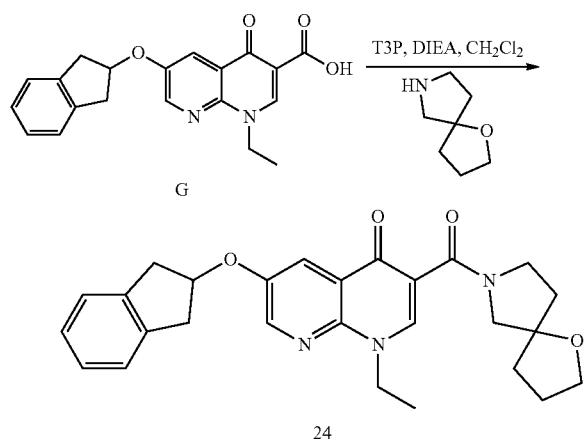

25

1-Ethyl-6-indan-2-yloxy-4-oxo-1,8-naphthyridine-3-carboxylic acid (300 mg, 0.85 mmol), 2-oxa-7-azaspiro[4.4]nonane hydrochloride (182 mg, 1.11 mmol), propylphosphonic anhydride solution 50 wt. % in ethyl acetate (0.76 ml, 1.28 mmol) and diisopropylethylamine (0.58 ml, 3.42 mmol) were reacted as described under General Procedure A (18 h at RT) to furnish the title compound (200 mg, 51%) as a yellow foam. $^1$H NMR (300 MHz, DMSO-$d_6$) δ 8.55 (d, J=3.1 Hz, 1H), 8.40 (s, 1H), 8.03 (d, J=2.0 Hz, 1H), 7.28-7.25 (m, 2H), 7.18-7.15 (m, 2H), 5.47-5.41 (m, 1H), 4.43 (qd, J=6.8 Hz, 2H), 3.79 (t, J=7.0 Hz, 1H), 3.73-3.35 (m, 9H), 3.08 (d, J=17.1 Hz, 2H), 1.97-1.77 (m, 4H), 1.33 (t, J=6.9 Hz, 3H). ESIMS m/z [M+H]$^+$ 460.2.

Example 26: 1-Ethyl-6-indan-2-yloxy-3-(morpholine-4-carbonyl)-1,7-naphthyridin-4-one

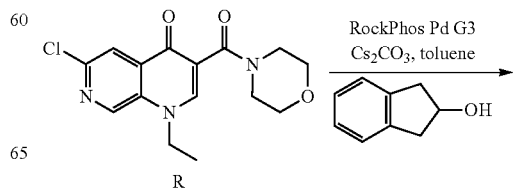

R

-continued

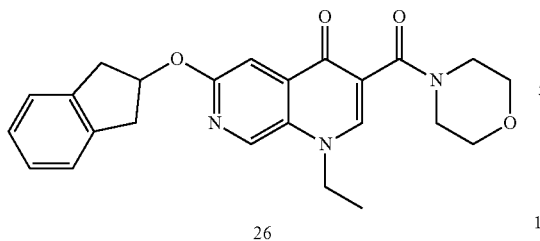

26

6-Chloro-1-ethyl-3-(morpholine-4-carbonyl)-1,7-naphthyridin-4-one (325 mg, 1.01 mmol), 2-indanol (267 mg, 2.02 mmol), cesium carbonate (650 mg, 2.02 mmol) and RockPhos G3 Pd (51 mg, 0.06 mmol) in toluene (10 ml) were reacted as described under General Procedure B (4 days at 130° C.) to furnish the title compound (58 mg, 14%) as a yellow foam. $^1$H NMR (300 MHz, DMSO-$d_6$) δ 9.00 (s, 1H), 8.30 (s, 1H), 7.28 (s, 1H), 7.27-7.24 (m, 2H), 7.17-7.14 (m, 2H), 5.76-5.72 (m, 1H), 4.43 (qd, J=7.0 Hz, 2H), 3.57 (brs, 6H), 3.39 (dd, J=17.0, 6.2 Hz, 2H), 3.23 (brs, 2H), 3.03 (dd, J=17.0, 2.2 Hz, 2H), 1.38 (t, J=7.2 Hz, 3H). ESIMS m/z [M+H]$^+$ 419.9.

Example 27: 1-Ethyl-6-indan-2-yloxy-3-[(2R)-2-methylmorpholine-4-carbonyl]-1,7-naphthyridin-4-one

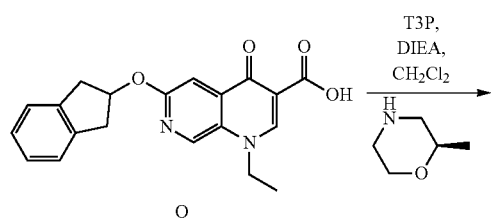

27

1-Ethyl-6-indan-2-yloxy-4-oxo-1,7-naphthyridine-3-carboxylic acid (100 mg, 0.28 mmol), (2R)-2-methylmorpholine (51 mg, 0.37 mmol), propylphosphonic anhydride solution 50 wt. % in ethyl acetate (0.25 ml, 0.43 mmol) and diisopropylethylamine (0.20 ml, 0.56 mmol) were reacted as described under General Procedure A (18 h at RT) to furnish the title compound (64 mg, 52%) as a white foam. $^1$H NMR (300 MHz, DMSO-$d_6$) δ 9.00 (s, 1H), 8.29 (s, 1H), 7.29 (s, 1H), 7.28-7.24 (m, 2H), 7.17-7.14 (m, 2H), 5.76-5.72 (m, 1H), 4.42 (qd, J=7.2 Hz, 2H), 4.29 (t, J=10.1 Hz, 1H), 3.75 (dd, J=47.3, 10.1 Hz, 1H), 3.44-3.36 (m, 4H), 3.04 (d, J=17.0 Hz, 2H), 2.78 (t, J=11.4 Hz, 1H), 1.38 (t, J=7.0 Hz, 3H), 1.11 and 0.94 (2d, J=5.6 Hz, 3H). ESIMS m/z [M+H]$^+$ 434.1.

Example 28: 1-Ethyl-6-indan-2-yloxy-3-[(2R)-2-isopropylmorpholine-4-carbonyl]-1,7-naphthyridin-4-one

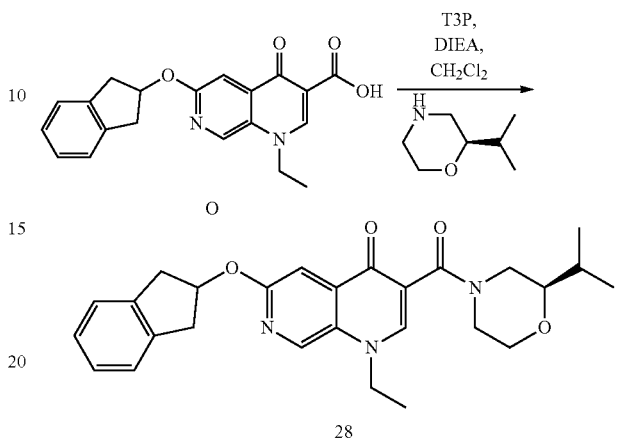

28

1-Ethyl-6-indan-2-yloxy-4-oxo-1,7-naphthyridine-3-carboxylic acid (70 mg, 0.20 mmol), (2R)-2-isopropylmorpholine (35 mg, 0.26 mmol), propylphosphonic anhydride solution 50 wt. % in ethyl acetate (0.18 ml, 0.30 mmol) and diisopropylethylamine (0.10 ml, 0.60 mmol) were reacted as described under General Procedure A (18 h at RT) to furnish the title compound (51 mg, 55%) as a white foam. $^1$H NMR (300 MHz, DMSO-$d_6$) δ 9.01 (s, 1H), 8.29 (s, 1H), 7.28 (s, 1H), 7.27-7.24 (m, 2H), 7.18-7.14 (m, 2H), 5.76-5.73 (m, 1H), 4.42 (qd, J=7.1 Hz, 2H), 4.38-4.24 (m, 1H), 3.82 (dd, J=48.2, 10.6 Hz, 1H), 3.40 (dd, J=16.8, 6.0 Hz, 4H), 3.27-2.63 (m, 5H), 1.73-1.48 (2m, 1H), 1.38 (t, J=7.0 Hz, 3H), 0.91 (t, J=6.2 Hz, 3H), 0.80 and 0.69 (2d, J=6.5 Hz, 3H). ESIMS m/z [M+H]$^+$ 462.1.

Example 29: 3-(2,2-dimethylmorpholine-4-carbonyl)-1-ethyl-6-indan-2-yloxy-1,7-naphthyridin-4-one

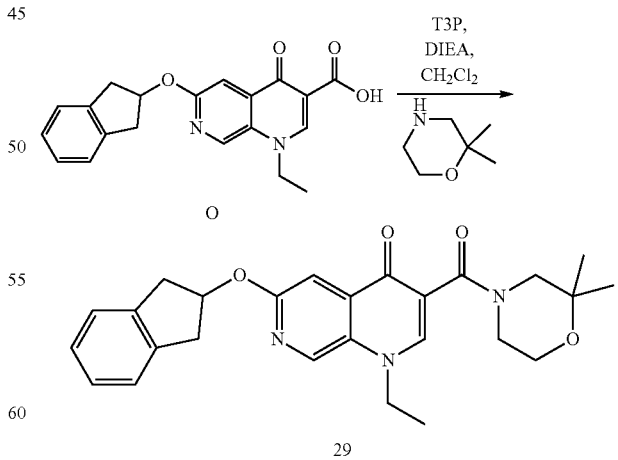

29

1-Ethyl-6-indan-2-yloxy-4-oxo-1,7-naphthyridine-3-carboxylic acid (100 mg, 0.28 mmol), 2,2-dimethylmorpholine (37 mg, 0.37 mmol), propylphosphonic anhydride solution 50 wt. % in ethyl acetate (0.26 ml, 0.43 mmol) and diisopropylethylamine (0.15 ml, 0.86 mmol) were reacted as described under General Procedure A (18 h at RT) to furnish the title compound (105 mg, 82%) as a white foam. ¹H NMR (300 MHz, DMSO-d₆) δ 9.01 (s, 1H), 8.29 (s, 1H), 7.30 (s, 1H), 7.27-7.24 (m, 2H), 7.19-7.14 (m, 2H), 5.76-5.72 (m, 1H), 4.43 (qd, J=6.9 Hz, 2H), 3.62-3.50 (m, 2H), 3.40 (dd, J=16.9, 6.2 Hz, 4H), 3.16 (br s, 2H), 3.06 (d, J=17.2 Hz, 2H), 1.38 (t, J=6.9 Hz, 3H), 1.19 and 1.00 (2s, 6H). ESIMS m/z [M+H]⁺ 448.2.

Example 30: 1-Ethyl-6-indan-2-yloxy-3-(2,2,6,6-tetramethylmorpholine-4-carbonyl)-1,7-naphthyridin-4-one

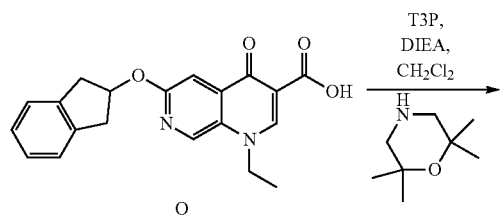

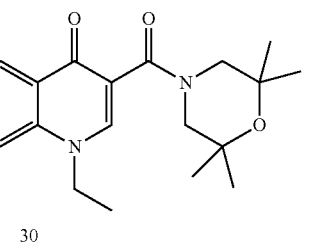

30

1-Ethyl-6-indan-2-yloxy-4-oxo-1,7-naphthyridine-3-carboxylic acid (67 mg, 0.18 mmol), 2,2,6,6-tetramethylmorpholine (34 mg, 0.23 mmol), propylphosphonic anhydride solution 50 wt. % in ethyl acetate (0.17 ml, 0.27 mmol) and diisopropylethylamine (0.10 ml, 0.55 mmol) were reacted as described under General Procedure A (18 h at RT) to furnish the title compound (78 mg, 89%) as a beige foam. ¹H NMR (300 MHz, DMSO-d₆) δ 9.01 (s, 1H), 8.38 (s, 1H), 7.29 (s, 1H), 7.27-7.24 (m, 2H), 7.19-7.15 (m, 2H), 5.77-5.72 (m, 1H), 4.44 (qd, J=7.0 Hz, 2H), 3.40 (dd, J=17.0, 6.5 Hz, 4H), 3.11 (s, 2H), 3.04 (dd, J=17.0, 2.4 Hz, 2H), 1.36 (t, J=6.9 Hz, 3H), 1.17 (s, 6H), 1.04 (s, 6H). ESIMS m/z [M+H]⁺ 476.1.

Example 31: 1-Ethyl-6-indan-2-yloxy-3-[(2R)-2-(methoxymethyl)morpholine-4-carbonyl]-1,7-naphthyridin-4-one

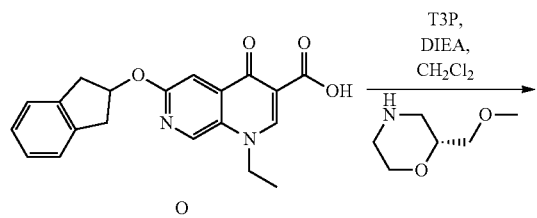

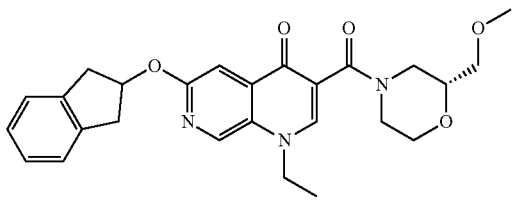

31

1-Ethyl-6-indan-2-yloxy-4-oxo-1,7-naphthyridine-3-carboxylic acid (60 mg, 0.17 mmol), (2R)-2-methoxymethylmorpholine (37 mg, 0.22 mmol), propylphosphonic anhydride solution 50 wt. % in ethyl acetate (0.15 ml, 0.25 mmol) and diisopropylethylamine (0.12 ml, 0.68 mmol) were reacted as described under General Procedure A (18 h at RT) to furnish the title compound (63 mg, 79%) as a white foam. ¹H NMR (300 MHz, DMSO-d₆) δ 9.01 (s, 1H), 8.30 (s, 1H), 7.28 (s, 1H), 7.27-7.24 (m, 2H), 7.19-7.14 (m, 2H), 5.77-5.72 (m, 1H), 4.43 (qd, J=7.1 Hz, 2H), 4.36-4.25 (m, 1H), 3.80 (dd, J=44.6, 9.6 Hz, 1H), 3.62-3.36 (m, 6H), 3.26 (s, 3H), 3.14 (s, 2H), 3.04 (d, J=16.9 Hz, 2H), 2.95-2.80 (m, 1H), 1.38 (t, J=6.9 Hz, 3H). ESIMS m/z [M+H]⁺ 464.1.

Example 32: 3-[(3R,5S)-3,5-dimethylmorpholine-4-carbonyl]-1-ethyl-6-indan-2-yloxy-1,7-naphthyridin-4-one

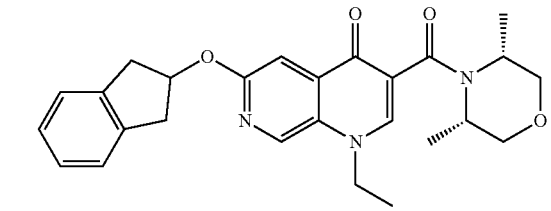

32

1-Ethyl-6-indan-2-yloxy-4-oxo-1,7-naphthyridine-3-carboxylic acid (65 mg, 0.18 mmol), cis-3,5-dimethylmorpholine (0.03 ml, 0.23 mmol), propylphosphonic anhydride solution 50 wt. % in ethyl acetate (0.16 ml, 0.27 mmol) and diisopropylethylamine (0.10 ml, 0.55 mmol) were reacted as described under General Procedure A (18 h at RT) to furnish the title compound (49 mg, 59%) as a white foam. ¹H NMR (300 MHz, DMSO-d₆) δ 9.01 (s, 1H), 8.30 (s, 1H), 7.28 (s, 1H), 7.27-7.24 (m, 2H), 7.19-7.14 (m, 2H), 5.76-5.72 (m, 1H), 4.43 (qd, J=6.9 Hz, 2H), 3.80 (br s, 2H), 3.63 (d, J=11.2 Hz, 2H), 3.49 (dd, J=11.4, 3.4 Hz, 2H), 3.40 (dd, J=17.0, 6.2 Hz, 2H), 3.05 (dd, J=17.0, 2.3 Hz, 2H), 1.37 (t, J=7.0 Hz, 3H), 1.23 (d, J=6.3 Hz, 6H). ESIMS m/z [M+H]⁺ 448.1.

Example 33: 3-[(3R,5R)-3,5-dimethylmorpholine-4-carbonyl]-1-ethyl-6-indan-2-yloxy-1,7-naphthyridin-4-one

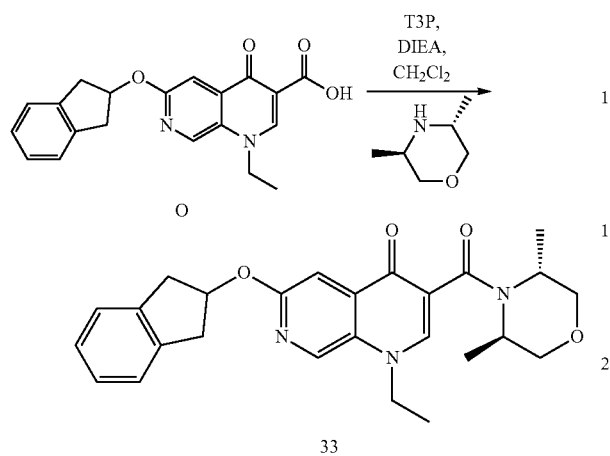

1-Ethyl-6-indan-2-yloxy-4-oxo-1,7-naphthyridine-3-carboxylic acid (60 mg, 0.17 mmol), (3R,5R)-3,5-dimethylmorpholine (35 mg, 0.22 mmol), propylphosphonic anhydride solution 50 wt. % in ethyl acetate (0.16 ml, 0.26 mmol) and diisopropylethylamine (0.09 ml, 0.51 mmol) were reacted as described under General Procedure A (18 h at RT) to furnish the title compound (54 mg, 70%) as a white foam. $^{1}$H NMR (300 MHz, DMSO-$d_6$) δ 9.01 (s, 1H), 8.32 (s, 1H), 7.29 (s, 1H), 7.27-7.24 (m, 2H), 7.17-7.14 (m, 2H), 5.76-5.72 (m, 1H), 4.44 (qd, J=6.9 Hz, 2H), 3.83-3.70 (m, 4H), 3.44-3.36 (m, 4H), 3.05 (dd, J=16.8, 2.5 Hz, 2H), 1.38 (t, J=7.0 Hz, 3H), 1.18 (d, J=6.9 Hz, 6H). ESIMS m/z [M+H]$^{+}$ 448.1.

Example 34: 3-(3,3-dimethylmorpholine-4-carbonyl)-1-ethyl-6-indan-2-yloxy-1,7-naphthyridin-4-one

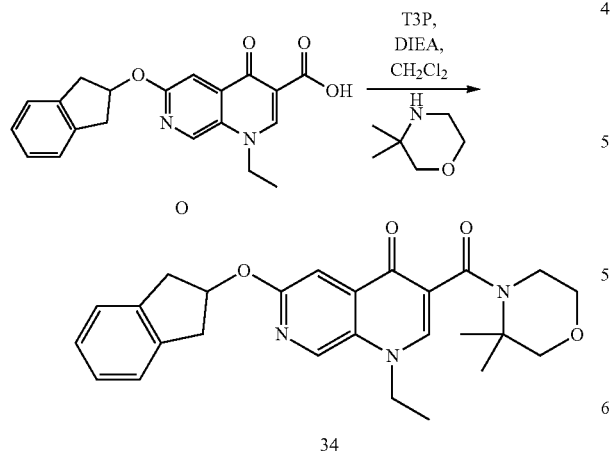

1-Ethyl-6-indan-2-yloxy-4-oxo-1,7-naphthyridine-3-carboxylic acid (60 mg, 0.17 mmol), 3,3-dimethylmorpholine (25 mg, 0.22 mmol), propylphosphonic anhydride solution 50 wt. % in ethyl acetate (0.15 ml, 0.25 mmol) and diisopropylethylamine (0.12 ml, 0.51 mmol) were reacted as described under General Procedure A (18 h at RT) to furnish the title compound (5 mg, 6%) as a white foam. $^{1}$H NMR (300 MHz, DMSO-$d_6$) δ 8.99 (s, 1H), 8.26 (s, 1H), 7.28 (s, 1H), 7.26-7.24 (m, 2H), 7.17-7.14 (m, 2H), 5.76-5.72 (m, 1H), 4.43 (qd, J=7.2 Hz, 2H), 3.64 (t, J=4.5 Hz, 2H), 3.39 (dd, J=17.1, 6.2 Hz, 4H), 3.25-3.21 (m, 2H), 3.04 (dd, J=17.0, 2.5 Hz, 2H), 1.38 (s, 6H), 1.37 (t, J=6.9 Hz, 3H). ESIMS m/z [M+H]$^{+}$ 448.1.

Example 35: 1-ethyl-6-indan-2-yloxy-3-[(3S)-3-(methoxymethyl)morpholine-4-carbonyl]-1,7-naphthyridin-4-one

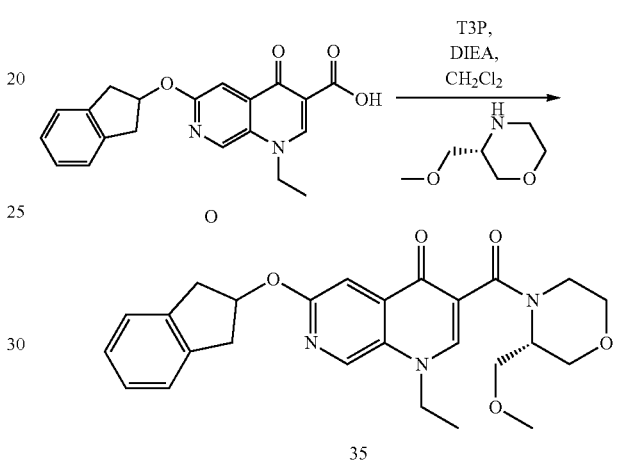

1-Ethyl-6-indan-2-yloxy-4-oxo-1,7-naphthyridine-3-carboxylic acid (60 mg, 0.17 mmol), (S)-3-methoxymethylmorpholine hydrochloride (40 mg, 0.22 mmol), propylphosphonic anhydride solution 50 wt. % in ethyl acetate (0.16 ml, 0.26 mmol) and diisopropylethylamine (0.12 ml, 0.68 mmol) were reacted as described under General Procedure A (48 h at RT) to furnish the title compound (57 mg, 72%) as a white foam. $^{1}$H NMR (300 MHz, DMSO-$d_6$) δ 9.01 (s, 1H), 8.25 (d, J=12.3 Hz, 1H), 7.28 (s, 1H), 7.27-7.24 (m, 2H), 7.19-7.14 (m, 2H), 5.76-5.72 (m, 1H), 4.43 (qd, J=6.2 Hz, 2H), 4.42-4.06 (m, 1H), 3.90-3.82 (m, 1H), 3.70-3.46 (m, 3H), 3.39 (dd, J=17.0, 6.1 Hz, 4H), 3.36-3.15 (m, 3H), 3.10-3.01 (m, 4H), 1.38 (t, J=6.8 Hz, 3H). ESIMS m/z [M+H]$^{+}$ 464.1.

Example 36: 3-[trans-2,5-dimethylmorpholine-4-carbonyl]-1-ethyl-6-indan-2-yloxy-1,7-naphthyridin-4-one

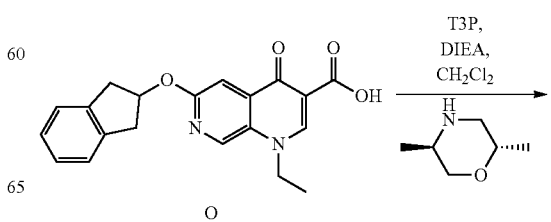

-continued

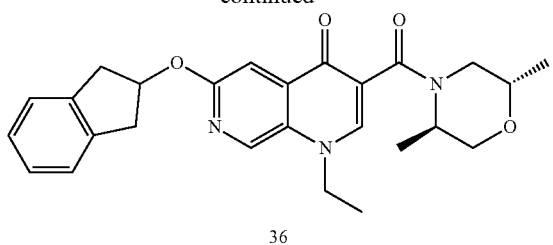

36

1-Ethyl-6-indan-2-yloxy-4-oxo-1,7-naphthyridine-3-carboxylic acid (60 mg, 0.17 mmol), trans-2,5-dimethylmorpholine (35 mg, 0.22 mmol), propylphosphonic anhydride solution 50 wt. % in ethyl acetate (0.16 ml, 0.26 mmol) and diisopropylethylamine (0.09 ml, 0.51 mmol) were reacted as described under General Procedure A (48 h at RT) to furnish the title compound (51 mg, 66%) as a white foam. ¹H NMR (300 MHz, DMSO-d₆) δ 9.01 (s, 1H), 8.27 (s, 1H), 7.29 (s, 1H), 7.27-7.24 (m, 2H), 7.17-7.14 (m, 2H), 5.76-5.72 (m, 1H), 4.42 (qd, J=7.1 Hz, 2H), 3.96-3.85 (m, 2H), 3.39 (dd, J=17.1, 6.1 Hz, 4H), 3.25 (d, J=11.6 Hz, 2H), 3.04 (dd, J=16.9, 2.9 Hz, 2H), 1.37 (t, J=7.0 Hz, 3H), 1.19 (d, J=6.8 Hz, 3H), 1.15 (d, J=6.4 Hz, 3H). ESIMS m/z [M+H]⁺ 448.1.

Example 37: 3-[(2R,5R)-2,5-dimethylmorpholine-4-carbonyl]-1-ethyl-6-indan-2-yloxy-1,7-naphthyridin-4-one

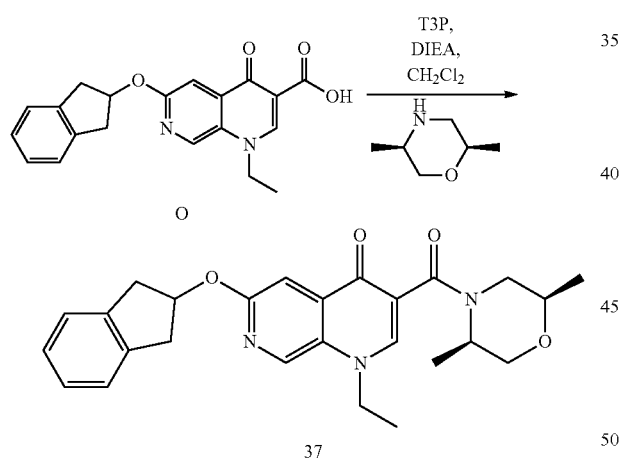

37

1-Ethyl-6-indan-2-yloxy-4-oxo-1,7-naphthyridine-3-carboxylic acid (100 mg, 0.28 mmol), (2R,5R)-2,5-dimethylmorpholine hydrochloride (56 mg, 0.37 mmol), propylphosphonic anhydride solution 50 wt. % in ethyl acetate (0.26 ml, 0.43 mmol) and diisopropylethylamine (0.20 ml, 1.12 mmol) were reacted as described under General Procedure A (18 h at RT) to furnish the title compound (80 mg, 63%) as a white foam. ¹H NMR (300 MHz, DMSO-d₆) δ 9.00 (s, 1H), 8.27 (s, 1H), 7.28 (s, 1H), 7.27-7.24 (m, 2H), 7.18-7.14 (m, 2H), 5.76-5.72 (m, 1H), 4.42 (qd, J=6.9 Hz, 2H), 4.41-4.14 (m, 1H), 3.68-3.48 (m, 2H), 3.40 (dd, J=17.0, 6.1 Hz, 4H), 3.19-2.91 (m, 3H), 1.38 (t, J=7.0 Hz, 3H), 1.21-0.97 (m, 6H), 1.15 (d, J=6.4 Hz, 3H). ESIMS m/z [M+H]⁺ 448.1.

Example 38: 1-Ethyl-6-indan-2-yloxy-3-(6-oxa-3-azabicyclo[3.1.1]heptane-3-carbonyl)-1,7-naphthyridin-4-one

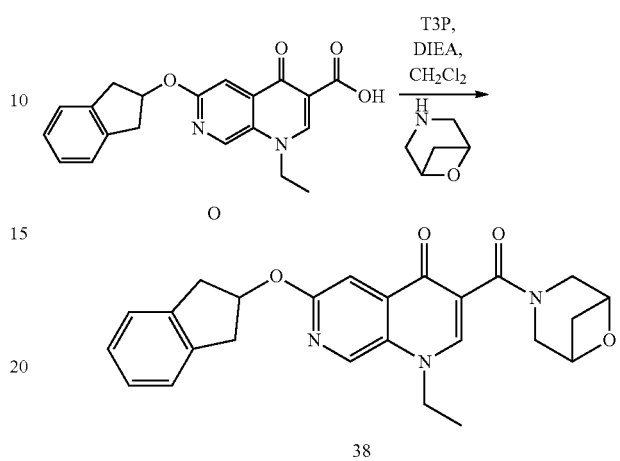

38

1-Ethyl-6-indan-2-yloxy-4-oxo-1,7-naphthyridine-3-carboxylic acid (75 mg, 0.21 mmol), 6-oxa-3-azabicyclo[3.1.1]heptane tosylate (76 mg, 0.28 mmol), propylphosphonic anhydride solution 50 wt. % in ethyl acetate (0.19 ml, 0.32 mmol) and diisopropylethylamine (0.15 ml, 0.84 mmol) were reacted as described under General Procedure A (72 h at RT) to furnish the title compound (51 mg, 56%) as a white foam. ¹H NMR (300 MHz, DMSO-d₆) δ 9.02 (s, 1H), 8.32 (s, 1H), 7.30 (s, 1H), 7.27-7.24 (m, 2H), 7.17-7.14 (m, 2H), 5.77-5.72 (m, 1H), 4.61 (br s, 1H), 4.47-4.40 (m, 3H), 3.84 (d, J=13.7 Hz, 1H), 3.70 (d, J=12.8 Hz, 1H), 3.58-3.49 (m, 2H), 3.40 (dd, J=17.0, 6.2 Hz, 2H), 3.08-3.01 (m, 3H), 1.80 (d, J=8.6 Hz, 1H), 1.39 (t, J=7.0 Hz, 3H). ESIMS m/z [M+H]⁺ 432.1.

Example 39: 1-Ethyl-6-indan-2-yloxy-3-[(1R,4R)-2-oxa-5-azabicyclo[2.2.1]heptane-5-carbonyl]-1,7-naphthyridin-4-one

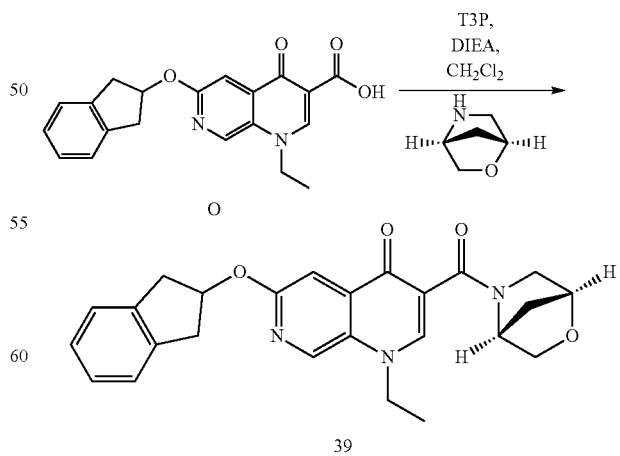

39

1-Ethyl-6-indan-2-yloxy-4-oxo-1,7-naphthyridine-3-carboxylic acid (60 mg, 0.17 mmol), (1R,4R)-2-oxa-5-azabicyclo[2.2.1]heptane hydrochloride (30 mg, 0.22 mmol), propylphosphonic anhydride solution 50 wt. % in ethyl acetate (0.15 ml, 0.25 mmol) and diisopropylethylamine (0.12 ml, 0.68 mmol) were reacted as described under General Procedure A (20 h at RT) to furnish the title compound (51 mg, 69%) as a white powder. $^1$H NMR (300 MHz, DMSO-d$_6$) δ 9.01 and 9.00 (2s, 1H), 8.34 and 8.33 (2s, 1H), 7.31 (s, 1H), 7.29-7.24 (m, 2H), 7.19-7.15 (m, 2H), 5.77-5.72 (m, 1H), 4.78 and 4.60 (2s, 1H), 4.54 and 4.22 (2s, 1H), 4.44 (qd, J=6.9 Hz, 2H), 3.91-3.37 (m, 5H), 3.28-3.15 (m, 2H), 3.05 (d, J=16.9 Hz, 2H), 1.79 and 1.74 (2s, 1H), 1.39 (t, J=6.9 Hz, 3H). ESIMS m/z [M+H]$^+$ 432.1.

Example 40: 1-Ethyl-6-indan-2-yloxy-3-(3-oxa-8-azabicyclo[3.2.1]octane-8-carbonyl)-1,7-naphthyridin-4-one

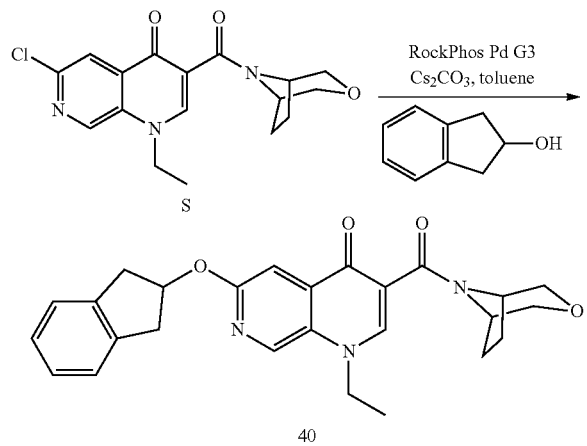

6-Chloro-1-ethyl-3-(3-oxa-8-azabicyclo[3.2.1]octane-8-carbonyl)-1,7-naphthyridin-4-one (128 mg, 0.37 mmol), 2-indanol (99 mg, 0.74 mmol), cesium carbonate (240 mg, 0.74 mmol) and RockPhos G3 Pd (19 mg, 0.02 mmol) in toluene (5 ml) were reacted as described under General Procedure B (18 h at 80° C.) to furnish the title compound (18 mg, 11%) as a white foam. $^1$H NMR (300 MHz, DMSO-d$_6$) δ 9.00 (s, 1H), 8.36 (s, 1H), 7.30 (s, 1H), 7.27-7.24 (m, 2H), 7.17-7.14 (m, 2H), 5.77-5.72 (m, 1H), 4.50-4.41 (m, 3H), 3.77 (brs, 1H), 3.63-3.58 (m, 3H), 3.46-3.36 (m, 3H), 3.04 (d, J=17.0 Hz, 2H), 1.93-1.75 (m, 4H), 1.39 (t, J=7.0 Hz, 3H). ESIMS m/z [M+H]$^+$ 446.1.

Example 41: 1-Ethyl-6-indan-2-yloxy-3-(8-oxa-3-azabicyclo[3.2.1]octane-3-carbonyl)-1,7-naphthyridin-4-one

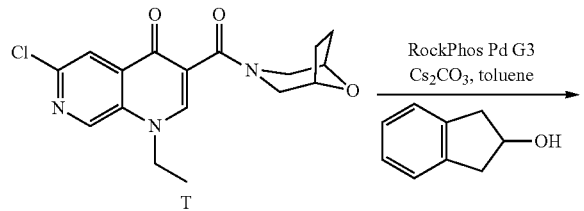

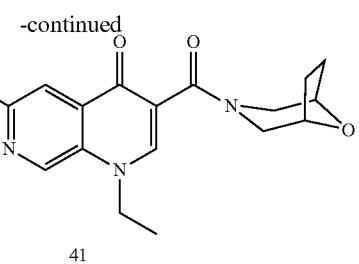

6-Chloro-1-ethyl-3-(8-oxa-3-azabicyclo[3.2.1]octane-8-carbonyl)-1,7-naphthyridin-4-one (410 mg, 1.18 mmol), 2-indanol (316 mg, 2.35 mmol), cesium carbonate (766 mg, 2.35 mmol) and RockPhos G3 Pd (60 mg, 0.07 mmol) in toluene (15 ml) were reacted as described under General Procedure B (72 h at 80° C.) to furnish the title compound (100 mg, 19%) as a yellow foam. $^1$H NMR (300 MHz, DMSO-d$_6$) δ 9.00 (s, 1H), 8.29 (s, 1H), 7.28 (s, 1H), 7.27-7.24 (m, 2H), 7.17-7.14 (m, 2H), 5.77-5.71 (m, 1H), 4.43 (qd, J=7.1 Hz, 2H), 4.34 (brs, 1H), 4.18-4.05 (m, 2H), 3.39 (dd, J=17.1, 5.9 Hz, 2H), 3.24-3.11 (m, 2H), 3.05 (d, J=17.0 Hz, 2H), 2.89 (d, J=12.6 Hz, 1H), 1.94-1.89 (m, 1H), 1.84-1.62 (m, 3H), 1.38 (t, J=7.0 Hz, 3H). ESIMS m/z [M+H]$^+$ 446.1.

Example 42: 1-Ethyl-6-indan-2-yloxy-3-(3-oxa-9-azabicyclo[3.3.1]nonane-9-carbonyl)-1,7-naphthyridin-4-one

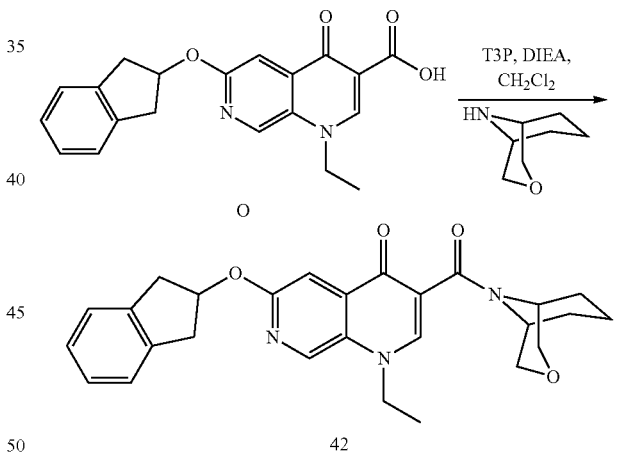

1-Ethyl-6-indan-2-yloxy-4-oxo-1,7-naphthyridine-3-carboxylic acid (75 mg, 0.21 mmol), 3-oxa-9-azabicyclo[3.3.1]nonane hydrochloride (46 mg, 0.28 mmol), propylphosphonic anhydride solution 50 wt. % in ethyl acetate (0.19 ml, 0.32 mmol) and diisopropylethylamine (0.15 ml, 0.84 mmol) were reacted as described under General Procedure A (72 h at RT) to furnish the title compound (48 mg, 50%) as a white foam. $^1$H NMR (300 MHz, DMSO-d$_6$) δ 9.00 (s, 1H), 8.31 (s, 1H), 7.28 (s, 1H), 7.27-7.24 (m, 2H), 7.17-7.14 (m, 2H), 5.76-5.71 (m, 1H), 4.43 (qd, J=7.1 Hz, 2H), 4.37 (brs, 1H), 3.89 (d, J=11.2 Hz, 1H), 3.79-3.72 (m, 2H), 3.64 (d, J=10.5 Hz, 1H), 3.39 (dd, J=16.8, 5.9 Hz, 2H), 3.04 (d, J=17.0 Hz, 2H), 2.48-2.32 (m, 2H), 1.90-1.75 (m, 3H), 1.74-1.65 (m, 1H), 1.58-1.50 (m, 1H), 1.38 (t, J=7.0 Hz, 3H). ESIMS m/z [M+H]$^+$ 460.2.

Example 43: 1-Ethyl-6-indan-2-yloxy-3-(3-oxa-7-azabicyclo[3.3.1]nonane-7-carbonyl)-1,7-naphthyridin-4-one

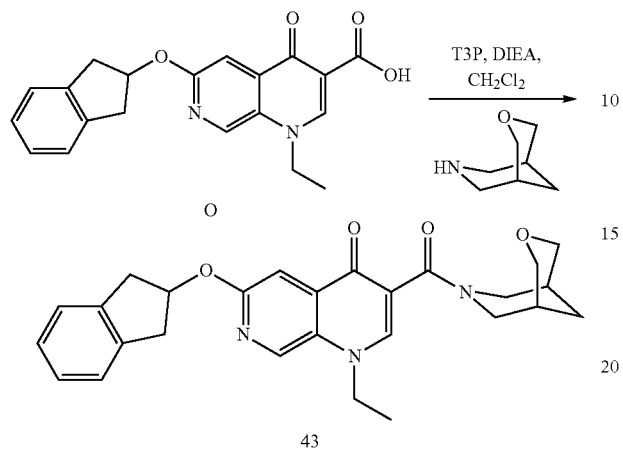

43

1-Ethyl-6-indan-2-yloxy-4-oxo-1,7-naphthyridine-3-carboxylic acid (60 mg, 0.17 mmol), 3-oxa-7-azabicyclo[3.3.1]nonane (30 mg, 0.22 mmol), propylphosphonic anhydride solution 50 wt. % in ethyl acetate (0.16 ml, 0.26 mmol) and diisopropylethylamine (0.09 ml, 0.51 mmol) were reacted as described under General Procedure A (18 h at RT) to furnish the title compound (71 mg, 90%) as a white foam. $^1$H NMR (300 MHz, DMSO-$d_6$) δ 9.00 (s, 1H), 8.04 (s, 1H), 7.28 (s, 1H), 7.27-7.24 (m, 2H), 7.17-7.14 (m, 2H), 5.77-5.72 (m, 1H), 4.67 (d, J=13.3 Hz, 2H), 4.44 (qd, J=7.1 Hz, 2H), 3.84 (d, J=11.1 Hz, 2H), 3.68-3.51 (m, 4H), 3.40 (dd, J=17.0, 6.2 Hz, 2H), 3.40-3.37 (m, 1H), 3.10-2.93 (m, 3H), 1.84 (brs, 2H), 1.73 (brs, 1H), 1.54 (brs, 1H), 1.36 (t, J=7.0 Hz, 3H). ESIMS m/z [M+H]$^+$ 460.2.

Example 44: 1-Ethyl-6-indan-2-yloxy-3-(2-oxa-6-azaspiro[3.3]heptane-6-carbonyl)-1,7-naphthyridin-4-one

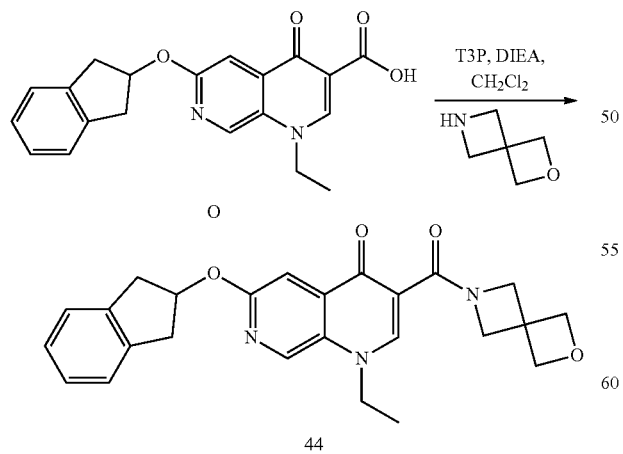

44

1-Ethyl-6-indan-2-yloxy-4-oxo-1,7-naphthyridine-3-carboxylic acid (100 mg, 0.28 mmol), 2-oxa-6-azaspiro[3.3]heptane (37 mg, 0.37 mmol), propylphosphonic anhydride solution 50 wt. % in ethyl acetate (0.26 ml, 0.43 mmol) and diisopropylethylamine (0.15 ml, 0.86 mmol) were reacted as described under General Procedure A (18 h at RT) to furnish the title compound (63 mg, 51%) as a white foam. $^1$H NMR (300 MHz, DMSO-$d_6$) δ 9.00 (s, 1H), 8.37 (s, 1H), 7.30 (s, 1H), 7.27-7.24 (m, 2H), 7.19-7.15 (m, 2H), 5.78-5.72 (m, 1H), 4.65-4.60 (m, 4H), 4.44 (qd, J=6.9 Hz, 2H), 4.21 (s, 2H), 4.12 (s, 2H), 3.40 (dd, J=17.0, 6.1 Hz, 2H), 3.05 (dd, J=17.0, 2.4 Hz, 2H), 1.38 (t, J=7.0 Hz, 3H). ESIMS m/z [M+H]$^+$ 432.1.

Example 45: 1-Ethyl-6-indan-2-yloxy-3-(7-oxa-2-azaspiro[3.5]nonane-2-carbonyl)-1,7-naphthyridin-4-one

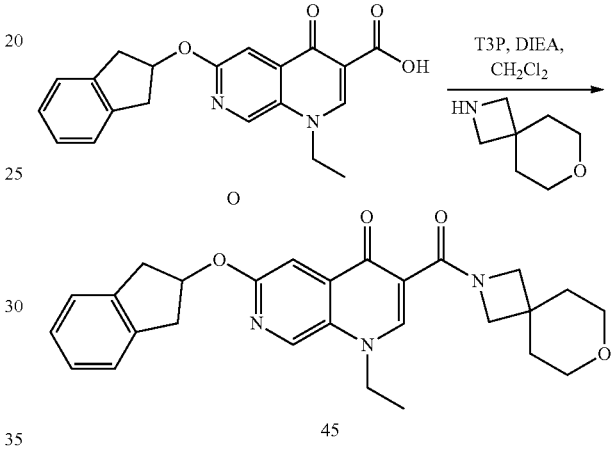

45

1-Ethyl-6-indan-2-yloxy-4-oxo-1,7-naphthyridine-3-carboxylic acid (64 mg, 0.18 mmol), 7-oxa-2-azaspiro[3.5]nonane hydrochloride (37 mg, 0.23 mmol), propylphosphonic anhydride solution 50 wt. % in ethyl acetate (0.16 ml, 0.27 mmol) and diisopropylethylamine (0.13 ml, 0.73 mmol) were reacted as described under General Procedure A (18 h at RT) to furnish the title compound (29 mg, 34%) as a white foam. $^1$H NMR (300 MHz, DMSO-$d_6$) δ 9.00 (s, 1H), 8.39 (s, 1H), 7.30 (s, 1H), 7.27-7.24 (m, 2H), 7.17-7.15 (m, 2H), 5.77-5.71 (m, 1H), 4.45 (qd, J=7.0 Hz, 2H), 3.80 (s, 2H), 3.69 (s, 2H), 3.54-3.32 (m, 6H), 3.05 (d, J=17.0 Hz, 2H), 1.63 (t, J=4.8 Hz, 4H), 1.38 (t, J=7.1 Hz, 3H). ESIMS m/z [M+H]$^+$ 460.1.

Example 46: 1-Ethyl-6-indan-2-yloxy-3-(1-oxa-7-azaspiro[4.4]nonane-7-carbonyl)-1,7-naphthyridin-4-one

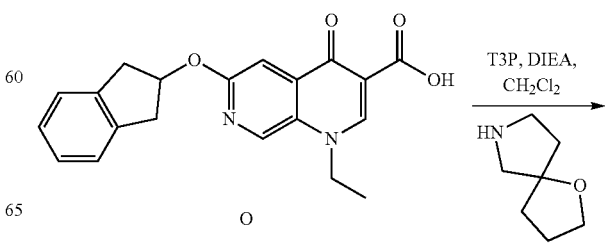

-continued

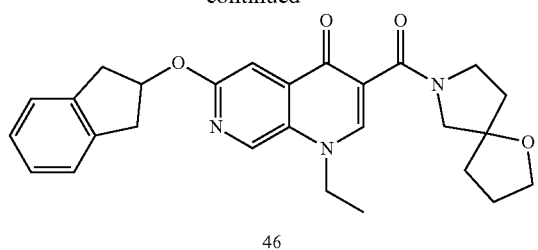

46

1-Ethyl-6-indan-2-yloxy-4-oxo-1,7-naphthyridine-3-carboxylic acid (70 mg, 0.20 mmol), 1-oxa-7-azaspiro[4.4]nonane (35 mg, 0.26 mmol), propylphosphonic anhydride solution 50 wt. % in ethyl acetate (0.18 ml, 0.30 mmol) and diisopropylethylamine (0.11 ml, 0.60 mmol) were reacted as described under General Procedure A (18 h at RT) to furnish the title compound (59 mg, 64%) as a white foam. $^1$H NMR (300 MHz, DMSO-$d_6$) δ 9.00 (s, 1H), 8.29 (d, J=7.7 Hz, 1H), 7.29 (s, 1H), 7.27-7.24 (m, 2H), 7.19-7.15 (m, 2H), 5.77-5.72 (m, 1H), 4.43 (qd, J=7.1 Hz, 2H), 3.77-3.36 (m, 7H), 3.19 (d, J=11.1 Hz, 1H), 3.04 (d, J=17.0 Hz, 2H), 1.94-1.70 (m, 6H), 1.38 (t, J=6.8 Hz, 3H). ESIMS m/z [M+H]$^+$ 460.1.

Example 47: 1-Ethyl-6-indan-2-yloxy-3-(2-oxa-7-azaspiro[4.4]nonane-7-carbonyl)-1,7-naphthyridin-4-one

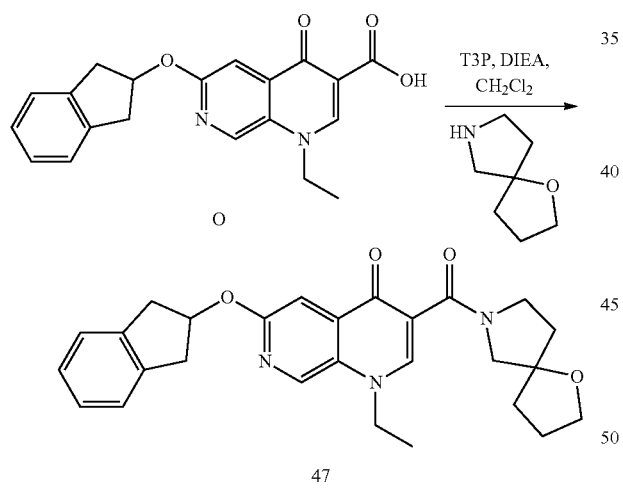

47

1-Ethyl-6-indan-2-yloxy-4-oxo-1,7-naphthyridine-3-carboxylic acid (70 mg, 0.20 mmol), 2-oxa-7-azaspiro[4.4]nonane hydrochloride (43 mg, 0.26 mmol), propylphosphonic anhydride solution 50 wt. % in ethyl acetate (0.18 ml, 0.30 mmol) and diisopropylethylamine (0.14 ml, 0.80 mmol) were reacted as described under General Procedure A (18 h at RT) to furnish the title compound (53 mg, 58%) as a white foam. $^1$H NMR (300 MHz, DMSO-$d_6$) δ 9.00 (s, 1H), 8.30 (s, 1H), 7.30 (s, 1H), 7.27-7.24 (m, 2H), 7.17-7.14 (m, 2H), 5.77-5.71 (m, 1H), 4.43 (qd, J=7.1 Hz, 2H), 3.77 (t, J=7.0 Hz, 1H), 3.69-3.36 (m, 9H), 3.05 (d, J=16.8 Hz, 2H), 1.87-1.77 (m, 4H), 1.38 (t, J=7.0 Hz, 3H). ESIMS m/z [M+H]$^+$ 460.1.

Example 48: 1-Ethyl-6-indan-2-yloxy-3-(morpholine-4-carbonyl)-1,5-naphthyridin-4-one

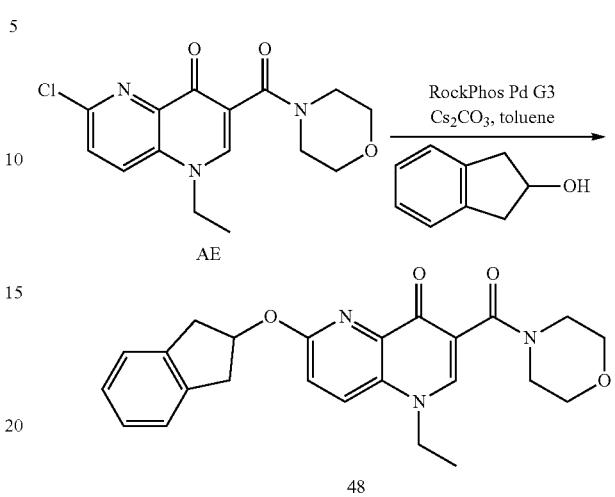

48

6-Chloro-1-ethyl-3-(morpholine-4-carbonyl)-1,5-naphthyridin-5-one (440 mg, 1.36 mmol), 2-indanol (367 mg, 2.73 mmol), cesium carbonate (887 mg, 2.73 mmol) and RockPhos G3 Pd (70 mg, 0.08 mmol) in toluene (13 ml) were reacted as described under General Procedure B (18 h at 80° C.) to furnish the title compound (71 mg, 13%) as a brown foam. $^1$H NMR (300 MHz, DMSO-$d_6$) δ 8.23 (d, J=9.0 Hz, 1H), 8.21 (s, 1H), 7.27-7.24 (m, 2H), 7.18 (d, J=9.0 Hz, 1H), 7.17-7.14 (m, 2H), 5.95-5.90 (m, 1H), 4.32 (qd, J=6.8 Hz, 2H), 3.60 (brs, 6H), 3.43 (dd, J=17.1, 6.4 Hz, 2H), 3.27 (brs, 2H), 3.13 (dd, J=16.9, 3.0 Hz, 2H), 1.30 (t, J=7.0 Hz, 3H). ESIMS m/z [M+H]$^+$ 420.1.

Example 49: 1-Ethyl-6-indan-2-yloxy-3-[(1R,4R)-2-oxa-5-azabicyclo[2.2.1]heptane-5-carbonyl]-1,5-naphthyridin-4-one

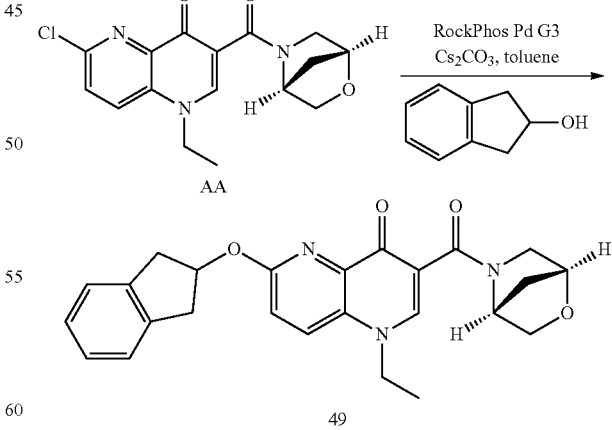

49

6-Chloro-1-ethyl-3-[(1R,4R)-2-oxa-5-azabicyclo[2.2.1]heptane-5-carbonyl]-1,5-naphthyridin-5-one (189 mg, 0.57 mmol), 2-indanol (152 mg, 1.13 mmol), cesium carbonate (369 mg, 1.13 mmol) and RockPhos G3 Pd (28 mg, 0.03 mmol) in toluene (7 ml) were reacted as described under General Procedure B (18 h at 80° C.) to furnish the title compound (18 mg, 6%) as a white foam. $^1$H NMR (300 MHz, DMSO-d$_6$) δ 8.27-8.20 (m, 2H), 7.27-7.24 (m, 2H), 7.16 (s, 1H), 7.17-7.14 (m, 2H), 5.96-5.88 (m, 1H), 4.81 and 4.62 (2s, 1H), 4.57 and 4.26 (2s, 1H), 4.33 (qd, J=7.1 Hz, 2H), 3.94-3.40 (m, 5H), 3.26-3.16 (m, 1H), 3.02 (d, J=17.1 Hz, 2H), 1.80 and 1.76 (2s, 1H), 1.30 (t, J=6.8 Hz, 3H). ESIMS m/z [M+H]$^+$ 432.1.

Example 50: 1-Ethyl-6-indan-2-yloxy-3-(8-oxa-3-azabicyclo[3.2.1]octane-3-carbonyl)-1,5-naphthyridin-4-one

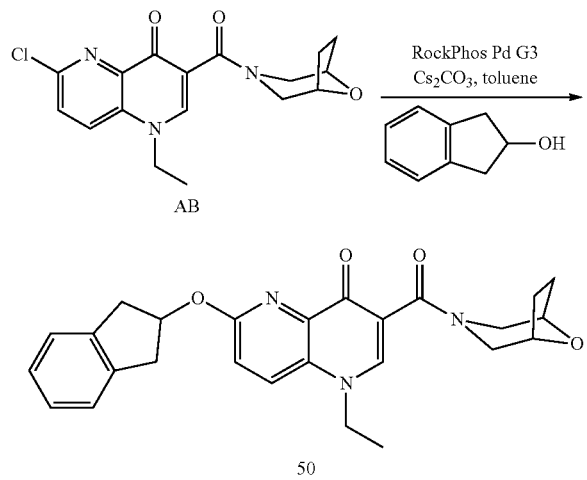

6-Chloro-1-ethyl-3-(8-oxa-3-azabicyclo[3.2.1]octane-8-carbonyl)-1,5-naphthyridin-4-one (385 mg, 1.11 mmol), 2-indanol (300 mg, 2.24 mmol), cesium carbonate (720 mg, 2.21 mmol) and RockPhos G3 Pd (55 mg, 0.06 mmol) in toluene (10 ml) were reacted as described under General Procedure B (16 h at 80° C.) to furnish the title compound (55 mg, 11%) as a pale orange solid. $^1$H NMR (300 MHz, DMSO-d$_6$) δ 8.27-8.22 (m, 2H), 7.29-7.27 (m, 2H), 7.18 (s, 1H), 7.19-7.15 (m, 2H), 5.96-5.90 (m, 1H), 4.40-4.10 (m, 5H), 3.45 (dd, J=17.0, 6.3 Hz, 2H), 3.28-3.18 (m, 2H), 3.04 (d, J=16.6 Hz, 2H), 2.93 (d, J=12.6 Hz, 1H), 2.03-1.96 (m, 1H), 1.86-1.69 (m, 3H), 1.31 (t, J=7.0 Hz, 3H). ESIMS m/z [M+H]$^+$ 446.1.

Example 51: 1-Ethyl-6-indan-2-yloxy-3-(3-oxa-7-azabicyclo[3.3.1]nonane-7-carbonyl)-1,5-naphthyridin-4-one

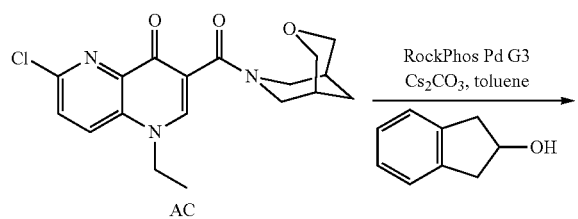

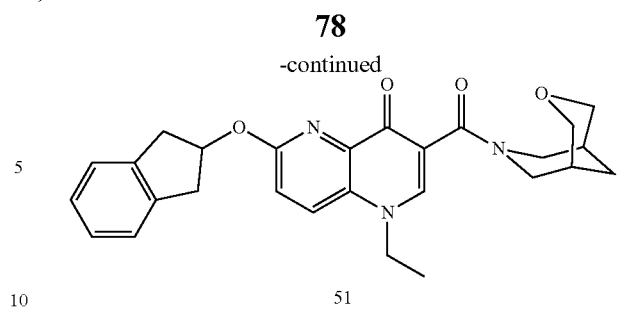

6-Chloro-1-ethyl-3-(3-oxa-7-azabicyclo[3.3.1]octane-7-carbonyl)-1,5-naphthyridin-4-one (650 mg, 1.8 mmol), 2-indanol (483 mg, 3.6 mmol), cesium carbonate (1.17 g, 3.6 mmol) and RockPhos G3 Pd (91 mg, 0.11 mmol) in toluene (15 ml) were reacted as described under General Procedure B (16 h at 80° C.) to furnish the title compound (30 mg, 3%) as a white foam. $^1$H NMR (300 MHz, DMSO-d$_6$) δ 8.23 (d, J=9.3 Hz, 1H), 7.95 (s, 1H), 7.27-7.24 (m, 2H), 7.19-7.14 (m, 3H), 5.94-5.86 (m, 1H), 4.69 (d, J=12.7 Hz, 1H), 4.34 (qd, J=7.1 Hz, 2H), 3.85 (d, J=12.7 Hz, 1H), 3.69-3.39 (m, 7H), 3.06-2.97 (m, 3H), 1.86 (brs, 2H), 1.74 (brs, 1H), 1.57 (brs, 1H), 1.28 (t, J=6.9 Hz, 3H). ESIMS m/z [M+H]$^+$ 460.1.

Example 52: 8-Ethyl-3-indan-2-yloxy-6-(morpholine-4-carbonyl)pyrido[2,3-c]pyridazin-5-one

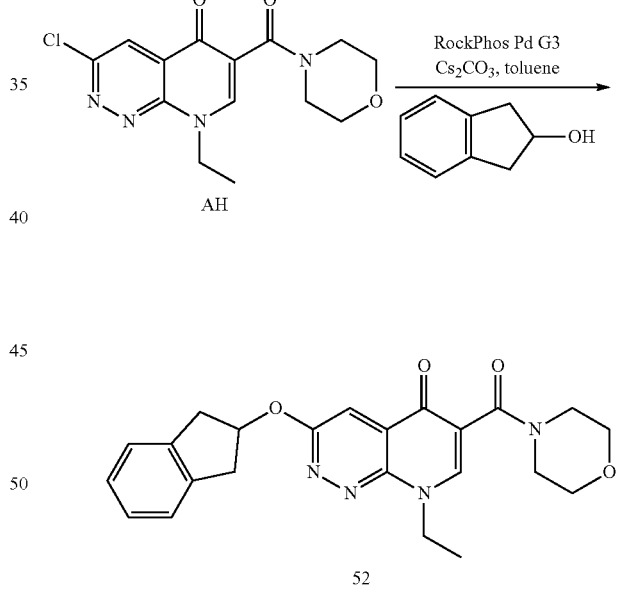

3-Chloro-8-ethyl-6-(morpholine-4-carbonyl)pyrido[2,3-c]pyridazin-5-one (228 mg, 0.70 mmol), 2-indanol (281 mg, 2.12 mmol), cesium carbonate (460 mg, 1.41 mmol) and RockPhos G3 Pd (12 mg, 0.04 mmol) in toluene (7 ml) were reacted as described under General Procedure B (48 h at 120° C.) to furnish the title compound (47 mg, 15%) as a yellow foam. $^1$H NMR (300 MHz, DMSO-d$_6$) δ 8.54 (s, 1H), 7.60 (s, 1H), 7.29-7.26 (m, 2H), 7.18-7.15 (m, 2H), 6.00-5.95 (m, 1H), 4.56 (qd, J=6.9 Hz, 2H), 3.58 (brs, 6H), 3.47 (dd, J=17.2, 6.2 Hz, 2H), 3.25 (brs, 2H), 3.13 (d, J=17.2 Hz, 2H), 1.42 (t, J=7.0 Hz, 3H). ESIMS m/z [M+H]$^+$ 420.5.

Example 53: 8-Ethyl-3-indan-2-yloxy-6-[(2R)-2-methylmorpholine-4-carbonyl)pyrido[2,3-c]pyridazin-5-one

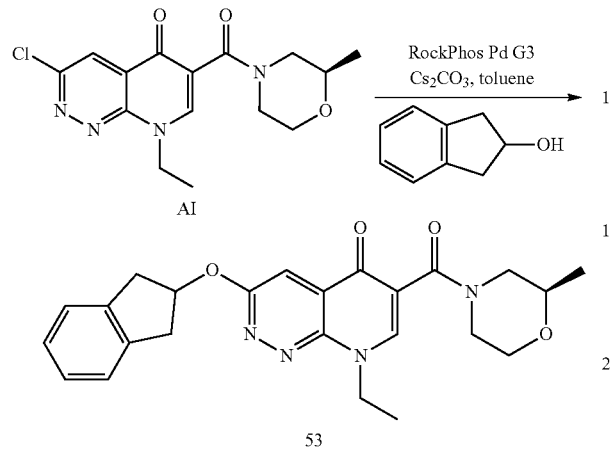

53

3-Chloro-8-ethyl-6-[(2R)-2-methylmorpholine-4-carbonyl]pyrido[2,3-c]pyridazin-5-one (400 mg, 1.18 mmol), 2-indanol (318 mg, 2.37 mmol), cesium carbonate (774 mg, 2.37 mmol) and RockPhos G3 Pd (60 mg, 0.07 mmol) in toluene (10 ml) were reacted as described under General Procedure B (18 h at 80° C.) to furnish the title compound (78 mg, 15%) as a yellow foam. $^1$H NMR (300 MHz, DMSO-$d_6$) δ 8.53 (s, 1H), 7.60 (s, 1H), 7.28-7.26 (m, 2H), 7.18-7.15 (m, 2H), 6.00-5.95 (m, 1H), 4.61-4.51 (m, 2H), 4.28 (t, J=9.0 Hz, 1H), 3.85-3.36 (m, 7H), 3.13 (d, J=17.2 Hz, 2H), 2.79-2.71 (m, 1H), 1.42 (t, J=7.0 Hz, 3H), 1.11 and 0.94 (2d, J=5.7 Hz, 3H). ESIMS m/z [M+H]$^+$ 435.1.

Example 54: 8-Ethyl-3-indan-2-yloxy-6-[(2R)-2-isopropylmorpholine-4-carbonyl)pyrido[2,3-c]pyridazin-5-one

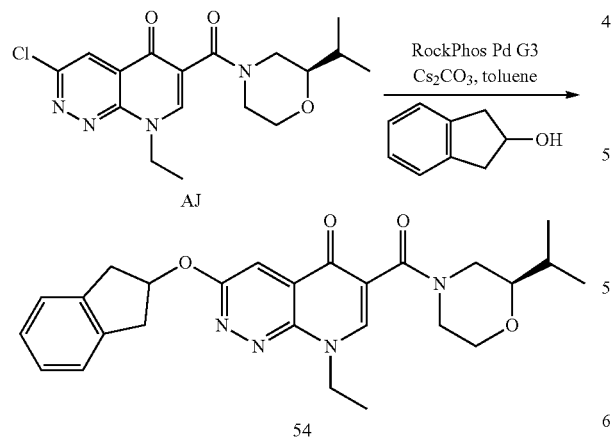

54

3-Chloro-8-ethyl-6-[(2R)-2-isopropylmorpholine-4-carbonyl]pyrido[2,3-c]pyridazin-5-one (457 mg, 1.25 mmol), 2-indanol (335 mg, 2.50 mmol), cesium carbonate (815 mg, 2.50 mmol) and RockPhos G3 Pd (59 mg, 0.07 mmol) in toluene (15 ml) were reacted as described under General Procedure B (24 h at 80° C.) to furnish the title compound (93 mg, 16%) as a yellow foam. $^1$H NMR (300 MHz, DMSO-$d_6$) δ 8.54 (s, 1H), 7.59 (s, 1H), 7.29-7.26 (m, 2H), 7.20-7.15 (m, 2H), 6.00-5.95 (m, 1H), 4.56 (qd, J=6.9 Hz, 2H), 4.36 and 4.25 (2d, J=11.8 Hz, 1H), 3.90 and 3.74 (2d, J=10.7 Hz, 1H), 3.52-3.37 (m, 4H), 3.13 (d, J=17.3 Hz, 2H), 3.04-2.48 (m, 3H), 1.73-1.45 (m, 1H), 1.42 (t, J=7.0 Hz, 3H), 0.93-0.71 (m, 6H). ESIMS m/z [M+H]$^+$ 463.1.

Example 55: 6-(2,2-Dimethylmorpholine-4-carbonyl)-8-ethyl-3-indan-2-yloxy-pyrido[2,3-c]pyridazin-5-one

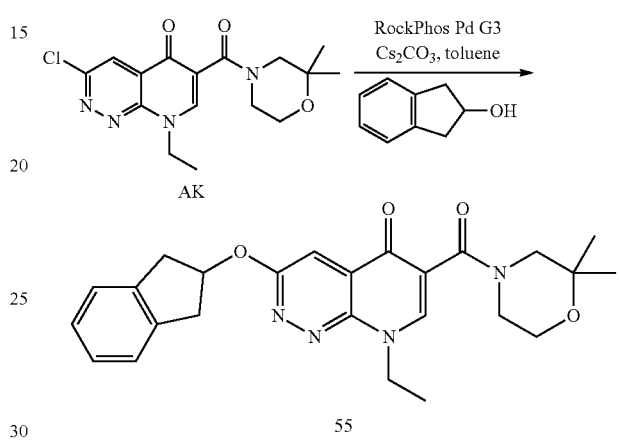

55

3-Chloro-6-(2,2-dimethylmorpholine-4-carbonyl)-8-ethyl-pyrido[2,3-c]pyridazin-5-one (206 mg, 0.59 mmol), 2-indanol (158 mg, 1.17 mmol), cesium carbonate (383 mg, 1.17 mmol) and RockPhos G3 Pd (30 mg, 0.07 mmol) in toluene (9 ml) were reacted as described under General Procedure B (18 h at 80° C.) to furnish the title compound (12 mg, 4%) as a yellow foam. $^1$H NMR (300 MHz, DMSO-$d_6$) δ 8.54 (s, 1H), 7.62-7.54 (m, 2H), 7.28-7.26 (m, 2H), 7.18-7.15 (m, 2H), 6.00-5.95 (m, 1H), 4.56 (qd, J=6.9 Hz, 2H), 3.61 (brs, 2H), 3.52-3.39 (m, 3H), 3.20-3.10 (m, 4H), 1.42 (t, J=6.0 Hz, 3H), 1.19 and 1.00 (2s, 6H). ESIMS m/z [M+H]$^+$ 449.1.

Example 56: 8-Ethyl-3-indan-2-yloxy-6-(2,2,6,6-tetramethylmorpholine-4-carbonyl)-pyrido[2,3-c]pyridazin-5-one

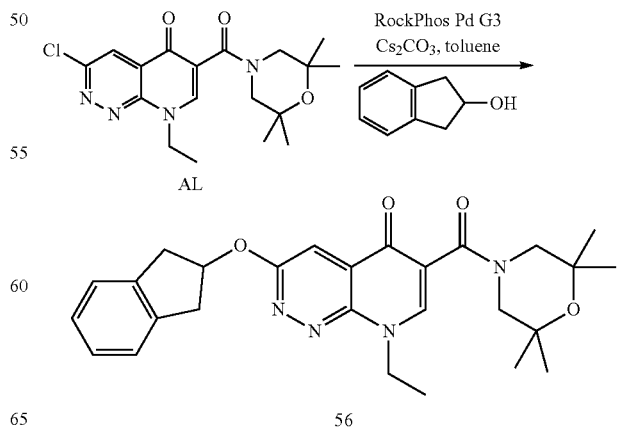

56

3-Chloro-6-(2,2,6,6-tetramethylmorpholine-4-carbonyl)-8-ethyl-pyrido[2,3-c]pyridazin-5-one (200 mg, 0.53 mmol), 2-indanol (142 mg, 1.06 mmol), cesium carbonate (344 mg, 1.06 mmol) and RockPhos G3 Pd (27 mg, 0.03 mmol) in toluene (7 ml) were reacted as described under General Procedure B (18 h at 80° C.) to furnish the title compound (20 mg, 7%) as a yellow foam. $^{1}$H NMR (300 MHz, DMSO-d$_{6}$) δ 8.63 (s, 1H), 7.60 (s, 1H), 7.29-7.26 (m, 2H), 7.19-7.15 (m, 2H), 6.01-5.97 (m, 1H), 4.57 (qd, J=6.8 Hz, 2H), 3.48 (dd, J=17.1, 6.1 Hz, 2H), 3.41 (brs, 2H), 3.16-3.10 (m, 4H), 1.40 (t, J=6.9 Hz, 3H), 1.17 (s, 6H), 1.00 (s, 6H). ESIMS m/z [M+H]$^{+}$ 477.2.

Example 57: 8-Ethyl-3-indan-2-yloxy-6-[(2R)-2-(methoxymethyl)morpholine-4-carbonyl)pyrido[2,3-c]pyridazin-5-one

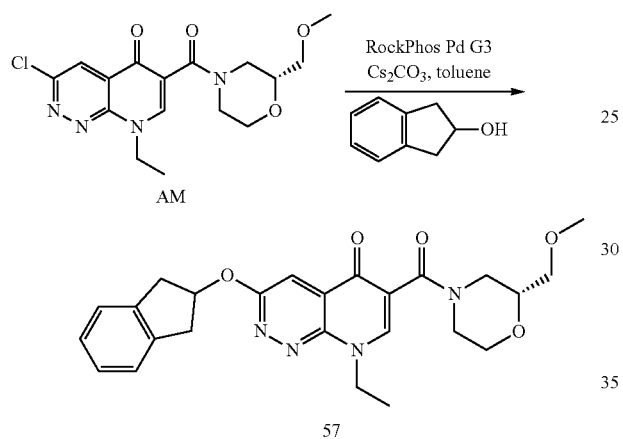

AM

57

3-Chloro-8-ethyl-6-[(2R)-2-(methoxymethyl)morpholine-4-carbonyl]pyrido[2,3-c]pyridazin-5-one (458 mg, 1.25 mmol), 2-indanol (335 mg, 2.50 mmol), cesium carbonate (813 mg, 2.50 mmol) and RockPhos G3 Pd (63 mg, 0.07 mmol) in toluene (15 ml) were reacted as described under General Procedure B (24 h at 80° C.) to furnish the title compound (110 mg, 19%) as a yellow foam. $^{1}$H NMR (300 MHz, DMSO-d$_{6}$) δ 8.54 (s, 1H), 7.60 (s, 1H), 7.29-7.26 (m, 2H), 7.18-7.15 (m, 2H), 6.00-5.95 (m, 1H), 4.60-4.51 (m, 2H), 4.37-4.24 (m, 1H), 3.88 and 3.72 (2d, J=10.8 Hz, 1H), 3.53-3.35 (m, 6H), 3.26-3.10 (m, 6H), 2.94-2.71 (m, 2H), 1.42 (t, J=7.0 Hz, 3H). ESIMS m/z [M+H]$^{+}$ 465.1.

Example 58: 8-Ethyl-3-indan-2-yloxy-6-[(3S)-3-(methoxymethyl)morpholine-4-carbonyl)pyrido[2,3-c]pyridazin-5-one

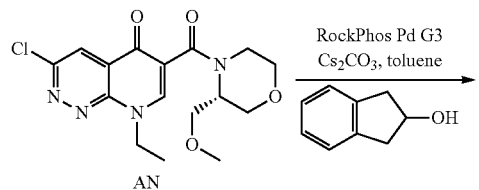

AN

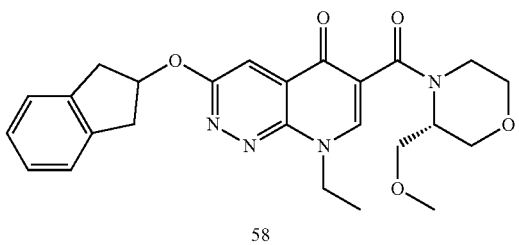

58

3-Chloro-8-ethyl-6-[(3S)-3-(methoxymethyl)morpholine-4-carbonyl]pyrido[2,3-c]pyridazin-5-one (340 mg, 0.93 mmol), 2-indanol (250 mg, 1.86 mmol), cesium carbonate (600 mg, 1.86 mmol) and RockPhos G3 Pd (50 mg, 0.06 mmol) in toluene (10 ml) were reacted as described under General Procedure B (18 h at 80° C.) to furnish the title compound (75 mg, 17%) as a yellow foam. $^{1}$H NMR (300 MHz, DMSO-d$_{6}$) δ 8.54 and 8.51 (2s, 1H), 7.62 (s, 1H), 7.30-7.28 (m, 2H), 7.20-7.17 (m, 2H), 6.03-5.98 (m, 1H), 4.75-4.30 (m, 3H), 4.18-4.36 (m, 9H), 3.28-3.12 (m, 6H), 1.43 (t, J=6.6 Hz, 3H). ESIMS m/z [M+H]$^{+}$ 465.1.

Example 59: 6-[(2R,5R)-2,5-dimethylmorpholine-4-carbonyl]-8-ethyl-3-indan-2-yloxy-pyrido[2,3-c]pyridazin-5-one

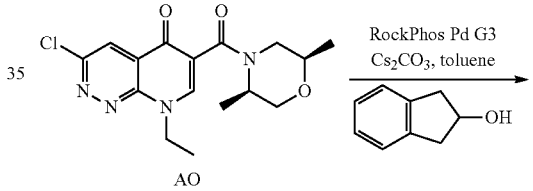

AO

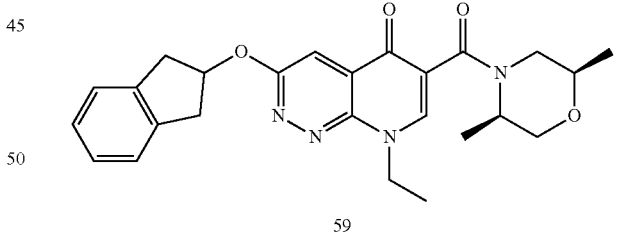

59

3-Chloro-6-[(2R,5R)-2,5-dimethylmorpholine-4-carbonyl]-8-ethyl-pyrido[2,3-c]pyridazin-5-one (588 mg, 1.60 mmol), 2-indanol (450 mg, 3.30 mmol), cesium carbonate (1.10 g, 3.30 mmol) and RockPhos G3 Pd (85 mg, 0.10 mmol) in toluene (15 ml) were reacted as described under General Procedure B (24 h at 80° C.) to furnish the title compound (146 mg, 20%) as a yellow foam. $^{1}$H NMR (300 MHz, DMSO-d$_{6}$) δ 8.55 and 8.53 (2 s, 1H), 7.62 and 7.61 (2s, 1H), 7.31-7.28 (m, 2H), 7.22-7.17 (m, 2H), 6.02-5.98 (m, 1H), 4.61-4.53 (m, 2H), 4.49-4.15 (m, 1H), 3.70-3.36 (m, 5H), 3.283.12 (m, 3H), 2.99-2.63 (m, 1H), 1.44 (t, J=6.9 Hz, 3H), 1.23-0.97 (m, 6H). ESIMS m/z [M+H]$^{+}$ 449.1.

Example 60: 8-Ethyl-3-indan-2-yloxy-6-(6-oxa-3-azabicyclo[3.1.1]heptane-3-carbonyl)pyrido[2,3-c]pyridazin-5-one

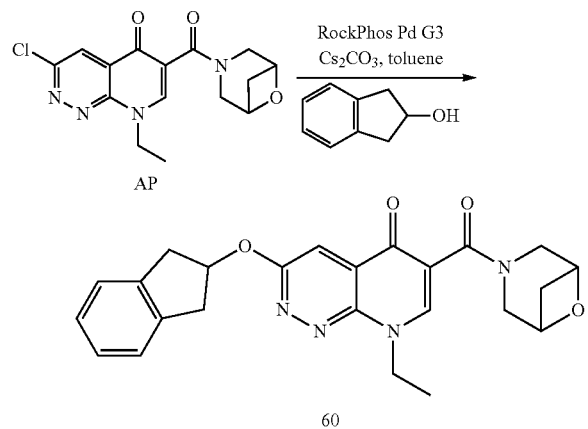

3-Chloro-8-ethyl-6-(6-oxa-3-azabicyclo[3.1.1]heptane-3-carbonyl) pyrido[2,3-c]pyridazin-5-one (210 mg, 0.63 mmol), 2-indanol (169 mg, 1.26 mmol), cesium carbonate (411 mg, 1.21 mmol) and RockPhos G3 Pd (32 mg, 0.04 mmol) in toluene (7 ml) were reacted as described under General Procedure B (18 h at 80° C.) to furnish the title compound (19 mg, 7%) as a yellow foam. $^1$H NMR (300 MHz, DMSO-$d_6$) δ 8.58 (s, 1H), 7.62 (s, 1H), 7.29-7.26 (m, 2H), 7.18-7.15 (m, 2H), 6.01-5.95 (m, 1H), 4.63-4.54 (m, 3H), 4.45 (brs, 1H), 3.87 (d, J=13.6 Hz, 1H), 3.70 (d, J=12.1 Hz, 1H), 3.57-3.44 (m, 4H), 3.14 (d, J=17.3 Hz, 2H), 3.10-3.04 (m, 1H), 1.79 (d, J=8.8 Hz, 1H), 1.43 (t, J=7.0 Hz, 3H). ESIMS m/z [M+H]$^+$ 433.1.

Example 61: 8-Ethyl-3-indan-2-yloxy-6-{(1R,4R)-2-oxa-5-azabicyclo[2.2.1]heptane-5-carbonyl}pyrido[2,3-c]pyridazin-5-one

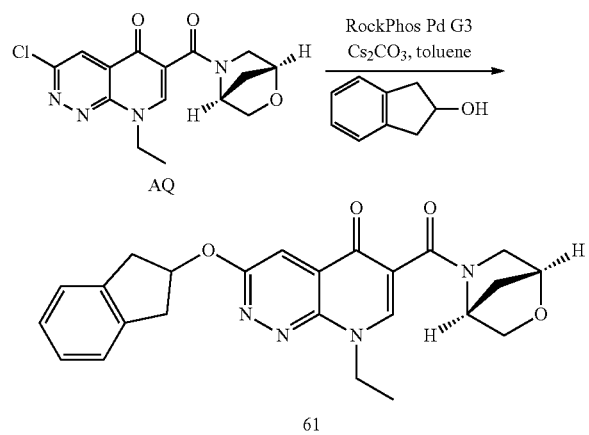

3-Chloro-8-ethyl-6-{(1R,4R)-2-oxa-5-azabicyclo[2.2.1]heptane-5-carbonyl}pyrido[2,3-c] pyridazin-5-one (169 mg, 0.50 mmol), 2-indanol (135 mg, 1.00 mmol), cesium carbonate (326 mg, 1.00 mmol) and RockPhos G3 Pd (26 mg, 0.03 mmol) in toluene (6 ml) were reacted as described under General Procedure B (72 h at 80° C.) to furnish the title compound (18 mg, 8%) as a yellow foam. $^1$H NMR (300 MHz, DMSO-$d_6$) δ 8.60 (s, 1H), 7.65 and 7.61 (2s, 1H), 7.31-7.28 (m, 2H), 7.21-7.18 (m, 2H), 6.02-5.98 (m, 1H), 4.81 and 4.29 (2s, 1H), 4.63-4.55 (m, 3H), 3.93-3.41 (m, 5H), 3.29-3.25 (m, 2H), 3.15 (d, J=17.1 Hz, 2H), 1.81 and 1.75 (2s, 1H), 1.45 (t, J=6.9 Hz, 3H). ESIMS m/z [M+H]$^+$ 433.1.

Example 62: 8-Ethyl-3-indan-2-yloxy-6-(3-oxa-8-azabicyclo[3.2.1]octane-8-carbonyl)pyrido[2,3-c]pyridazin-5-one

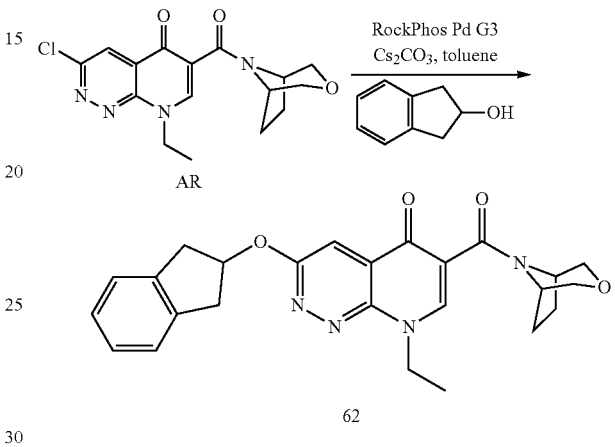

3-Chloro-8-ethyl-6-(3-oxa-8-azabicyclo[3.2.1]octane-8-carbonyl)pyrido[2,3-c]pyridazin-5-one (176 mg, 0.50 mmol), 2-indanol (135 mg, 1.00 mmol), cesium carbonate (326 mg, 1.00 mmol) and RockPhos G3 Pd (26 mg, 0.03 mmol) in toluene (6 ml) were reacted as described under General Procedure B (72 h at 80° C.) to furnish the title compound (22 mg, 10%) as a yellow foam. $^1$H NMR (300 MHz, DMSO-$d_6$) δ 8.63 (s, 1H), 7.63 (s, 1H), 7.30-7.28 (m, 2H), 7.20-7.18 (m, 2H), 6.02-5.97 (m, 1H), 4.60 (qd, J=7.1 Hz, 2H), 4.49 (brs, 1H), 3.82 (brs, 1H), 3.63-3.45 (m, 6H), 3.15 (d, J=17.2 Hz, 2H), 1.93-1.75 (m, 4H), 1.45 (t, J=7.0 Hz, 3H). ESIMS m/z [M+H]$^+$ 447.1.

Example 63: 8-Ethyl-3-indan-2-yloxy-6-(8-oxa-3-azabicyclo[3.2.1]octane-3-carbonyl)pyrido[2,3-c]pyridazin-5-one

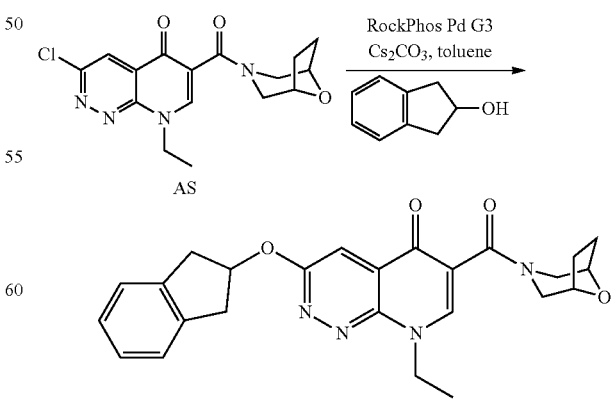

3-Chloro-8-ethyl-6-(8-oxa-3-azabicyclo[3.2.1]octane-3-carbonyl)pyrido[2,3-c]pyridazin-5-one (180 mg, 0.52 mmol), 2-indanol (138 mg, 1.00 mmol), cesium carbonate (336 mg, 1.03 mmol) and RockPhos G3 Pd (26 mg, 0.03 mmol) in toluene (5 ml) were reacted as described under General Procedure B (24 h at 70° C.) to furnish the title compound (17 mg, 7%) as a yellow foam. $^1$H NMR (300 MHz, DMSO-d$_6$) δ 8.54 (s, 1H), 7.59 (s, 1H), 7.29-7.26 (m, 2H), 7.18-7.15 (m, 2H), 6.00-5.95 (m, 1H), 4.57 (qd, J=7.2 Hz, 2H), 4.35 (brs, 1H), 4.16-4.06 (m, 2H), 3.48 (dd, J=17.2, 6.0 Hz, 2H), 3.25-3.19 (m, 2H), 3.13 (d, J=17.1 Hz, 2H), 2.90 (d, J=13.1 Hz, 1H), 1.90-1.60 (m, 4H), 1.42 (t, J=7.0 Hz, 3H). ESIMS m/z [M+H]$^+$ 447.1.

Example 64: 8-Ethyl-3-indan-2-yloxy-6-(3-oxa-9-azabicyclo[3.3.1]nonane-9-carbonyl)pyrido[2,3-c]pyridazin-5-one

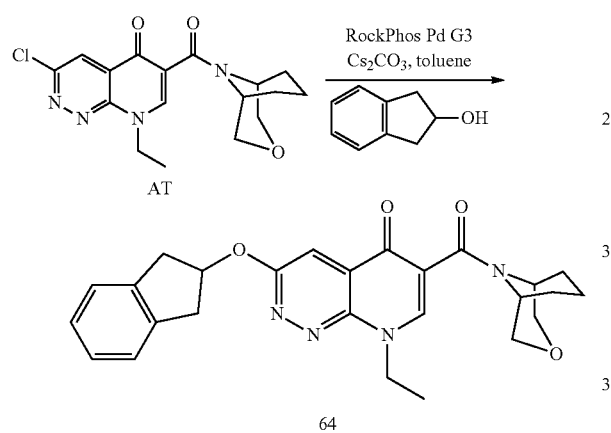

3-Chloro-8-ethyl-6-(3-oxa-9-azabicyclo[3.3.1]nonane-9-carbonyl) pyrido[2,3-c]pyridazin-5-one (259 mg, 0.71 mmol), 2-indanol (192 mg, 1.43 mmol), cesium carbonate (465 mg, 1.43 mmol) and RockPhos G3 Pd (36 mg, 0.04 mmol) in toluene (10 ml) were reacted as described under General Procedure B (18 h at 80° C.) to furnish the title compound (20 mg, 4%) as a yellow foam. $^1$H NMR (300 MHz, DMSO-d$_6$) δ 8.56 (s, 1H), 7.59 (s, 1H), 7.28-7.25 (m, 2H), 7.20-7.15 (m, 2H), 6.01-5.95 (m, 1H), 4.57 (qd, J=6.8 Hz, 2H), 3.90 (d, J=11.2 Hz, 1H), 3.74 (s, 2H), 3.64 (d, J=10.4 Hz, 1H), 3.52-3.43 (m, 3H), 3.13 (d, J=17.2 Hz, 2H), 2.47-2.32 (m, 2H), 1.88-1.75 (m, 3H), 1.74-1.65 (m, 1H), 1.58-1.51 (m, 1H), 1.42 (t, J=6.9 Hz, 3H). ESIMS m/z [M+H]$^+$ 461.1.

Example 65: 8-Ethyl-3-indan-2-yloxy-6-(3-oxa-7-azabicyclo[3.3.1]nonane-7-carbonyl)pyrido[2,3-c]pyridazin-5-one

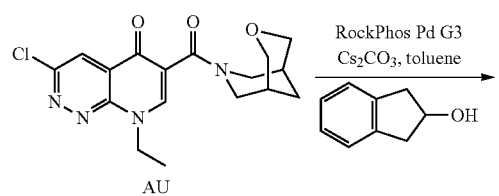

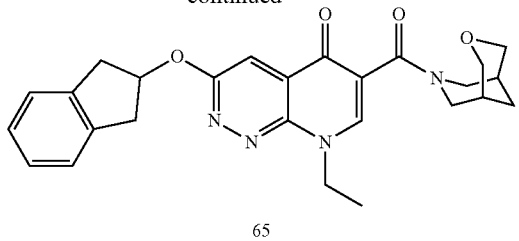

3-Chloro-8-ethyl-6-(3-oxa-7-azabicyclo[3.3.1]nonane-7-carbonyl)pyrido [2,3-c]pyridazin-5-one (580 mg, 1.60 mmol), 2-indanol (460 mg, 3.43 mmol), cesium carbonate (1.10 g, 3.38 mmol) and RockPhos G3 Pd (85 mg, 0.10 mmol) in toluene (16 ml) were reacted as described under General Procedure B (16 h at 75° C.) to furnish the title compound (233 mg, 32%) as a green solid. $^1$H NMR (300 MHz, DMSO-d$_6$) δ 8.27 (s, 1H), 7.59 (s, 1H), 7.27-7.23 (m, 2H), 7.20-7.16 (m, 2H), 6.00-5.96 (m, 1H), 4.67 (d, J=13.5 Hz, 1H), 4.58 (qd, J=7.0 Hz, 2H), 3.86-3.36 (m, 8H), 3.17-3.09 (m, 2H), 2.98 (d, J=13.0 Hz, 1H), 1.84 (brs, 2H), 1.73 (brs, 1H), 1.53 (brs, 1H), 1.39 (t, J=7.0 Hz, 3H). ESIMS m/z [M+H]$^+$ 461.1.

Example 66: 8-Ethyl-3-indan-2-yloxy-6-(2-oxa-6-azaspiro[3.3]heptane-6-carbonyl)pyrido[2,3-c]pyridazin-5-one

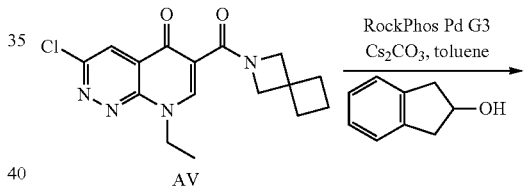

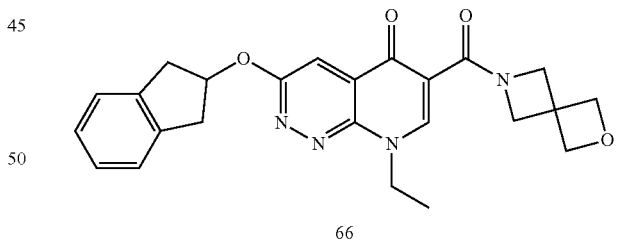

3-Chloro-8-ethyl-6-(2-oxa-6-azabicyclo[3.3]heptane-6-carbonyl)pyrido [2,3-c]pyridazin-5-one (490 mg, 1.46 mmol), 2-indanol (393 mg, 2.92 mmol), cesium carbonate (952 mg, 2.92 mmol) and RockPhos G3 Pd (74 mg, 0.09 mmol) in toluene (10 ml) were reacted as described under General Procedure B (18 h at 80° C.) to furnish the title compound (95 mg, 15%) as a yellow solid. $^1$H NMR (300 MHz, DMSO-d$_6$) δ 8.62 (s, 1H), 7.61 (s, 1H), 7.29-7.26 (m, 2H), 7.19-7.15 (m, 2H), 6.02-5.94 (m, 1H), 4.65-4.55 (m, 6H), 4.21 (s, 2H), 4.14 (s, 2H), 3.48 (dd, J=17.2, 6.2 Hz, 2H), 3.14 (dd, J=17.2, 2.1 Hz, 2H), 1.41 (t, J=7.0 Hz, 3H). ESIMS m/z [M+H]$^+$ 433.1.

Example 67: 8-Ethyl-3-indan-2-yloxy-6-(7-oxa-2-azaspiro[3.5]nonane-2-carbonyl)pyrido[2,3-c]pyridazin-5-one

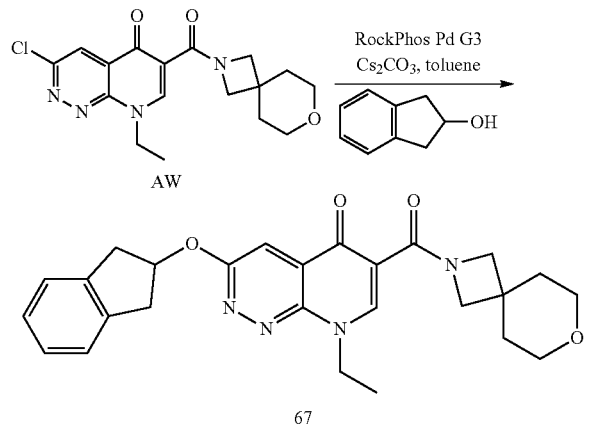

3-Chloro-8-ethyl-6-(7-oxa-6-azabicyclo[3.5]nonane-2-carbonyl)pyrido [2,3-c]pyridazin-5-one (310 mg, 0.85 mmol), 2-indanol (230 mg, 1.70 mmol), cesium carbonate (557 mg, 1.70 mmol) and RockPhos G3 Pd (43 mg, 0.05 mmol) in toluene (10 ml) were reacted as described under General Procedure B (32 h at 80° C.) to furnish the title compound (30 mg, 7%) as a yellow foam. $^1$H NMR (300 MHz, DMSO-$d_6$) δ 8.64 (s, 1H), 7.62 (s, 1H), 7.29-7.26 (m, 2H), 7.19-7.16 (m, 2H), 6.02-5.96 (m, 1H), 4.58 (qd, J=7.1 Hz, 2H), 3.79 (s, 2H), 3.70 (s, 2H), 3.53-3.38 (m, 6H), 3.14 (dd, J=17.2, 2.2 Hz, 2H), 1.64 (t, J=5.0 Hz, 4H), 1.38 (t, J=7.0 Hz, 3H). ESIMS m/z [M+H]$^+$ 461.1.

Example 68: 8-Ethyl-3-indan-2-yloxy-6-(1-oxa-7-azaspiro[4.4]nonane-7-carbonyl)pyrido[2,3-c]pyridazin-5-one

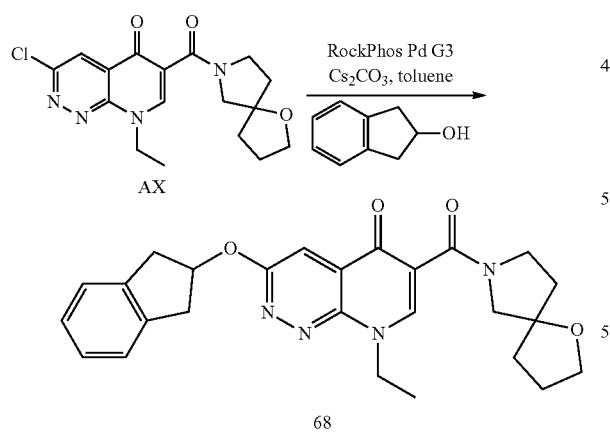

3-Chloro-8-ethyl-6-(7-oxa-6-azabicyclo[3.5]nonane-2-carbonyl)pyrido [2,3-c]pyridazin-5-one (476 mg, 1.31 mmol), 2-indanol (351 mg, 2.62 mmol), cesium carbonate (855 mg, 2.62 mmol) and RockPhos G3 Pd (66 mg, 0.08 mmol) in toluene (15 ml) were reacted as described under General Procedure B (18 h at 80° C.) to furnish the title compound (65 mg, 11%) as a yellow foam. $^1$H NMR (300 MHz, DMSO-$d_6$) δ 8.56 and 8.54 (2s, 1H), 7.61 (s, 1H), 7.29-7.25 (m, 2H), 7.20-7.15 (m, 2H), 6.02-5.94 (m, 1H), 4.57 (qd, J=7.1 Hz, 2H), 3.75-3.35 (m, 7H), 3.24-10 (m, 3H), 1.94-1.70 (m, 6H), 1.42 (t, J=6.8 Hz, 3H). ESIMS m/z [M+H]$^+$ 461.1.

Example 69: 8-Ethyl-3-indan-2-yloxy-6-(2-oxa-7-azaspiro[4.4]nonane-7-carbonyl)pyrido[2,3-c]pyridazin-5-one

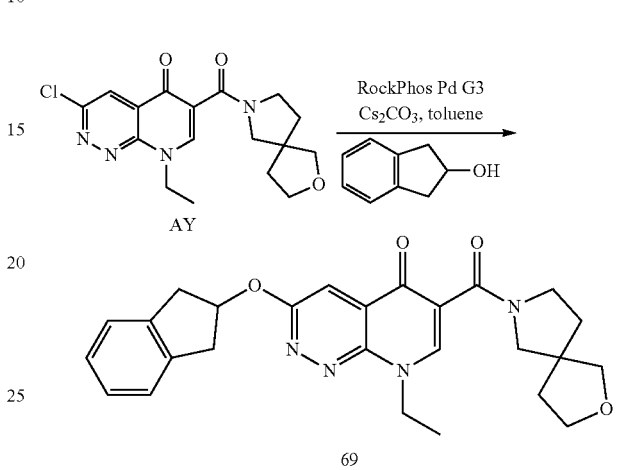

3-Chloro-8-ethyl-6-(2-oxa-7-azaspiro[4.4]nonane-7-carbonyl)pyrido [2,3-c]pyridazin-5-one (420 mg, 1.16 mmol), 2-indanol (320 mg, 2.38 mmol), cesium carbonate (780 mg, 2.39 mmol) and RockPhos G3 Pd (60 mg, 0.07 mmol) in toluene (15 ml) were reacted as described under General Procedure B (16 h at 75° C.) to furnish the title compound (140 mg, 26%) as a yellow foam. $^1$H NMR (300 MHz, DMSO-$d_6$) δ 8.55 (s, 1H), 7.61 (s, 1H), 7.29-7.25 (m, 2H), 7.20-7.15 (m, 2H), 6.02-5.94 (m, 1H), 4.56 (qd, J=6.9 Hz, 2H), 3.79-3.29 (m, 10H), 3.13 (d, J=17.2 Hz, 2H), 1.89-1.74 (m, 4H), 1.42 (t, J=7.0 Hz, 3H). ESIMS m/z [M+H]$^+$ 461.1.

A2B Protocol

Permeability Data for Compounds was Collected Using the Following Experimental Procedure:

MDCK-MDR1 cells obtained from the NIH (Rockville, Md., USA) are used between passage numbers 6-30. Cells are seeded onto Millipore Multiscreen Transwell plates at 3.4×105 cells/cm2. The cells are cultured in DMEM and media is changed on day 3. On day 4 the permeability study is performed. Cell culture and assay incubations are carried out at 37° C. in an atmosphere of 5% CO2 with a relative humidity of 95%. On the day of the assay, the monolayers are prepared by rinsing both apical and basolateral surfaces twice with Hanks Balanced Salt Solution (HBSS) at the desired pH warmed to 37° C. Cells are then incubated with HBSS at the desired pH in both apical and basolateral compartments for 40 min to stabilise physiological parameters.

The dosing solutions are prepared by diluting test compound with assay buffer to give a final test compound concentration of 10 μM (final DMSO concentration of 1% v/v). The fluorescent integrity marker lucifer yellow is also included in the dosing solution. Analytical standards are prepared from test compound DMSO dilutions and transferred to buffer, maintaining a 1% v/v DMSO concentration.

Typical assay buffer is composed of supplemented HBSS pH 7.4 but a range of other buffers and pH values can be used.

For assessment of A-B permeability, HBSS is removed from the apical compartment and replaced with test compound dosing solution. The apical compartment insert is then placed into a companion plate containing fresh buffer (containing 1% v/v DMSO). For assessment of B-A permeability, HBSS is removed from the companion plate and replaced with test compound dosing solution. Fresh buffer (containing 1% v/v DMSO) is added to the apical compartment insert, which is then placed into the companion plate.

At 60 min the apical compartment inserts and the companion plates are separated and apical and basolateral samples diluted for analysis.

Test compound permeability is assessed in duplicate. Compounds of known permeability characteristics are run as controls on each assay plate.

Test and control compounds are quantified by LC-MS/MS cassette analysis using a 7-point calibration with appropriate dilution of the samples. Cyprotex generic analytical conditions are used. The starting concentration (C0) is determined from the dosing solution and the experimental recovery calculated from C0 and both apical and basolateral compartment concentrations.

The integrity of the monolayer throughout the experiment is checked by monitoring lucifer yellow permeation using fluorimetric analysis. Lucifer yellow permeation is high if monolayers have been damaged. If a lucifer yellow Papp value is above a pre-defined threshold in one well, but the derived Papp result for test compound or marker compound in that well is qualitatively similar to that determined in the remaining replicate well (within the lucifer yellow threshold) then, based upon the scientific judgment of the responsible scientist, the cell monolayer may be considered acceptable. If this is not the case, then the result from the affected monolayer is excluded and an n=1 result is reported, or the compound may be retested. If lucifer yellow Papp values are above the threshold in both replicate wells for a test compound, the compound is re-tested. If this re-occurs upon repeat in both wells then toxicity or inherent fluorescence of the test compound is assumed. No further experiments are performed in this instance.

Data Analysis:

The permeability coefficient ($P_{app}$) for each compound is calculated from the following equation:

$$P_{app} = \left(\frac{dQ/dt}{C_0 \times A}\right)$$

Where dQ/dt is the rate of permeation of the drug across the cells, C0 is the donor compartment concentration at time zero and A is the area of the cell monolayer. C0 is obtained from analysis of the dosing solution.

For bi-directional experiments, an efflux ratio (ER) is calculated from mean A-B and B-A data.

This is derived from:

$$ER = \frac{P_{app(B-A)}}{P_{app(A-B)}}$$

Two control compounds are screened alongside the test compounds, propranolol (highly permeable) and prazosin (a substrate for P-glycoprotein).

TABLE 1

A2B $P_{app}$ Data

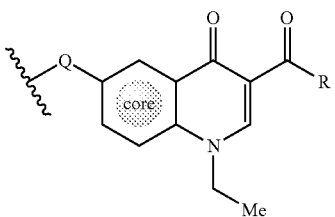

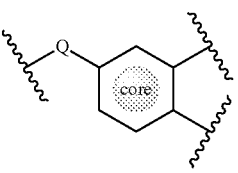 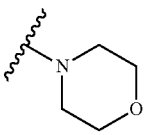 [SMILES: *N1CCOCC1] 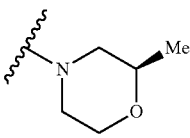 [SMILES: *N1CCO[C@H](C)C1] 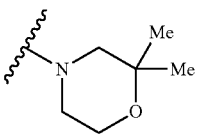 [SMILES: *N1CCOC(C)(C)C1]

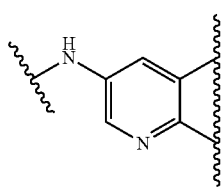 Comparator A2B $P_{app}$ ($10^{-6}$ cm/s)    0.61

TABLE 1-continued
A2B P_app Data
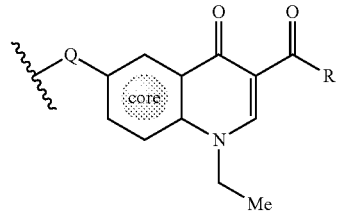
| Q | Example A2B P$_{app}$ (10$^{-6}$ cm/s) | 1 2.19 | 2 2.56 | 4 1.26 |
|---|---|---|---|---|
| 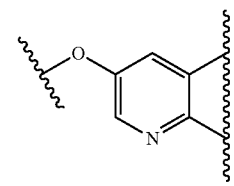 | | | | |
| 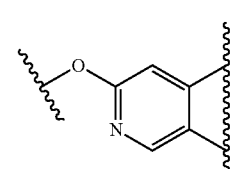 | Example A2B P$_{app}$ (10$^{-6}$ cm/s) | 26 1.56 | | |
| 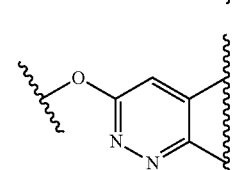 | Example A2B P$_{app}$ (10$^{-6}$ cm/s) | 52 4.78 | | |
| 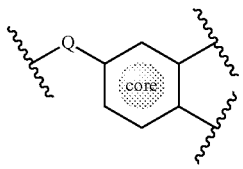 | R | 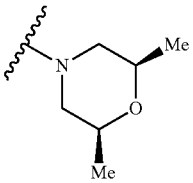 [SMILES: *N1C[C@@H](C)O[C@@H](C)C1] | 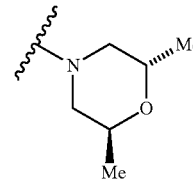 | 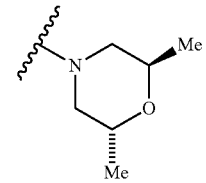 [SMILES: *N1C[C@@H](C)O[C@H](C)C1] |
|---|---|---|---|---|
| 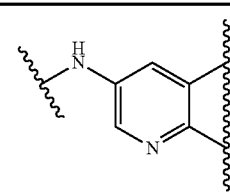 | Comparator A2B P$_{app}$ (10$^{-6}$ cm/s) | | | |
| 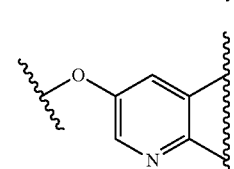 | Example A2B P$_{app}$ (10$^{-6}$ cm/s) | 5 3.41 | 6 1.7 | 7 1.79 |
| 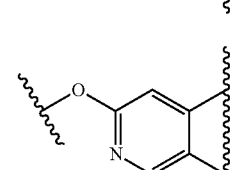 | Example A2B P$_{app}$ (10$^{-6}$ cm/s) | | | |

TABLE 1-continued
A2B P$_{app}$ Data
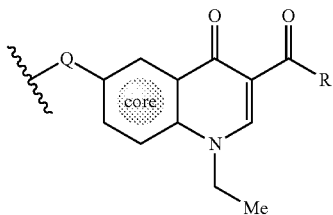
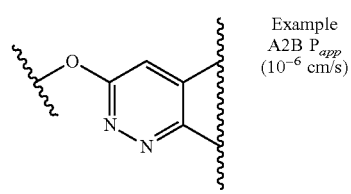
Example
A2B P$_{app}$
($10^{-6}$ cm/s)
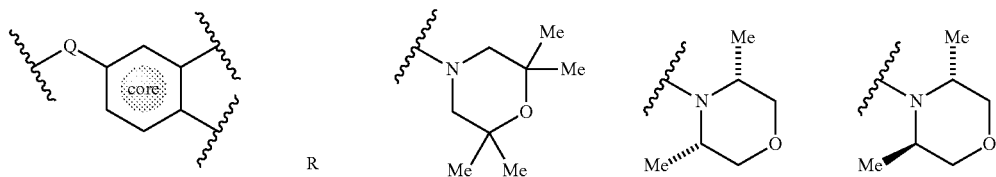
R
| | | | |
|---|---|---|---|
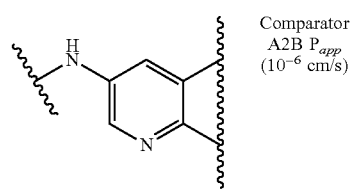
Comparator
A2B P$_{app}$
($10^{-6}$ cm/s)
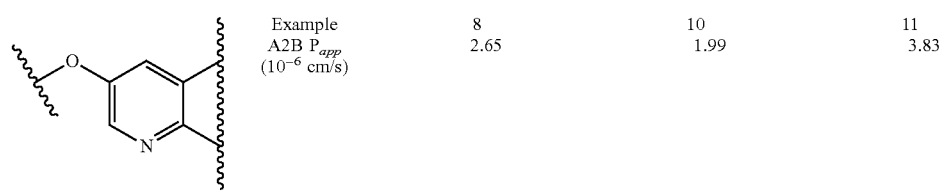
| Example | 8 | 10 | 11 |
| A2B P$_{app}$ | 2.65 | 1.99 | 3.83 |
| ($10^{-6}$ cm/s) | | | |
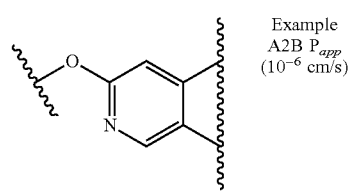
Example
A2B P$_{app}$
($10^{-6}$ cm/s)
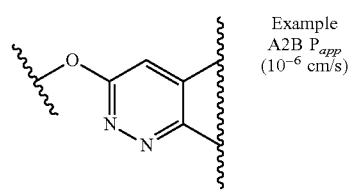
Example
A2B P$_{app}$
($10^{-6}$ cm/s)

TABLE 1-continued
A2B P$_{app}$ Data
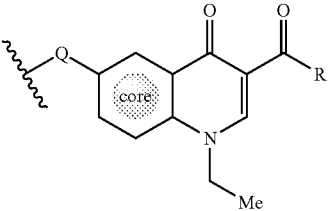
| | | 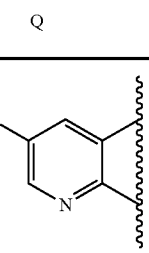 | 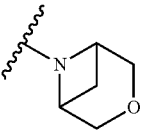 | 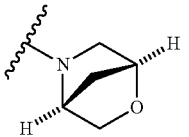 [SMILES: *N1C[C@@H]2C[C@H]1CO2] |
|---|---|---|---|---|
| Q | R | | | |
| 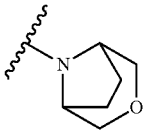 | Comparator A2B P$_{app}$ (10$^{-6}$ cm/s) | | | |
| 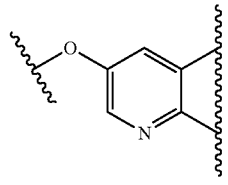 | Example A2B P$_{app}$ (10$^{-6}$ cm/s) | 16<br>2.06 | 17<br>0.87 | 18<br>1.41 |
| 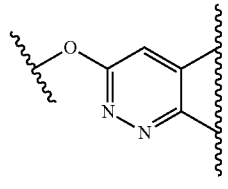 | Example A2B P$_{app}$ (10$^{-6}$ cm/s) | | | |
| | | 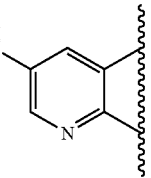 | 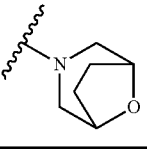 | 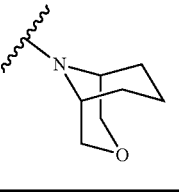 |
|---|---|---|---|---|
| Q | R | | | |
| 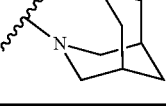 | Comparator A2B P$_{app}$ (10$^{-6}$ cm/s) | 2<br>0.25 | | |
| 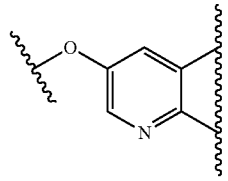 | Example A2B P$_{app}$ (10$^{-6}$ cm/s) | 19<br>1.79 | 20<br>2.01 | |

TABLE 1-continued

A2B P_{app} Data

| | Q | R | |
|---|---|---|---|
| | (pyridazine-O) | Example A2B P_{app} (10⁻⁶ cm/s) | 63 1.55     65 0.98 |
| | (pyridine-NH) | Comparator A2B P_{app} (10⁻⁶ cm/s) | (2-oxa-6-azaspiro[3.5]nonane) |
| | (pyridine-O) | Example A2B P_{app} (10⁻⁶ cm/s) | 23 1.24 |
| | (pyridazine-O) | Example A2B P_{app} (10⁻⁶ cm/s) | |

The claims defining the invention are as follows:
1. A compound of formula (I):

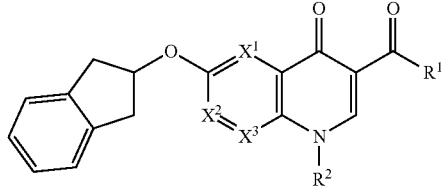

wherein:
R¹ is

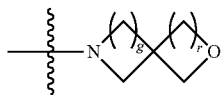

where g and r are independently 1, 2 or 3;

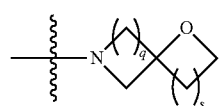

where q and s are independently 1, 2 or 3;
3-oxa-7-azabicyclo [3.3.1] nonane-7-yl group;
3-oxa-8-azabicyclo [3.2.1] octane-8-yl group;
3-oxa-3-azabicyclo [3.2.1] octane-8-yl group; or
3-oxa-9-azabicyclo [3.3.1] nonane-9-yl group;
R² is a C1-C3 alkyl; and
X¹, X², X³ are independently CH or N wherein at least one of X¹, X² or X³ is N,
or a pharmaceutically acceptable salt, solvate, prodrug, stereoisomer or tautomer thereof.

2. A compound of formula (I) according to claim 1, or a pharmaceutically acceptable salt, solvate, stereoisomer or tautomer thereof, wherein R² is ethyl.

3. A compound of formula (I) according to claim 1, or a pharmaceutically acceptable salt, solvate, stereoisomer or tautomer thereof, which is selected from a compound of sub-formulae (Ia)-(Id):

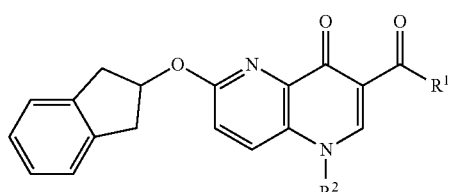

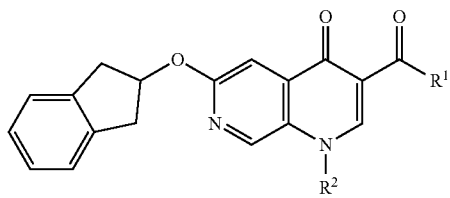

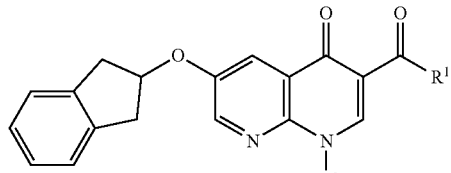

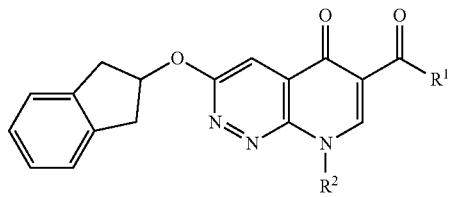

wherein R¹ and R² are as defined in claim 1.

4. A compound of formula (I) according to claim 3, or a pharmaceutically acceptable salt, solvate, stereoisomer or tautomer thereof, which is a compound of sub formula (Ic).

5. A compound of formula (I) according to claim 1, or a pharmaceutically acceptable salt, solvate, stereoisomer or tautomer thereof, wherein Ri is selected from one of the following:

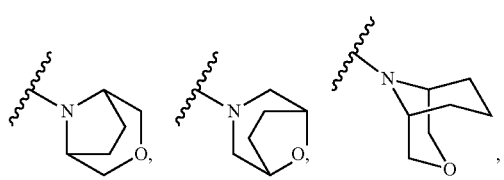

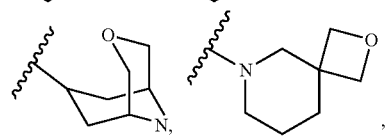

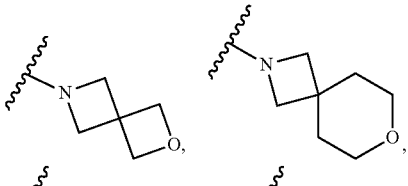

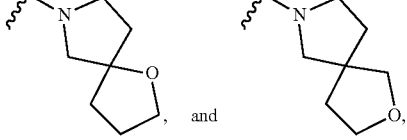

6. A method of medically treating a disease, disorder, or condition which would benefit from modulation of a7nAChR, said method including the step of administering to a patient in need thereof an effective amount of a compound of formula (I) according to claim 1, or a pharmaceutically acceptable salt thereof, wherein the disease, disorder or condition which would benefit from modulation of α7 nAChR is a disease, disorder or condition in which the benefit comes from the negative allosteric modulation of α7 nAChR.

7. The method according to claim 6 wherein the disease, disorder or condition in which the benefit comes from the negative allosteric modulation of α7 nAChR is a disease, disorder or condition selected from anxiety, depression, and a stress-related disorder.

8. A pharmaceutical composition comprising a compound of claim 1, or a pharmaceutically acceptable salt, solvate, stereoisomer or tautomer thereof, and a pharmaceutically acceptable carrier.

9. A compound of formula (I) according to claim 1, or a pharmaceutically acceptable salt, solvate, stereoisomer or tautomer thereof, wherein $R^1$ is 3-oxa-7-azabicyclo [3.3.1] nonane-7-yl group.

10. A compound of formula (I) according to claim 1, or a pharmaceutically acceptable salt, solvate, stereoisomer or tautomer thereof, selected from one of the following compounds:

69

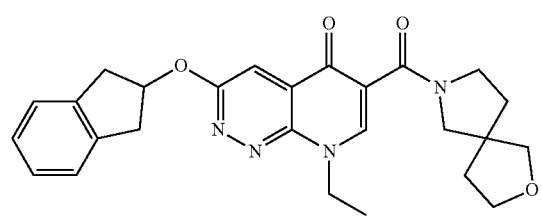

68

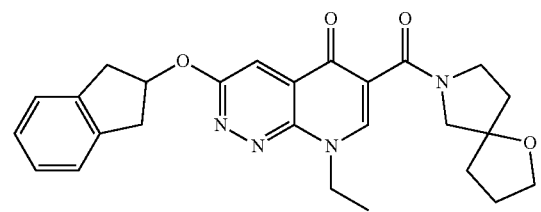

67

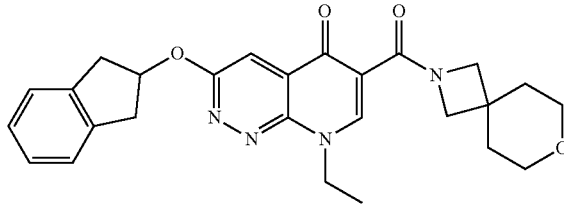

66

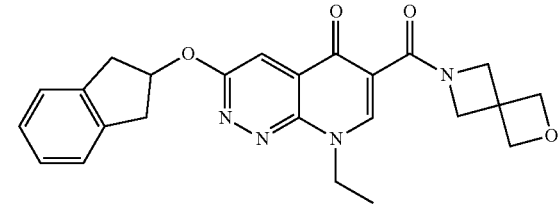

-continued

65

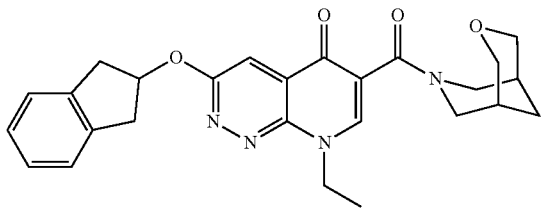

64

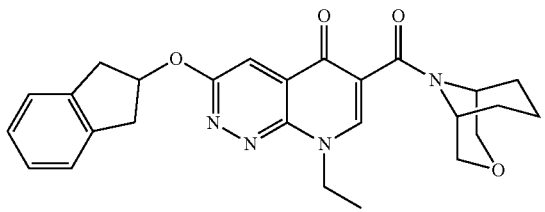

63

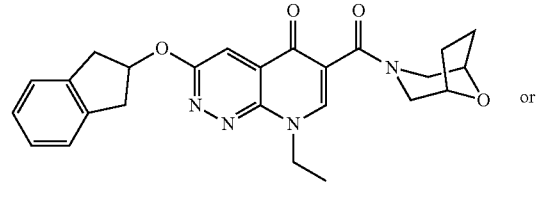

or

62

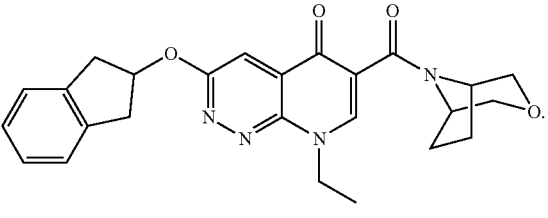

* * * * *